United States Patent
Downing et al.

(10) Patent No.: US 9,884,060 B2
(45) Date of Patent: *Feb. 6, 2018

(54) KIF5B-RET FUSION MOLECULES AND USES THEREOF

(71) Applicant: FOUNDATION MEDICINE, INC., Cambridge, MA (US)

(72) Inventors: Sean R. Downing, Methuen, MA (US); Matthew J. Hawryluk, Watertown, MA (US); Doron Lipson, Chestnut Hill, MA (US); Alexander N. Parker, Boston, MA (US); Philip James Stephens, Lexington, MA (US)

(73) Assignee: FOUNDATION MEDICINE, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/045,716

(22) Filed: Feb. 17, 2016

(65) Prior Publication Data

US 2017/0014413 A1    Jan. 19, 2017

Related U.S. Application Data

(60) Division of application No. 14/187,280, filed on Feb. 23, 2014, now Pat. No. 9,297,011, which is a continuation of application No. PCT/US2012/051978, filed on Aug. 23, 2012.

(60) Provisional application No. 61/594,739, filed on Feb. 3, 2012, provisional application No. 61/542,112, filed on Sep. 30, 2011, provisional application No. 61/537,024, filed on Sep. 20, 2011, provisional application No. 61/526,613, filed on Aug. 23, 2011.

(51) Int. Cl.

| | |
|---|---|
| *A61K 31/517* | (2006.01) |
| *C07K 14/82* | (2006.01) |
| *C12N 9/14* | (2006.01) |
| *C12Q 1/68* | (2006.01) |
| *A61K 31/404* | (2006.01) |
| *A61K 31/4412* | (2006.01) |
| *A61K 31/444* | (2006.01) |
| *A61K 31/47* | (2006.01) |
| *A61K 31/513* | (2006.01) |
| *C12N 15/113* | (2010.01) |

(52) U.S. Cl.
CPC .......... *A61K 31/517* (2013.01); *A61K 31/404* (2013.01); *A61K 31/444* (2013.01); *A61K 31/4412* (2013.01); *A61K 31/47* (2013.01); *A61K 31/513* (2013.01); *C07K 14/82* (2013.01); *C12N 9/14* (2013.01); *C12N 15/1135* (2013.01); *C12Q 1/6886* (2013.01); *C07K 2319/00* (2013.01); *C12Q 2600/136* (2013.01); *C12Q 2600/156* (2013.01); *C12Q 2600/158* (2013.01)

(58) Field of Classification Search
CPC ... C07K 2319/00; A61K 31/517; A61K 31/47
See application file for complete search history.

(56) References Cited

U.S. PATENT DOCUMENTS

| | | |
|---|---|---|
| 5,605,798 A | 2/1997 | Koster |
| 6,455,258 B2 | 9/2002 | Bastian et al. |
| 9,297,011 B2 * | 3/2016 | Downing |
| 2006/0100168 A1 | 5/2006 | Ravid et al. |
| 2006/0246497 A1 | 11/2006 | Huang et al. |
| 2010/0029498 A1 | 2/2010 | Gnirke et al. |
| 2010/0130527 A1 | 5/2010 | Lehrer et al. |
| 2011/0003298 A1 | 1/2011 | Liew |
| 2011/0118298 A1 | 5/2011 | Fritz et al. |
| 2012/0208706 A1 | 8/2012 | Downing et al. |
| 2013/0137111 A1 | 5/2013 | Shindo et al. |

FOREIGN PATENT DOCUMENTS

| | | |
|---|---|---|
| EP | 2599878 A1 | 6/2013 |
| KR | 20040075272 A | 8/2004 |
| WO | 2007087245 A2 | 8/2007 |
| WO | 2013/018882 A1 | 2/2013 |
| WO | 2013/066047 A1 | 5/2013 |
| WO | 2013/111668 A1 | 8/2013 |
| WO | 2014071419 A2 | 5/2014 |
| WO | 2014130975 A1 | 8/2014 |

OTHER PUBLICATIONS

Altschul et al., "Basic Local Alignment Search Tool" J. Mol. Biol., 215:403-410 (1990).
Altschul et al., "Gapped BLAST and PSI-BLAST: a new generation of protein database search programs" Nucleic Acids Research, 25(17):3389-3402 (1997).
Arighi et al., "RET tyrosine kinase signaling in development and cancer", Cytokine and Growth Factor Reviews. Elsevier Ltd. GB. (2005) vol. 16. No. 4-5 pp. 441-467.
Astrazeneca (Collaborator) PrECOG, LLC. (Sponsor), "A Randomized Phase II Study Evaluating Vandetanib in Patients with IIIb, IV or Recurrent Non-Small Cell Lung Cancer (NSCLC)" Identifier NCT00687297, Received: May 27, 2008.
Astrazeneca (Collaborator) Sikic, Branimir (Sponsor), "A Phrase I Trial of Vandetanib Combined with Capecitabine, Oxaliplatin and Bevacizumab for the First-Line Treatment of Metastic Colorectal Cancer" Identifier NCT00532909, Received: Sep. 20, 2007.

(Continued)

*Primary Examiner* — James D. Anderson
(74) *Attorney, Agent, or Firm* — Lando & Anastasi, LLP

(57) ABSTRACT

Novel RET fusion molecules and uses are disclosed. In one embodiment, a KIF5B-RET fusion includes an in-frame fusion of an exon of KIF5B (e.g., one or more exons encoding a kinesin motor domain or a fragment thereof) and an exon of RET (e.g., one or more exons encoding a RET tyrosine kinase domain or a fragment thereof). For example, the KIF5B-RET fusion can include an in-frame fusion of at least exon 15 of KIF5B or a fragment thereof (e.g., exons 1-15 of KIF5B or a fragment thereof) with at least exon 12 of RET or a fragment thereof (e.g., exons 12-20 of RET or a fragment thereof).

27 Claims, 19 Drawing Sheets

(56) References Cited

OTHER PUBLICATIONS

Beaudry et al., "Potent antitumor effects of ZD6474 on neuroblastoma via dual targeting of tumor cells and tumor endothelium", Molecular Cancer Therapeutics (2008) vol. 7 No. 2 pp. 418-424.
Carlomagno et al., "BAY 43-9006 inhibition of oncogenic RET mutants" J Natl Cancer Inst. (2006) vol. 98 No. 5 pp. 326-334.
Carlomagno et al., "ZD6474, an orally available inhibitor of KDR tyrosine kinase activity, efficiently blocks oncogenic RET kinase", Cancer Research. American Association for Cancer Research. US. (2002) vol. 62 No. 24 pp. 7284-7290.
Drilon et al., "Response to Cabozantinib in Patients with RET Fusion-Positive Lung Adenocarcinomas" Cancer Discovery, 3:630-635 (2013).
Extended European Search Report and Written Opinion from Application No. 12825669.0 dated Jun. 17, 2015.
Futami et al., "Allelic loss of DNA locus of the RET proto-oncogene in small cell lung cancer" Cancer Letters (2003) 195:59-65.
Ganor and Shaw, "The New Kid on the Block: RET in Lung Cancer" Cancer Discovery, 3:604-606 (2013).
GenBank Accession No. NM_004521.2 accessed Oct. 15, 2015 from http://www.ncbi.nlm.nih.gov/nuccore/NM_004521.2.
GenBank Accession No. NM_020975 accessed Oct. 15, 2015 from http://www.ncbi.nlm.nih.gov/nuccore/NM_020975.
GenBank Accession No. NP_004512 accessed Oct. 15, 2015 from http://www.ncbi.nlm.nih.gov/protein/NP_004512.
GenBank Accession No. NP_066124.1 accessed Oct. 15, 2015 from <http://www.ncbi.nlm.nih.gov/protein/NP_066124.1>.
Henderson et al., "Sorafenib potently inhibits papillary thyroid carcinomas harboring RET/PTC1 rearrangement", Clin Cancer Res (2008) vol. 14 No. 15 pp. 4908-4914.
International Preliminary Report on Patentability for PCT/US2012/051978 dated Feb. 25, 2014.
International Search Report for PCT/US20121051978 dated Dec. 17, 2012.
Ju, et al., "A Transforming KIF5B and RET gene fusion in lung adenocarcinoma revealed from whole-genome and transcriptome sequencing", Genome Research, 22:436-445, Dec. 22, 2011.
Ju, et al., "Fusion of KIF5B and RET transforming gene in lung adenocarcinoma revealed from whole-geneome and transcriptome sequencing." Genome Research, vol. 22: 436-445, 2012.
Karlin and Altschul "Applications and statistics for multiple high-scoring segments in molecular sequences" PNAS USA, 90:5873-5877 (1993).
Karlin and Altschul, "Methods for assessing the statistical significance of molecular sequence features by using general scoring schemes" PNAS USA, 87:2264-2268 (1990).

Kim et al., "An orally administered multitarget tyrosine kinase inhibitor, SU11248, is a novel potent inhibitor of thyroid oncogenic RET/papillary thyroid cancer kinases." J Clin Endocrinol Metab (2006) vol. 91 No. 10 pp. 4070-4076.
Kohno, et al. " KIF5B-RET fusions in lung adenocarcinoma" Nature Medicine 18:375-377, Mar. 2012.
Lipson, et al. "Idenification of new ALK and RET gene fusions from colorectal and lung cancer biopsies" Nature Medicine, 18:382-384, Mar. 2012.
Metzker et al., "Sequencing technologies—the next generation" Nature Reviews: Genetics, 11:31-46 (2010).
Okamoto et al., "Antitumor activities of the targeted multi-tyrosine kinase inhibitor lenvatinib (E7080) against RET gene fusion-driven tumor models", Cancer Letters (2013) vol. 340. No. 1. pp. 97-103.
Pearson and Lipman, "Improved tools for biological sequence comparison" PNAS USA, 85:2444-2448 (1988).
Plaza-Menacho et al., "Sorafenib Functions to Potently Suppress RET Tyrosine Kinase Activity by Direct Enzymatic Inhibition and Promoting RET Lysosomal Degradation Independent of Proteasomal Targeting", The Journal of Biological Chemistry (2007) vol. 282 No. 40 pp. 29230-29240.
Sathornsumetee et al. Drugs Today (Barc.), 2006, vol. 42, No. 10, pp. 657-670 (Abstract).
Song "Progress in Discovery of KIF5B-RET Kinase Inhibitors for the Treatment of Non-Small-Cell Lung Cancer". Journal of Medicinal Chemistry (2015) vol. 58. No. 9 pp. 3672-3681.
Suehara, et al., Idenfication of KIF5B-RET and GOPC-ROS1 fusions in lung adenocarcinomas through a comprehensive mRNA-based screen for tyrosine kinase fusions: Clin. Cancer. Res., pp. 1-22, Oct. 10, 2012.
Takeuchi et al., "KIF5B-ALK, a novel fusion oncokinase identified by an immunohistochemistry-based diagnostic system for ALK-positive lung cancer", Clin Cancer Res (2009) vol. 15 No. 9.
Ulahannan et al., "Antiangiogenic Agents in Combination with Chemotherapy in Patients with Advanced Non-Small Cell Lung Cancer", Cancer Investigation (2011) vol. 29 No. 1 pp. 325-337.
University of Texas M.D. Anderson Cancer Center. "Vandetanib Shows Clinical Benefit When Combined with Docetaxel for Lung Cancer." Science Daily. Science Daily, Jun. 3, 2009. <www.sciencedaily.com/releases/2009/06/090601092237.htm>.
Wong, et al., "A Novel KIF5B-ALK Variant in Nonsmall Cell Lung Cancer." Cancer 117:2709-2718, Jun. 15, 2011.
Written Opinion for PCT/US2012/051978 dated Dec. 17, 2012.
Written Opinion for Singapore Application No. 2014012728 dated Sep. 23, 2015.
Written Opinion from Singaporean Application No. 2014012728 dated Mar. 13, 2015.
"Protein Kinase Inhibitor—Wikipedia", Wikipedia, Aug. 5, 2011 (http:en.wikipedia.org/w/index.php?); Retrieved from the Internet on Mar. 16, 2017.

* cited by examiner

```
atg gcg gac ctg gcc gag tgc aac atc aaa gtg atg tgt cgc ttc aga cct ctc aac gag   60
 M   A   D   L   A   E   C   N   I   K   V   M   C   R   F   R   P   L   N   E   20 tct gaa gtg aac cgc ggc gac aag tac atc gcc aag ttt cag gga gaa gac acg gtc gtg  120
 S   E   V   N   R   G   D   K   Y   I   A   K   F   Q   G   E   D   T   V   V   40 atc gcg tcc aag cct tat gca ttt gat cgg gtg ttc cag tca agc aca tct caa gag caa  180
 I   A   S   K   P   Y   A   F   D   R   V   F   Q   S   S   T   S   Q   E   Q   60 gtg tat aat gac tgt gca aag aag att gtt aaa gat gta ctt gaa gga tat aat gga aca  240
 V   Y   N   D   C   A   K   K   I   V   K   D   V   L   E   G   Y   N   G   T   80 ata ttt gca tat gga caa aca tcc tct ggg aag aca cac aca atg gag ggt aaa ctt cat  300
 I   F   A   Y   G   Q   T   S   S   G   K   T   H   T   M   E   G   K   L   H  100 gat cca gaa ggc atg gga att att cca aga ata gtg caa gat att ttt aat tat att tac  360
 D   P   E   G   M   G   I   I   P   R   I   V   Q   D   I   F   N   Y   I   Y  120 tcc atg gat gaa aat ttg gaa ttt cat att aag gtt tca tat ttt gaa ata tat ttg gat  420
 S   M   D   E   N   L   E   F   H   I   K   V   S   Y   F   E   I   Y   L   D  140 aag ata agg gac ctg tta gat gtt tca aag acc aac ctt tca gtt cat gaa gac aaa aac  480
 K   I   R   D   L   L   D   V   S   K   T   N   L   S   V   H   E   D   K   N  160 cga gtt ccc tat gta aag ggg tgc aca gag cgt ttt gta tgt agt cca gat gaa gtt atg  540
 R   V   P   Y   V   K   G   C   T   E   R   F   V   C   S   P   D   E   V   M  180 gat acc ata gat gaa gga aaa tcc aac aga cat gta gca gtt aca aat atg aat gaa cat  600
 D   T   I   D   E   G   K   S   N   R   H   V   A   V   T   N   M   N   E   H  200 agc tct agg agt cac agt ata ttt ctt att aat gtc aaa caa gag aac aca caa acg gaa  660
 S   S   R   S   H   S   I   F   L   I   N   V   K   Q   E   N   T   Q   T   E  220 caa aag ctg agt gga aaa ctt tat ctg gtt gat tta gct ggt agt gaa aag gtt agt aaa  720
 Q   K   L   S   G   K   L   Y   L   V   D   L   A   G   S   E   K   V   S   K  240 act gga gct gaa ggt gct gtg ctg gat gaa gct aaa aac atc aac aag tca ctt tct gct  780
 T   G   A   E   G   A   V   L   D   E   A   K   N   I   N   K   S   L   S   A  260 ctt gga aat gtt att tct gct ttg gct gag ggt agt aca tat gtt cca tat cga gat agt  840
 L   G   N   V   I   S   A   L   A   E   G   S   T   Y   V   P   Y   R   D   S  280
```

Fig. 3A

```
aaa atg aca aga atc ctt caa gat tca tta ggt ggc aac tgt aga acc act att gta att  900
 K   M   T   R   I   L   Q   D   S   L   G   G   N   C   R   T   T   I   V   I  300 tgc tgc tct cca tca tca tac aat gag tct gaa aca aaa tct aca ctc tta ttt ggc caa  960
 C   C   S   P   S   S   Y   N   E   S   E   T   K   S   T   L   L   F   G   Q  320 agg gcc aaa aca att aag aac aca gtt tgt gtc aat gtg gag tta act gca gaa cag tgg 1020
 R   A   K   T   I   K   N   T   V   C   V   N   V   E   L   T   A   E   Q   W  340 aaa aag aag tat gaa aaa gaa aaa gaa aaa aat aag atc ctg cgg aac act att cag tgg 1080
 K   K   K   Y   E   K   E   K   E   K   N   K   I   L   R   N   T   I   Q   W  360 ctt gaa aat gag ctc aac aga tgg cgt aat ggg gag acg gtg cct att gat gaa cag ttt 1140
 L   E   N   E   L   N   R   W   R   N   G   E   T   V   P   I   D   E   Q   F  380 gac aaa gag aaa gcc aac ttg gaa gct ttc aca gtg gat aaa gat att act ctt acc aat 1200
 D   K   E   K   A   N   L   E   A   F   T   V   D   K   D   I   T   L   T   N  400 gat aaa cca gca acc gca att gga gtt ata gga aat ttt act gat gct gaa aga aga aag 1260
 D   K   P   A   T   A   I   G   V   I   G   N   F   T   D   A   E   R   R   K  420 tgt gaa gaa gaa att gct aaa tta tac aaa cag ctt gat gac aag gat gaa gaa att aac 1320
 C   E   E   E   I   A   K   L   Y   K   Q   L   D   D   K   D   E   E   I   N  440 cag caa agt caa ctg gta gag aaa ctg aag acg caa atg ttg gat cag gag gag ctt ttg 1380
 Q   Q   S   Q   L   V   E   K   L   K   T   Q   M   L   D   Q   E   E   L   L  460 gca tct acc aga agg gat caa gac aat atg caa gct gag ctg aat cgc ctt caa gca gaa 1440
 A   S   T   R   R   D   Q   D   N   M   Q   A   E   L   N   R   L   Q   A   E  480 aat gat gcc tct aaa gaa gaa gtg aaa gaa gtt tta cag gcc cta gaa gaa ctt gct gtc 1500
 N   D   A   S   K   E   E   V   K   E   V   L   Q   A   L   E   E   L   A   V  500 aat tat gat cag aag tct cag gaa gtt gaa gac aaa act aag gaa tat gaa ttg ctt agt 1560
 N   Y   D   Q   K   S   Q   E   V   E   D   K   T   K   E   Y   E   L   L   S  520 gat gaa ttg aat cag aaa tcg gca act tta gcg agt ata gat gct gag ctt cag aaa ctt 1620
 D   E   L   N   Q   K   S   A   T   L   A   S   I   D   A   E   L   Q   K   L  540 aag gaa atg acc aac cac cag aaa aaa cga gca gct gag atg atg gca tct tta cta aaa 1680
 K   E   M   T   N   H   Q   K   K   R   A   A   E   M   M   A   S   L   L   K  560 gac ctt gca gaa ata gga att gct gtg gga aat aat gat gta aag gag gat cca aag tgg 1740
 D   L   A   E   I   G   I   A   V   G   N   N   D   V   K   E   D   P   K   W  580
```

Fig. 3B

```
gaa ttc cct cgg aag aac ttg gtt ctt gga aaa act cta gga gaa ggc gaa ttt gga aaa   1800
 E   F   P   R   K   N  [ L   V   L   G   K   T   L   G   E   G   E   F   G   K]  600 gtg gtc aag gca acg gcc ttc cat ctg aaa ggc aga gca ggg tac acc acg gtg gcc gtg   1860
[ V   V   K   A   T   A   F   H   L   K   G   R   A   G   Y   T   T   V   A   V]  620 aag atg ctg aaa gag aac gcc tcc ccg agt gag ctg cga gac ctg ctg tca gag ttc aac   1920
[ K   M   L   K   E   N   A   S   P   S   E   L   R   D   L   L   S   E   F   N]  640 gtc ctg aag cag gtc aac cac cca cat gtc atc aaa ttg tat ggg gcc tgc agc cag gat   1980
[ V   L   K   Q   V   N   H   P   H   V   I   K   L   Y   G   A   C   S   Q   D]  660 ggc ccg ctc ctc ctc atc gtg gag tac gcc aaa tac ggc tcc ctg cgg ggc ttc ctc cgc   2040
[ G   P   L   L   L   I   V   E   Y   A   K   Y   G   S   L   R   G   F   L   R]  680 gag agc cgc aaa gtg ggg cct ggc tac ctg ggc agt gga ggc agc cgc aac tcc agc tcc   2100
[ E   S   R   K   V   G   P   G   Y   L   G   S   G   G   S   R   N   S   S   S]  700 ctg gac cac ccg gat gag cgg gcc ctc acc atg ggc gac ctc atc tca ttt gcc tgg cag   2160
[ L   D   H   P   D   E   R   A   L   T   M   G   D   L   I   S   F   A   W   Q]  720 atc tca cag ggg atg cag tat ctg gcc gag atg aag ctc gtt cat cgg gac ttg gca gcc   2220
[ I   S   Q   G   M   Q   Y   L   A   E   M   K   L   V   H   R   D   L   A   A]  740 aga aac atc ctg gta gct gag ggg cgg aag atg aag att tcg gat ttc ggc ttg tcc cga   2280
[ R   N   I   L   V   A   E   G   R   K   M   K   I   S   D   F   G   L   S   R]  760 gat gtt tat gaa gag gat tcc tac gtg aag agg agc cag ggt cgg att cca gtt aaa tgg   2340
[ D   V   Y   E   E   D   S   Y   V   K   R   S   Q   G   R   I   P   V   K   W]  780 atg gca att gaa tcc ctt ttt gat cat atc tac acc acg caa agt gat gta tgg tct ttt   2400
[ M   A   I   E   S   L   F   D   H   I   Y   T   T   Q   S   D   V   W   S   F]  800 ggt gtc ctg ctg tgg gag atc gtg acc cta ggg gga aac ccc tat cct ggg att cct cct   2460
[ G   V   L   L   W   E   I   V   T   L   G   G   N   P   Y   P   G   I   P   P]  820 gag cgg ctc ttc aac ctt ctg aag acc ggc cac cgg atg gag agg cca gac aac tgc agc   2520
[ E   R   L   F   N   L   L   K   T   G   H   R   M   E   R   P   D   N   C   S]  840 gag gag atg tac cgc ctg atg ctg caa tgc tgg aag cag gag ccg gac aaa agg ccg gtg   2580
[ E   E   M   Y   R   L   M   L   Q   C   W   K   Q   E   P   D   K   R   P   V]  860 ttt gcg gac atc agc aaa gac ctg gag aag atg atg gtt aag agg aga gac tac ttg gac   2640
[ F   A   D   I   S   K   D   L]  E   K   M   M   V   K   R   R   D   Y   L   D   880
```

Fig. 3C

```
ctt gcg gcg tcc act cca tct gac tcc ctg att tat gac gac ggc ctc tca gag gag gag  2700
 L   A   A   S   T   P   S   D   S   L   I   Y   D   D   G   L   S   E   E   E   900 aca ccg ctg gtg gac tgt aat aat gcc ccc ctc cct cga gcc ctc cct tcc aca tgg att  2760
 T   P   L   V   D   C   N   N   A   P   L   P   R   A   L   P   S   T   W   I   920 gaa aac aaa ctc tat ggc atg tca gac ccg aac tgg cct gga gag agt cct gta cca ctc  2820
 E   N   K   L   Y   G   M   S   D   P   N   W   P   G   E   S   P   V   P   L   940 acg aga gct gat ggc act aac act ggg ttt cca aga tat cca aat gat agt gta tat gct  2880
 T   R   A   D   G   T   N   T   G   F   P   R   Y   P   N   D   S   V   Y   A   960 aac tgg atg ctt tca ccc tca gcg gca aaa tta atg gac acg ttt gat agt taa  2934
 N   W   M   L   S   P   S   A   A   K   L   M   D   T   F   D   S   *   977
``` cDNA = SEQ ID NO:1
protein = SEQ ID NO:2

Fig. 3D

```
atg gcg aag gcg acg tcc ggt gcc gcg ggg ctg cgt ctg ctg ttg ctg ctg ctg ccg   60
 M   A   K   A   T   S   G   A   A   G   L   R   L   L   L   L   L   L   P   20 ctg cta ggc aaa gtg gca ttg ggc ctc tac ttc tcg agg gat gct tac tgg gag aag ctg  120
 L   L   G   K   V   A   L   G   L   Y   F   S   R   D   A   Y   W   E   K   L   40 tat gtg gac cag gca gcc ggc acg ccc ttg ctg tac gtc cat gcc ctg cgg gac gcc cct  180
 Y   V   D   Q   A   A   G   T   P   L   L   Y   V   H   A   L   R   D   A   P   60 gag gag gtg ccc agc ttc cgc ctg ggc cag cat ctc tac ggc acg tac cgc aca cgg ctg  240
 E   E   V   P   S   F   R   L   G   Q   H   L   Y   G   T   Y   R   T   R   L   80 cat gag aac aac tgg atc tgc atc cag gag gac acc ggc ctc ctc tac ctt aac cgg agc  300
 H   E   N   N   W   I   C   I   Q   E   D   T   G   L   L   Y   L   N   R   S  100 ctg gac cat agc tcc tgg gag aag ctc agt gtc cgc aac cgc ggc ttt ccc ctg ctc acc  360
 L   D   H   S   S   W   E   K   L   S   V   R   N   R   G   F   P   L   L   T  120 gtc tac ctc aag gtc ttc ctg tca ccc aca tcc ctt cgt gag ggc gag tgc cag tgg cca  420
 V   Y   L   K   V   F   L   S   P   T   S   L   R   E   G   E   C   Q   W   P  140 ggc tgt gcc cgc gta tac ttc tcc ttc ttc aac acc tcc ttt cca gcc tgc agc tcc ctc  480
 G   C   A   R   V   Y   F   S   F   F   N   T   S   F   P   A   C   S   S   L  160 aag ccc cgg gag ctc tgc ttc cca gag aca agg ccc tcc ttc cgc att cgg gag aac cga  540
 K   P   R   E   L   C   F   P   E   T   R   P   S   F   R   I   R   E   N   R  180 ccc cca ggc acc ttc cac cag ttc cgc ctg ctg cct gtg cag ttc ttg tgc ccc aac atc  600
 P   P   G   T   F   H   Q   F   R   L   L   P   V   Q   F   L   C   P   N   I  200 agc gtg gcc tac agg ctc ctg gag ggt gag ggt ctg ccc ttc cgc tgc gcc ccg gac agc  660
 S   V   A   Y   R   L   L   E   G   E   G   L   P   F   R   C   A   P   D   S  220 ctg gag gtg agc acg cgc tgg gcc ctg gac cgc gag cag cgg gag aag tac gag ctg gtg  720
 L   E   V   S   T   R   W   A   L   D   R   E   Q   R   E   K   Y   E   L   V  240 gcc gtg tgc acc gtg cac gcc ggc gcg cgc gag gag gtg gtg atg gtg ccc ttc ccg gtg  780
 A   V   C   T   V   H   A   G   A   R   E   E   V   V   M   V   P   F   P   V  260 acc gtg tac gac gag gac gac tcg gcg ccc acc ttc ccc gcg ggc gtc gac acc gcc agc  840
 T   V   Y   D   E   D   D   S   A   P   T   F   P   A   G   V   D   T   A   S  280 gcc gtg gtg gag ttc aag cgg aag gag gac acc gtg gtg gcc acg ctg cgt gtc ttc gat  900
 A   V   V   E   F   K   R   K   E   D   T   V   V   A   T   L   R   V   F   D  300
```

Fig. 4A

```
gca gac gtg gta cct gca tca ggg gag ctg gtg agg cgg tac aca agc acg ctg ctc ccc 960
 A   D   V   V   P   A   S   G   E   L   V   R   R   Y   T   S   T   L   L   P 320 ggg gac acc tgg gcc cag cag acc ttc cgg gtg gaa cac tgg ccc aac gag acc tcg gtc 1020
 G   D   T   W   A   Q   Q   T   F   R   V   E   H   W   P   N   E   T   S   V 340 cag gcc aac ggc agc ttc gtg cgg gcg acc gta cat gac tat agg ctg gtt ctc aac cgg 1080
 Q   A   N   G   S   F   V   R   A   T   V   H   D   Y   R   L   V   L   N   R 360 aac ctc tcc atc tcg gag aac cgc acc atg cag ctg gcg gtg ctg gtc aat gac tca gac 1140
 N   L   S   I   S   E   N   R   T   M   Q   L   A   V   L   V   N   D   S   D 380 ttc cag ggc cca gga gcg ggc gtc ctc ttg ctc cac ttc aac gtg tcg gtg ctg ccg gtc 1200
 F   Q   G   P   G   A   G   V   L   L   L   H   F   N   V   S   V   L   P   V 400 agc ctg cac ctg ccc agt acc tac tcc ctc tcc gtg agc agg agg gct cgc cga ttt gcc 1260
 S   L   H   L   P   S   T   Y   S   L   S   V   S   R   R   A   R   R   F   A 420 cag atc ggg aaa gtc tgt gtg gaa aac tgc cag gca ttc agt ggc atc aac gtc cag tac 1320
 Q   I   G   K   V   C   V   E   N   C   Q   A   F   S   G   I   N   V   Q   Y 440 aag ctg cat tcc tct ggt gcc aac tgc agc acg cta ggg gtg gtc acc tca gcc gag gac 1380
 K   L   H   S   S   G   A   N   C   S   T   L   G   V   V   T   S   A   E   D 460 acc tcg ggg atc ctg ttt gtg aat gac acc aag gcc ctg cgg cgg ccc aag tgt gcc gaa 1440
 T   S   G   I   L   F   V   N   D   T   K   A   L   R   R   P   K   C   A   E 480 ctt cac tac atg gtg gtg gcc acc gac cag cag acc tct agg cag gcc cag gcc cag ctg 1500
 L   H   Y   M   V   V   A   T   D   Q   Q   T   S   R   Q   A   Q   A   Q   L 500 ctt gta aca gtg gag ggg tca tat gtg gcc gag gag gcg ggc tgc ccc ctg tcc tgt gca 1560
 L   V   T   V   E   G   S   Y   V   A   E   E   A   G   C   P   L   S   C   A 520 gtc agc aag aga cgg ctg gag tgt gag gag tgt ggc ggc ctg ggc tcc cca aca ggc agg 1620
 V   S   K   R   R   L   E   C   E   E   C   G   G   L   G   S   P   T   G   R 540 tgt gag tgg agg caa gga gat ggc aaa ggg atc acc agg aac ttc tcc acc tgc tct ccc 1680
 C   E   W   R   Q   G   D   G   K   G   I   T   R   N   F   S   T   C   S   P 560 agc acc aag acc tgc ccc gac ggc cac tgc gat gtt gtg gag acc caa gac atc aac att 1740
 S   T   K   T   C   P   D   G   H   C   D   V   V   E   T   Q   D   I   N   I 580 tgc cct cag gac tgc ctc cgg ggc agc att gtt ggg gga cac gag cct ggg gag ccc cgg 1800
 C   P   Q   D   C   L   R   G   S   I   V   G   G   H   E   P   G   E   P   R 600
```

Fig. 4B

```
ggg att aaa gct ggc tat ggc acc tgc aac tgc ttc cct gag gag gag aag tgc ttc tgc 1860
 G   I   K   A   G   Y   G   T   C   N   C   F   P   E   E   E   K   C   F   C  620 gag ccc gaa gac atc cag gat cca ctg tgc gac gag ctg tgc cgc acg gtg atc gca gcc 1920
 E   P   E   D   I   Q   D   P   L   C   D   E   L   C   R   T   V   I   A   A  640 gct gtc ctc ttc tcc ttc atc gtc tcg gtg ctg ctg tct gcc ttc tgc atc cac tgc tac 1980
 A   V   L   F   S   F   I   V   S   V   L   L   S   A   F   C   I   H   C   Y  660 cac aag ttt gcc cac aag cca ccc atc tcc tca gct gag atg acc ttc cgg agg ccc gcc 2040
 H   K   F   A   H   K   P   P   I   S   S   A   E   M   T   F   R   R   P   A  680 cag gcc ttc ccg gtc agc tac tcc tct tcc ggt gcc cgc cgg ccc tcg ctg gac tcc atg 2100
 Q   A   F   P   V   S   Y   S   S   S   G   A   R   R   P   S   L   D   S   M  700 gag aac cag gtc tcc gtg gat gcc ttc aag atc ctg cag cct gag gga act ggc atg ata 2160
 E   N   Q   V   S   V   D   A   F   K   I   L   Q   P   E   G   T   G   M   I  720 gat gaa gag ttc act gtt gca aga ctc tac att agc aaa atg aag tca gaa gta aaa acc 2220
 D   E   E   F   T   V   A   R   L   Y   I   S   K   M   K   S   E   V   K   T  740 atg gtg aaa cgt tgc aag cag tta gaa agc aca caa act gag agc aac aaa aaa atg gaa 2280
 M   V   K   R   C   K   Q   L   E   S   T   Q   T   E   S   N   K   K   M   E  760 gaa aat gaa aag gag tta gca gca tgt cag ctt cgt atc tct caa cat gaa gcc aaa atc 2340
 E   N   E   K   E   L   A   A   C   Q   L   R   I   S   Q   H   E   A   K   I  780 aag tca ttg act gaa tac ctt caa aat gtg gaa caa aag aaa aga cag ttg gag gaa tct 2400
 K   S   L   T   E   Y   L   Q   N   V   E   Q   K   K   R   Q   L   E   E   S  800 gtc gat gcc ctc agt gaa gaa cta gtc cag ctt cga gca caa gag aaa gtc cat gaa atg 2460
 V   D   A   L   S   E   E   L   V   Q   L   R   A   Q   E   K   V   H   E   M  820 gaa aag gag cac tta aat aag gtt cag act gca aat gaa gtt aag caa gct gtt gaa cag 2520
 E   K   E   H   L   N   K   V   Q   T   A   N   E   V   K   Q   A   V   E   Q  840 cag atc cag agc cat aga gaa act cat caa aaa cag atc agt agt ttg aga gat gaa gta 2580
 Q   I   Q   S   H   R   E   T   H   Q   K   Q   I   S   S   L   R   D   E   V  860 gaa gca aaa gca aaa ctt att act gat ctt caa gac caa aac cag aaa atg atg tta gag 2640
 E   A   K   A   K   L   I   T   D   L   Q   D   Q   N   Q   K   M   M   L   E  880
```

Fig. 4C

```
cag gaa cgt cta aga gta gaa cat gag aag ttg aaa gcc aca gat cag gaa aag agc aga 2700
 Q   E   R   L   R   V   E   H   E   K   L   K   A   T   D   Q   E   K   S   R 900 aaa cta cat gaa ctt acg gtt atg caa gat aga cga gaa caa gca aga caa gac ttg aag 2760
 K   L   H   E   L   T   V   M   Q   D   R   R   E   Q   A   R   Q   D   L   K 920 ggt ttg gaa gag aca gtg gca aaa gaa ctt cag act tta cac aac ctg cgc aaa ctc ttt 2820
 G   L   E   E   T   V   A   K   E   L   Q   T   L   H   N   L   R   K   L   F 940 gtt cag gac ctg gct aca aga gtt aaa aag agt gct gag att gat tct gat gac acc gga 2880
 V   Q   D   L   A   T   R   V   K   K   S   A   E   I   D   S   D   D   T   G 960 ggc agc gct gct cag aag caa aaa atc tcc ttt ctt gaa aat aat ctt gaa cag ctc act 2940
 G   S   A   A   Q   K   Q   K   I   S   F   L   E   N   N   L   E   Q   L   T 980 aaa gtg cac aaa cag ttg gta cgt gat aat gca gat ctc cgc tgt gaa ctt cct aag ttg 3000
 K   V   H   K   Q   L   V   R   D   N   A   D   L   R   C   E   L   P   K   L 1000 gaa aag cga ctt cga gct aca gct gag aga gtg aaa gct ttg gaa tca gca ctg aaa gaa 3060
 E   K   R   L   R   A   T   A   E   R   V   K   A   L   E   S   A   L   K   E 1020 gct aaa gaa aat gca tct cgt gat cgc aaa cgc tat cag caa gaa gta gat cgc ata aag 3120
 A   K   E   N   A   S   R   D   R   K   R   Y   Q   Q   E   V   D   R   I   K 1040 gaa gca gtc agg tca aag aat atg gcc aga aga ggg cat tct gca cag att gct aaa cct 3180
 E   A   V   R   S   K   N   M   A   R   R   G   H   S   A   Q   I   A   K   P 1060 att cgt ccc ggg caa cat cca gca gct tct cca act cac cca agt gca att cgt gga gga 3240
 I   R   P   G   Q   H   P   A   A   S   P   T   H   P   S   A   I   R   G   G 1080 ggt gca ttt gtt cag aac agc cag cca gtg gca gtg cga ggt gga gga ggc aaa caa gtg 3300
 G   A   F   V   Q   N   S   Q   P   V   A   V   R   G   G   G   K   Q   V 1100 taa       3360    SEQ ID NO:3
 *                SEQ ID NO:4
```

Fig. 4D

1     MADLAECNIKVMCRFRPLNESEVNRGDKYIAKFQGEDTVVIASKPYAFDRVFQSSTSQEQ
61    VYNDCAKKIVKDVLEGYNGTIFAYGQTSSGKTHTMEGKLHDPEGMGIIPRIVQDIFNYIY
121   SMDENLEFHIKVSYFEIYLDKIRDLLDVSKTNLSVHEDKNRVPYVKGCTERFVCSPDEVM
181   DTIDEGKSNRHVAVTNMNEHSSRSHSIFLINVKQENTQTEQKLSGKLYLVDLAGSEKVSK
241   TGAEGAVLDEAKNINKSLSALGNVISALAEGSTYVPYRDSKMTRILQDSLGGNCRTTII
301   CCSPSSYNESETKSTLLFGQRAKTIKNTVCVNVELTAEQWKKKYEKEKENKILRNTIQW
361   LENELNRWRNGETVPIDEQFDKEKANLEAFTVDKDITLTNDKPATAIGVIGNFTDAERRK
421   CEEEIAKLYKQLDDKDEEINQQSQLVEKLKTQMLDQEELLASTRRDQDNMQAELNRLQAE
481   NDASKEEVKEVLQALEELAVNYDQKSQEVEDKTKEYELLSDELNQKSATLASIDAELQKL
541   KEMTNHQKKRAAEMMASLLKDLAEIGIAVGNNDVKEDPKWEFPRKNLVLGKTLGEGEFGK
601   VVKATAPHLKGRAGYTTVAVKMLKENASPSELRDLLSEFNVLKQVNHPHVIKLYGACSQD
661   GPLLLIVEYAKYGSLRGFLRESRKVGPGYLGSGGSRNSSSLDHPDERALTMGDLISFAWQ
721   ISQGMQYLAEMKLVHRDLAARNILVAEGRKMKISDFGLSRDVYEEDSYVKRSQGRIPVKW
781   MAIESLFDHIYTTQSDVWSFGVLLWEIVTLGGNPYPGIPPERLFNLLKTGHRMERPDNCS
841   EEMYRLMLQCWKQEPDKRPVFADISKDLEKMMVKRRDYLDLAASTPSDSLIYDDGLSEEE
901   TPLVDCNNAPLPRALPSTWIENKLYGMSDPNWPGESPVPLTRADGTNTGFPRYPNDSVYA
961   NWMLSPSAAKLMDTFDS

Fig. 7B

KIF5B-RET FUSION MOLECULES AND USES THEREOF

RELATED APPLICATIONS

This application is a divisional of U.S. application Ser. No. 14/187,280, filed Feb. 23, 2014, now allowed, which is a continuation of International Application No. PCT/US2012/051978, filed Aug. 23, 2012, which claims the benefit of U.S. Provisional Application No. 61/526,613, filed Aug. 23, 2011; U.S. Provisional Application No. 61/537,024, filed Sep. 20, 2011; U.S. Provisional Application No. 61/542,112, filed Sep. 30, 2011; and U.S. Provisional Application No. 61/594,739, filed Feb. 3, 2012. The contents of all these prior applications are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Feb. 17, 2016, is named F2036-702540 Sequence Listing.txt and is 59,049 bytes in size.

BACKGROUND

Cancer represents the phenotypic end-point of multiple genetic lesions that endow cells with a full range of biological properties required for tumorigenesis. Indeed, a hallmark genomic feature of many cancers, including, for example, B cell cancer, lung cancer, breast cancer, ovarian cancer, pancreatic cancer, and colon cancer, is the presence of numerous complex chromosome structural aberrations, including translocations, intra-chromosomal inversions, point mutations, deletions, gene copy number changes, gene expression level changes, and germline mutations, among others.

The need still exists for identifying novel genetic lesions associated with cancer. Such genetic lesions can be an effective approach to develop compositions, methods and assays for evaluating and treating cancer patients.

SUMMARY

The invention is based, at least in part, on the discovery of novel inversion events that include a fragment of a KIF5B gene ("Kinesin Family Member 5B-RET proto-oncogene") and a fragment of a RET proto-oncogene in a cancer, e.g., a lung cancer, referred to herein as "KIF5B-RET." The term "KIF5B-RET" or "KIF5B-RET fusion" is used generically herein, and includes any fusion molecule (e.g., gene, gene product (e.g., cDNA, mRNA, or polypeptide), and variant thereof) that includes a fragment of KIF5B and a fragment of RET, including, e.g., a 5'KIF5B-3'RET.

In one embodiment, a KIF5B-RET fusion includes an in-frame fusion of an exon of KIF5B (e.g., one more exons encoding a kinesin motor domain or a fragment thereof) and an exon of RET (e.g., one or more exons encoding a RET tyrosine kinase domain or a fragment thereof). For example, the KIF5B-RET fusion can include an in-frame fusion of at least exon 15 of KIF5B or a fragment thereof (e.g., exons 1-15 of KIF5B or a fragment thereof) with at least exon 12 of RET or a fragment thereof (e.g., exons 12-20 of RET or a fragment thereof). In certain embodiments, the KIF5B-RET fusion is in a 5'-KIF5B to 3'-RET configuration referred to herein as "5'KIF5B-3'RET." A KIF5B-RET fusion polypeptide encoded by a 5'KIF5B-3'RET nucleic acid is sometimes referred to herein as a 5'KIF5B-3'RET polypeptide. In an embodiment, the 5'KIF5B-3'RET fusion comprises sufficient KIF5B and sufficient RET sequence such that the 5'KIF5B-3'RET fusion has kinase activity, e.g., has elevated activity, e.g., kinase activity, as compared with wild type RET, e.g., in a cell of a cancer referred to herein. In one embodiment, the 5'KIF5B-3'RET fusion comprises at least 1, 2, 3, 4, 5, 6, 7, 9, 10, or 11 exons from KIF5B and at least 1, 2, 3, 4, 5, 6, 7, 9, or 10, RET exons. In one embodiment, the 5'KIF5B-3'RET fusion polypeptide includes a kinesin motor domain, a coiled coil domain, or a functional fragment thereof, and a RET tyrosine kinase domain or a functional fragment thereof.

The RET proto-oncogene is associated with cancerous phenotypes, including papillary thyroid carcinomas (PTC), multiple endocrine neoplasias (MEN), phaeochromocytoma, among others. For example, chromosomal rearrangements that generate a fusion gene resulting in the juxtaposition of the C-terminal region of the RET protein with an N-terminal portion of another protein (known as RET/PTC) are known to be associated with PTC (Nikiforov, Y E (2002) *Endocr. Pathol.* 13 (1):3-16). The RET/PTC has been shown to cause constitute activation of the RET kinase domain, which is a likely contributor to tumorigenicity. The KIF5B-RET fusions disclosed herein (e.g., the 5'-KIF5B to 3'-RET fusions that include a RET tyrosine kinase domain) are associated with cancers, e.g., lung cancer. Elevated expression of the 3' end of RET beginning in exon 12 is detected in lung tumor samples, suggesting that the KIF5B-RET fusion transcript can result in RET kinase domain overexpression.

In other embodiments, the KIF5B-RET fusion includes an in-frame fusion of at least exon 11 of RET or a fragment thereof (e.g., exons 1-11 of RET or a fragment thereof) with at least exon 16 or a fragment thereof (e.g., exons 16-25 of KIF5B or a fragment thereof). In certain embodiments, the KIF5B-RET fusion is in a 5'-RET to 3'-KIF5B configuration referred to herein as "5'RET-3'KIF5B"). The 5'RET-3'KIF5B configuration of the fusion molecule is not believed to be expressed.

Accordingly, the invention provides, methods of: identifying, assessing or detecting a KIF5B-RET fusion; methods of identifying, assessing, evaluating, and/or treating a subject having a cancer, e.g., a cancer having a KIF5B-RET fusion; isolated KIF5B-RET nucleic acid molecules, nucleic acid constructs, host cells containing the nucleic acid molecules; purified KIF5B-RET polypeptides and binding agents; detection reagents (e.g., probes, primers, antibodies, kits, capable, e.g., of specific detection of a KIF5B-RET nucleic acid or protein); screening assays for identifying molecules that interact with, e.g., inhibit, 5'KIF5B-3'RET fusions, e.g., novel kinase inhibitors; as well as assays and kits for evaluating, identifying, assessing and/or treating a subject having a cancer, e.g., a cancer having a KIF5B-RET fusion. The compositions and methods identified herein can be used, for example, to identify new KIF5B-RET inhibitors; to evaluate, identify or select subject, e.g., a patient, having a cancer; and to treat or prevent a cancer.

KIF5B-RET Nucleic Acid Molecules

In one aspect, the invention features a nucleic acid molecule (e.g., an isolated or purified) nucleic acid molecule that includes a fragment of a KIF5B gene and a fragment of a RET proto-oncogene. In one embodiment, the nucleic acid molecule includes a fusion, e.g., an in-frame fusion, of an exon of KIF5B (e.g., one more exons encoding a kinesin motor domain or a fragment thereof), and an exon of RET (e.g., one or more exons encoding a RET tyrosine kinase domain or a fragment thereof).

In an embodiment the 5'KIF5B-3'RET nucleic acid molecule comprises sufficient KIF5B and sufficient RET sequence such that the encoded 5'KIF5B-3'RET fusion has kinase activity, e.g., has elevated activity, e.g., kinase activity, as compared with wild type RET, e.g., in a cell of a cancer referred to herein. In an embodiment the encoded 5'KIF5B-3'RET fusion comprises at least 1, 2, 3, 4, 5, 6, 7, 9, 10, or 11 exons from KIF5B and at least 1, 2, 3, 4, 5, 6, 7, 9, or 10, RET exons. In one embodiment, the encoded 5'KIF5B-3'RET fusion polypeptide includes a kinesin motor domain, a coiled coil domain, or a functional fragment thereof, and a RET tyrosine kinase domain or a functional fragment thereof.

In one embodiment, the nucleic acid molecule includes a nucleotide sequence that has an in-frame fusion of exon 15 of KIF5B with exon 12 of RET (e.g., a sequence within an 11 MB pericentric inversion on chromosome 10). In other embodiments, the nucleic acid molecules includes a nucleotide sequence in the region of 32,316,376-32,316,416 of chromosome 10 coupled to (e.g., juxtaposed to) nucleotides in the region of nucleotides 43,611,042-43,611,118 of chromosome 10. In another embodiment, the nucleic acid molecule includes a nucleotide sequence that includes a breakpoint, e.g., a breakpoint identified in FIGS. 1, 2 and 3A-3D. For example, the nucleic acid molecule includes a nucleotide sequence that includes the fusion junction between the KIF5B transcript and the RET transcript, e.g., a nucleotide sequence that includes a portion of SEQ ID NO:1 (e.g., a nucleotide sequence within exons 1-15 of a KIF5B gene and 12-20 of a RET gene) (e.g., a portion of SEQ ID NO:1 comprising nucleotides 1720-1731, 1717-1734, or 1714-1737 of SEQ ID NO:1 (see FIG. 3B)).

In other embodiments, the nucleic acid molecule includes a KIF5B-RET fusion having a configuration shown in FIGS. 2B and 3A-3D. For example, the KIF5B-RET fusion can include an in-frame fusion of at least exon 15 of KIF5B or a fragment thereof (e.g., exons 1-15 of KIF5B or a fragment thereof) with at least exon 12 of RET or a fragment thereof (e.g., exons 12-20 of RET or a fragment thereof). In certain embodiments, the KIF5B-RET fusion is in a 5'-KIF5B to 3'-RET configuration referred to herein as "5'KIF5B-3'RET"). In one embodiment, the nucleic acid molecule includes the nucleotide sequence of nucleotides 1-1725 of SEQ ID NO:1 (corresponding to exons 1-15 of the KIF5B gene), or a fragment thereof, or a sequence substantially identical thereto. In another embodiment, the nucleic acid molecule includes the nucleotide sequence of nucleotides 1726-2934 of SEQ ID NO:1 (e.g., corresponding to exons 12-20 of the RET gene), or a fragment thereof, or a sequence substantially identical thereto. In yet other embodiments, the nucleic acid molecule includes the nucleotide sequence shown in FIGS. 3A-3D (e.g., SEQ ID NO:1) or a fragment thereof, or a sequence substantially identical thereto. In one embodiment, the nucleic acid molecule is complementary to at least a portion of a nucleotide sequence disclosed herein, e.g., is capable of hybridizing under a stringency condition described herein to SEQ ID NO:1 or a fragment thereof. In yet other embodiment, the nucleic acid molecule hybridizes to a nucleotide sequence that is complementary to at least a portion of a nucleotide sequence disclosed herein, e.g., is capable of hybridizing under a stringency condition described herein to a nucleotide sequence complementary to SEQ ID NO:1 or a fragment thereof. The nucleotide sequence of a cDNA encoding an exemplary 5'KIF5B-3'RET fusion is shown in SEQ ID NO:1, and the amino acid sequence is shown in SEQ ID NO:2.

In other embodiments, the nucleic acid molecule includes a nucleotide sequence encoding a KIF5B-RET fusion polypeptide that includes a fragment of a KIF5B gene and a fragment of a RET proto-oncogene. In one embodiment, the nucleotide sequence encodes a KIF5B-RET fusion polypeptide that includes a kinesin motor domain or a functional fragment thereof, and a RET tyrosine kinase domain or a functional fragment thereof. In another embodiment, the nucleotide sequence encodes a fragment of the KIF5B polypeptide including the amino acid sequence of amino acids 1-575 of SEQ ID NO:2 or a fragment thereof, or a sequence substantially identical thereto. For example, the nucleic acid molecule can include a nucleotide sequence encoding a kinesin motor domain of KIF5B-RET fusion polypeptide that includes amino acids 6-325 of SEQ ID NO:2 or a fragment thereof. In other embodiments, the nucleic acid molecule includes a fragment of the RET gene encoding the amino acid sequence of amino acids 576-977 of SEQ ID NO:2 or a fragment thereof, or a sequence substantially identical thereto. For example, the nucleic acid molecule can include a nucleotide sequence encoding a RET kinase domain of a KIF5B-RET fusion polypeptide that includes amino acids 587-868 of SEQ ID NO:2 or a fragment thereof. In yet other embodiments, the nucleic acid molecule includes a nucleotide sequence encoding the amino acid sequence shown in FIGS. 3A-3D (e.g., SEQ ID NO:2) or a fragment thereof, or a sequence substantially identical thereto.

In another embodiment, the nucleic acid molecule includes a KIF5B-RET fusion having the configuration shown in FIGS. 2A and 4A-4D. In one embodiment, the nucleic acid molecule includes a nucleotide sequence that include a fusion junction between the RET transcript and the KIF5B transcript, e.g., a nucleotide sequence within SEQ ID NO:3 (e.g., a sequence comprising nucleotides 2131-2142, 2128-2145, or 2125-2148 of SEQ ID NO:3 (see FIG. 4B)). In another embodiment, the nucleic acid molecule includes a fusion, e.g., an in-frame fusion, of at least exon 11 of RET or a fragment thereof (e.g., exons 1-11 of RET or a fragment thereof), and at least exon 16 or a fragment thereof (e.g., exons 16-25 of KIF5B or a fragment thereof). In certain embodiments, the KIF5B-RET fusion is in a 5'-RET to 3'-KIF5B configuration referred to herein as "5'RET-3'KIF5B"). In one embodiment, the nucleic acid molecule includes the nucleotides sequence of 1-2136 of SEQ ID NO:3 (corresponding to exons 1-11 of a RET gene) or a fragment thereof, or a sequence substantially identical thereto. In another embodiment, the nucleic acid molecule includes the nucleotides sequence of 2137-3360 of SEQ ID NO:3 (corresponding to exons 16-25 of the a KIF5B gene) or a fragment thereof, or a sequence substantially identical thereto. In yet other embodiments, the nucleic acid molecule includes the nucleotide sequence shown in FIGS. 4A-4D (e.g., SEQ ID NO:3) or a fragment thereof, or a sequence substantially identical thereto. In one embodiment, the nucleic acid molecule is complementary to at least a portion of a nucleotide sequence disclosed herein, e.g., is capable of hybridizing under a stringency condition described herein to SEQ ID NO:3 or a fragment thereof. In yet other embodiment, the nucleic acid molecule hybridizes to a nucleotide sequence that is complementary to at least a portion of a nucleotide sequence disclosed herein, e.g., is capable of hybridizing under a stringency condition to a nucleotide sequence complementary to SEQ ID NO:3 or a fragment thereof. The nucleotide sequence of a cDNA encoding an exemplary 5'RET-3'KIF5B fusion is shown in SEQ ID NO:3, and the predicted amino acid sequence is shown in SEQ ID NO:4. RT-PCR studies have shown that the RET exon 11 and KIF5B exon 16 did not yield a transcription product.

In a related aspect, the invention features nucleic acid constructs that include the KIF5B-RET nucleic acid molecules described herein. In certain embodiments, the nucleic acid molecules are operatively linked to a native or a heterologous regulatory sequence. Also included are vectors and host cells that include the KIF5B-RET nucleic acid molecules described herein, e.g., vectors and host cells suitable for producing the nucleic acid molecules and polypeptides described herein.

In a related aspect, methods of producing the nucleic acid molecules and polypeptides described herein are also described.

In another aspect, the invention features nucleic acid molecules that reduces or inhibits the expression of a nucleic acid molecule that encodes a KIF5B-RET fusion described herein. Examples of such nucleic acid molecules include, for example, antisense molecules, ribozymes, RNAi, triple helix molecules that hybridize to a nucleic acid encoding KIF5B-RET, or a transcription regulatory region of KIF5B-RET, and blocks or reduces mRNA expression of KIF5B-RET.

Nucleic Acid Detection and Capturing Reagents

The invention also features a nucleic acid molecule, e.g., nucleic acid fragment, suitable as probe, primer, bait or library member that includes, flanks, hybridizes to, which are useful for identifying, or are otherwise based on, the KIF5B-RET fusions described herein. In certain embodiments, the probe, primer or bait molecule is an oligonucleotide that allows capture, detection or isolation of a KIF5B-RET fusion nucleic acid molecule described herein. The oligonucleotide can comprise a nucleotide sequence substantially complementary to a fragment of the KIF5B-RET fusion nucleic acid molecules described herein. The sequence identity between the nucleic acid fragment, e.g., the oligonucleotide, and the target KIF5B-RET sequence need not be exact, so long as the sequences are sufficiently complementary to allow the capture, detection or isolation of the target sequence. In one embodiment, the nucleic acid fragment is a probe or primer that includes an oligonucleotide between about 5 and 25, e.g., between 10 and 20, or 10 and 15 nucleotides in length. In other embodiments, the nucleic acid fragment is a bait that includes an oligonucleotide between about 100 to 300 nucleotides, 130 and 230 nucleotides, or 150 and 200 nucleotides, in length.

In one embodiment, the nucleic acid fragment can be used to identify or capture, e.g., by hybridization, a KIF5B-RET fusion. For example, the nucleic acid fragment can be a probe, a primer, or a bait, for use in identifying or capturing, e.g., by hybridization, a KIF5B-RET fusion described herein. In one embodiment, the nucleic acid fragment can be useful for identifying or capturing a KIF5B-RET breakpoint, e.g., as identified in FIG. 1. In one embodiment, the nucleic acid fragment hybridizes to a nucleotide sequence within a chromosomal rearrangement that creates an in-frame fusion of exon 15 of KIF5B with exon 12 of RET (e.g., a sequence within an 11 MB pericentric inversion on chromosome 10). In one embodiment, the nucleic acid fragment hybridizes to a nucleotide sequence in the region of 32,316,376-32,316,416 of chromosome 10 coupled to (e.g., juxtaposed to) nucleotides in the region of nucleotides 43,611,042-43,611,118 of chromosome 10. In one embodiment, the nucleic acid fragment hybridizes to a nucleotide sequence that includes a breakpoint, e.g., a breakpoint as identified in FIGS. 1, 2 and 3A-3D. For example, the nucleic acid fragment can hybridize to a nucleotide sequence that includes the fusion junction between the KIF5B transcript and the RET transcript, e.g., a nucleotide sequence that includes a portion of SEQ ID NO:1 (e.g., a nucleotide sequence within exons 1-15 of a KIF5B gene and 12-20 of a RET gene) (e.g., a portion of SEQ ID NO:1 comprising nucleotides 1720-1731, 1717-1734, or 1714-1737 of SEQ ID NO:1 (see FIG. 3B)).

The probes or primers described herein can be used, for example, for FISH detection or PCR amplification. In one exemplary embodiment where detection is based on PCR, amplification of the KIF5B-RET fusion junction can be performed using a primer or a primer pair, e.g., for amplifying a sequence flanking the KIF5B-RET fusion junctions described herein, e.g., the mutations or the junction of a chromosomal rearrangement described herein. In one embodiment, a pair of isolated oligonucleotide primers can amplify a region containing or adjacent to a position in the KIF5B-RET fusion. For example, forward primers can be designed to hybridize to a nucleotide sequence within KIF5B genomic or mRNA sequence (e.g., a nucleotide sequence within exons 1-15 of a KIF5B gene, or nucleotides 1-1725 of SEQ ID NO:1), and the reverse primers can be designed to hybridize to a nucleotide sequence within RET (e.g., a nucleotide sequence within exons 12-20 of RET, or nucleotides 1725-2934 of SEQ ID NO:1).

In another embodiment, the nucleic acid fragments can be used to identify, e.g., by hybridization, a 5'RET-3'KIF5B fusion. In one embodiment, the nucleic acid fragment hybridizes to a nucleotide sequence that include a fusion junction between the RET transcript and the KIF5B transcript, e.g., a nucleotide sequence within SEQ ID NO:3 (e.g., a sequence comprising nucleotides 2131-2142, 2128-2145, or 2125-2148 of SEQ ID NO:3 (see FIG. 4B)).

In other embodiments, the nucleic acid fragment includes a bait that comprises a nucleotide sequence that hybridizes to a KIF5B-RET fusion nucleic acid molecule described herein, and thereby allows the capture or isolation said nucleic acid molecule. In one embodiment, a bait is suitable for solution phase hybridization. In other embodiments, a bait includes a binding entity, e.g., an affinity tag, that allows capture and separation, e.g., by binding to a binding entity, of a hybrid formed by a bait and a nucleic acid hybridized to the bait.

In other embodiments, the nucleic acid fragment includes a library member comprising a KIF5B-RET nucleic acid molecule described herein. In one embodiment, the library member includes a rearrangement that results in a KIF5B-RET fusion described herein.

The nucleic acid fragment can be detectably labeled with, e.g., a radiolabel, a fluorescent label, a bioluminescent label, a chemiluminescent label, an enzyme label, a binding pair label, or can include an affinity tag; a tag, or identifier (e.g., an adaptor, barcode or other sequence identifier).

KIF5B-RET Fusion Polypeptides

In another aspect, the invention features a KIF5B-RET fusion polypeptide (e.g., a purified KIF5B-RET fusion polypeptide), a biologically active or antigenic fragment thereof, as well as reagents (e.g., antibody molecules that bind to a KIF5B-RET fusion polypeptide), methods for modulating a KIF5B-RET polypeptide activity and detection of a KIF5B-RET polypeptide.

In one embodiment, the KIF5B-RET fusion polypeptide has at least one biological activity, e.g., a RET kinase activity, and/or a dimerizing or multimerizing activity. In one embodiment, at least one biological activity of the KIF5B-RET fusion polypeptide is reduced or inhibited by an anti-cancer drug, e.g., a kinase inhibitor (e.g., a multikinase inhibitor or a RET-specific inhibitor). In one embodiment, at least one biological activity of the KIF5B-RET fusion polypeptide is reduced or inhibited by a kinase inhibitor chosen from lenvatinib (E7080), sorafenib (NEXAVAR®), sunitinib (SUTENT®, SU11248), vandetanib (CAPRELSA®, ZACTIMA®, ZD6474), NVP-AST487, regorafenib (BAY-73-4506), motesanib (AMG 706), cabozantinib (XL-184), apatinib (YN-968D1), or DCC-2157.

In other embodiments, the KIF5B-RET fusion polypeptide includes a fragment of a KIF5B polypeptide and a fragment of a RET polypeptide. In one embodiment, the KIF5B-RET fusion polypeptide includes amino acids 578-575 of SEQ ID NO:2 or a fragment thereof (e.g., amino acids 1-575 of SEQ ID NO:2 or a fragment thereof), and amino acids 576-624 of SEQ ID NO:2 or a fragment thereof (e.g., amino acids 576-977 of SEQ ID NO:2 or a fragment thereof). In yet other embodiments, the KIF5B-RET fusion polypeptide includes an amino acid sequence substantially identical to an in-frame fusion of amino acids 578-575 of SEQ ID NO:2 or a fragment thereof (e.g., amino acids 1-575 of SEQ ID NO:2 or a fragment thereof), and amino acids 576-624 of SEQ ID NO:2 or a fragment thereof (e.g., amino acids 576-977 of SEQ ID NO:2 or a fragment thereof).

In other embodiments, the KIF5B-RET fusion polypeptide includes a KIF5B kinesin motor domain or a fragment thereof, and a RET kinase domain or a fragment thereof. In another embodiment, the KIF5B-RET fusion polypeptide includes the amino acid sequence of amino acids 1-575 of SEQ ID NO:2 or a fragment thereof, or a sequence substantially identical thereto. For example, the KIF5B-RET fusion polypeptide can include a kinesin motor domain of KIF5B that includes amino acids 6-325 of SEQ ID NO:2 or a fragment thereof. In other embodiments, the KIF5B-RET fusion polypeptide includes the amino acid sequence of amino acids 576-977 of SEQ ID NO:2 or a fragment thereof, or a sequence substantially identical thereto. For example, the KIF5B-RET fusion polypeptide can include a RET kinase domain that includes amino acids 587-868 of SEQ ID NO:2 or a fragment thereof. In yet other embodiments, the KIF5B-RET fusion polypeptide includes the amino acid sequence shown in FIGS. 3A-3D (e.g., SEQ ID NO:2) or a fragment thereof, or a sequence substantially identical thereto.

In yet other embodiments, the KIF5B-RET fusion polypeptide is encoded by a nucleic acid molecule described herein. In one embodiment, the KIF5B-RET fusion polypeptide is encoded by an in-frame fusion of exon 15 of KIF5B with exon 12 of RET (e.g., a sequence within an 11 MB pericentric inversion on chromosome 10). In other embodiments, the KIF5B-RET fusion polypeptide is encoded by a nucleotide sequence in the region of 32,316,376-32,316,416 of chromosome 10 coupled to (e.g., juxtaposed to) nucleotides in the region of nucleotides 43,611,042-43,611,118 of chromosome 10. In another embodiment, the KIF5B-RET fusion polypeptide includes an amino acid sequence encoded by a nucleotide sequence comprising a fusion junction between the KIF5B transcript and the RET transcript, e.g., a nucleotide sequence that includes a portion of SEQ ID NO:1 (e.g., a nucleotide sequence within exons 1-15 of a KIF5B gene and 12-20 of a RET gene) (e.g., a portion of SEQ ID NO:1 comprising nucleotides 1720-1731, 1717-1734, or 1714-1737 of SEQ ID NO:1 (see FIG. 3B)).

In yet other embodiments, the KIF5B-RET fusion polypeptide is encoded by a 5'-RET to 3'-KIF5B nucleic acid molecule described herein. In one embodiment, the KIF5B-RET fusion polypeptide is encoded by a nucleotide sequence that include a fusion junction between the RET transcript and the KIF5B transcript, e.g., a nucleotide sequence within SEQ ID NO:3 (e.g., a sequence comprising nucleotides 2131-2142, 2128-2145, or 2125-2148 of SEQ ID NO:3 (see FIG. 4B)). In yet other embodiments, the KIF5B-RET fusion polypeptide is encoded by the nucleotide sequence shown in FIGS. 4A-4D (e.g., SEQ ID NO:3) or a fragment thereof, or a sequence substantially identical thereto.

In an embodiment, the 5'KIF5B-3'RET fusion polypeptide comprises sufficient KIF5B and sufficient RET sequence such that it has kinase activity, e.g., has elevated activity, e.g., kinase activity, as compared with wild type RET, e.g., in a cell of a cancer referred to herein. In an embodiment the 5'KIF5B-3'RET fusion polypeptide comprises at least 1, 2, 3, 4, 5, 6, 7, 9, 10, or 11 exons from KIF5B and at least 1, 2, 3, 4, 5, 6, 7, 9, or 10, RET exons. In one embodiment, the 5'KIF5B-3'RET fusion polypeptide includes a kinesin motor domain or a functional fragment thereof, and a RET tyrosine kinase domain or a functional fragment thereof. In a related aspect, the invention features KIF5B-RET fusion polypeptide or fragments operatively linked to heterologous polypeptides to form fusion proteins.

In another embodiment, the KIF5B-RET fusion polypeptide or fragment is a peptide, e.g., an immunogenic peptide or protein, that contains a fusion junction described herein. Such immunogenic peptides or proteins can be used to raise antibodies specific to the fusion protein. In other embodiments, such immunogenic peptides or proteins can be used for vaccine preparation. The vaccine preparation can include other components, e.g., an adjuvant.

In another aspect, the invention features antibody molecules that bind to a KIF5B-RET fusion polypeptide or fragment described herein. In embodiments the antibody can distinguish wild type RET (or KIF5B) from KIF5B-RET.

Methods Reducing a KIF5B-RET Activity

In another aspect, the invention features a method of reducing an activity of a KIF5B-RET fusion. The method includes contacting the KIF5B-RET fusion, or a KIF5B-RET-expressing cell, with an agent that inhibits an activity or expression of KIF5B-RET (e.g., a kinase inhibitor). In one embodiment, the contacting step can be effected in vitro, e.g., in a cell lysate or in a reconstituted system. Alternatively, the method can be performed on cells in culture, e.g., in vitro or ex vivo. In other embodiments, the method can be performed on KIF5B-RET-expressing cells present in a subject, e.g., as part of an in vivo (e.g., therapeutic or prophylactic) protocol. In an embodiment the method is practiced on an animal subject (e.g., an in vivo animal model). In certain embodiments, the KIF5B-RET fusion is a nucleic acid molecule or a polypeptide as described herein.

In a related aspect, a method of inhibiting, reducing, or treating a hyperproliferative disorder, e.g., a cancer, in a subject is provided. The method includes administering to the subject a preselected therapeutic agent, e.g., an anti-cancer agent (e.g., a kinase inhibitor), as a single agent, or in combination, in an amount sufficient to reduce, inhibit or treat the activity or expression of KIF5B-RET (e.g., a KIF5B-RET fusion described herein), thereby inhibiting, reducing, or treating the hyperproliferative disorder in the subject. "Treatment" as used herein includes, but is not limited to, inhibiting tumor growth, reducing tumor mass, reducing size or number of metastatic lesions, inhibiting the development of new metastatic lesions, prolonged survival, prolonged progression-free survival, prolonged time to progression, and/or enhanced quality of life.

In one embodiment, the kinase inhibitor is administered based on a determination that a KIF5B-RET fusion is present in a subject, e.g., based on its present in a subject's sample. Thus, treatment can be combined with a KIF5B-RET detection or evaluation method, e.g., as described herein, or administered in response to a determination made by a KIF5B-RET detection or evaluation method, e.g., as described herein. In certain embodiments, the kinase inhibitor is administered responsive to acquiring knowledge or information of the presence of the KIF5B-RET fusion in a subject. In one embodiment, the kinase inhibitor is administered responsive to acquiring knowledge or information on the subject's genotype, e.g., acquiring knowledge or information that the patient's genotype has a KIF5B-RET fusion. In other embodiments, the kinase inhibitor is administered responsive to receiving a communication (e.g., a report) of the presence of the KIF5B-RET fusion in a subject (e.g., a subject's sample). In yet other embodiments, the kinase inhibitor is administered responsive to information obtained from a collaboration with another party that identifies the presence of the KIF5B-RET fusion in a subject (e.g., a subject's sample). In other embodiments, the kinase inhibitor is administered responsive to a determination that the KIF5B-RET fusion is present in a subject. In one embodiment, the determination of the presence of the KIF5B-RET fusion is carried out using one or more of the methods, e.g., the sequencing methods, described herein. In other embodiments, the determination of the presence of the KIF5B-RET fusion includes receiving information on the subject's KIF5B-RET fusion genotype, e.g., from another party or source.

The methods can, optionally, further include the step(s) of identifying (e.g., evaluating, diagnosing, screening, and/or selecting) a subject at risk of having, or having, a KIF5B-RET fusion. In one embodiment, the method further includes one or more of: acquiring knowledge or information of the presence of the KIF5B-RET fusion in a subject (e.g., a subject's sample); acquiring knowledge or information on the subject's genotype, e.g., acquiring knowledge or information that the patient's genotype has a KIF5B-RET fusion; receiving a communication (e.g., a report) of the presence of the KIF5B-RET fusion in a subject (e.g., a subject's sample); or collaborating with another party that identifies the presence of the KIF5B-RET fusion in a subject.

In one embodiment, the subject treated has a KIF5B-RET fusion; e.g., the subject has a tumor or cancer harboring a KIF5B-RET fusion. In other embodiments, the subject has been previously identified as having a KIF5B-RET fusion. In yet other embodiments, the subject has been previously identified as being likely or unlikely to respond to treatment with a protein kinase inhibitor, e.g., a subject that has previously participated in a clinical trial. In other embodiments, the subject has been previously identified as being likely or unlikely to respond to treatment with a protein kinase inhibitor, based on the presence of the KIF5B-RET fusion. In one embodiment, the subject is a mammal, e.g., a human. In one embodiment, the subject has, or at risk of having a cancer at any stage of disease. In other embodiments, the subject is a patient, e.g., a cancer patient.

In other embodiments, the subject treated is a cancer patient who has participated in a clinical trial. For example, the subject participated in a clinical trial that evaluated a kinase inhibitor (e.g., a multikinase inhibitor, a RET kinase inhibitor). In other embodiment, the subject participated in a clinical trial that evaluates upstream or downstream targets of RET. In one embodiment, said cancer patient responded to the kinase inhibitor evaluated.

In certain embodiments, the cancer is a solid tumor, a soft tissue tumor, or a metastatic lesion. In one embodiment, the cancer is chosen from a lung cancer, a pancreatic cancer, melanoma, a colorectal cancer, an esophageal-gastric cancer, a thyroid cancer, or an adenocarcinoma. In other embodiment, the lung cancer is chosen from one or more of the following: non-small cell lung cancer (NSCLC), small cell lung cancer (SCLC), squamous cell carcinoma (SCC), adenocarcinoma of the lung, bronchogenic carcinoma, or a combination thereof. In one embodiment, the lung cancer is NSCLC or SCC.

In one embodiment, the anti-cancer agent is a kinase inhibitor. For example, the kinase inhibitor is a multi-kinase inhibitor or a RET-specific inhibitor. In one embodiment, the kinase inhibitor is chosen from lenvatinib (E7080) (Eisai Co.), sorafenib (NEXAVAR®), sunitinib (SUTENT®, SU11248), vandetanib (CAPRELSA®, ZACTIMA®, ZD6474), NVP-AST487, regorafenib (BAY-73-4506), motesanib (AMG 706), cabozantinib (XL-184), apatinib (YN-968D1), or DCC-2157.

In other embodiments, the anti-cancer agent is a KIF5B-RET antagonist inhibits the expression of nucleic acid encoding KIF5B-RET. Examples of such KIF5B-RET antagonists include nucleic acid molecules, for example, antisense molecules, ribozymes, RNAi, triple helix molecules that hybridize to a nucleic acid encoding KIF5B-RET, or a transcription regulatory region, and blocks or reduces mRNA expression of KIF5B-RET.

In other embodiments, the kinase inhibitor is administered in combination with a second therapeutic agent or a different therapeutic modality, e.g., anti-cancer agents, and/or in combination with surgical and/or radiation procedures. For example, the second therapeutic agent can be a cytotoxic or a cytostatic agent. Exemplary cytotoxic agents include anti-microtubule agents, topoisomerase inhibitors, or taxanes, antimetabolites, mitotic inhibitors, alkylating agents, intercalating agents, agents capable of interfering with a signal transduction pathway, agents that promote apoptosis and radiation. In yet other embodiments, the methods can be used in combination with immunodulatory agents, e.g., IL-1, 2, 4, 6, or 12, or interferon alpha or gamma, or immune cell growth factors such as GM-CSF.

Screening Methods

In another aspect, the invention features a method, or assay, for screening for agents that modulate, e.g., inhibit, the expression or activity of a KIF5B-RET fusion, e.g., a KIF5B-RET fusion as described herein. The method includes contacting a KIF5B-RET fusion, or a cell expressing a KIF5B-RET fusion, with a candidate agent; and detecting a change in a parameter associated with a KIF5B-RET fusion, e.g., a change in the expression or an activity of the KIF5B-RET fusion. The method can, optionally, include comparing the treated parameter to a reference value, e.g., a control sample (e.g., comparing a parameter obtained from a sample with the candidate agent to a parameter obtained from a sample without the candidate agent). In one embodiment, if a decrease in expression or activity of the KIF5B-RET fusion is detected, the candidate agent is identified as an inhibitor. In another embodiment, if an increase in expression or activity of the KIF5B-RET fusion is detected, the candidate agent is identified as an activator. In certain embodiments, the KIF5B-RET fusion is a nucleic acid molecule or a polypeptide as described herein.

In one embodiment, the contacting step is effected in a cell-free system, e.g., a cell lysate or in a reconstituted system. In other embodiments, the contacting step is effected in a cell in culture, e.g., a cell expressing a KIF5B-RET fusion (e.g., a mammalian cell, a tumor cell or cell line, a recombinant cell). In yet other embodiments, the contacting step is effected in a cell in vivo (a KIF5B-RET-expressing cell present in a subject, e.g., an animal subject (e.g., an in vivo animal model).

Exemplary parameters evaluated include one or more of:

(i) a change in binding activity, e.g., direct binding of the candidate agent to a KIF5B-RET fusion polypeptide; a binding competition between a known ligand and the candidate agent to a KIF5B-RET fusion polypeptide;

(ii) a change in kinase activity, e.g., phosphorylation levels of a KIF5B-RET fusion polypeptide (e.g., an increased or decreased autophosphorylation); or a change in phosphorylation of a target of a RET kinase, e.g., focal adhesion kinase (FAK), persephin or glial derived neurotrophic factor (GDNF), In certain embodiments, a change in kinase activity, e.g., phosphorylation, is detected by any of Western blot (e.g., using an anti-KIF5B or anti-RET antibody; a phosphor-specific antibody, detecting a shift in the molecular weight of a KIF5B-RET fusion polypeptide), mass spectrometry, immunoprecipitation, immunohistochemistry, immunomagnetic beads, among others;

(iii) a change in an activity of a cell containing a KIF5B-RET fusion (e.g., a tumor cell or a recombinant cell), e.g., a change in proliferation, morphology or tumorigenicity of the cell;

(iv) a change in tumor present in an animal subject, e.g., size, appearance, proliferation, of the tumor; or (v) a change in the level, e.g., expression level, of a KIF5B-RET fusion polypeptide or nucleic acid molecule.

In one embodiment, a change in a cell free assay in the presence of a candidate agent is evaluated. For example, an activity of a KIF5B-RET fusion, or interaction of a KIF5B-RET fusion with a downstream ligand can be detected. In one embodiment, a KIF5B-RET fusion polypeptide is contacted with a ligand, e.g., in solution, and a candidate agent is monitored for an ability to modulate, e.g., inhibit, an interaction, e.g., binding, between the KIF5B-RET fusion polypeptide and the ligand.

In other embodiments, a change in an activity of a cell is detected in a cell in culture, e.g., a cell expressing a KIF5B-RET fusion (e.g., a mammalian cell, a tumor cell or cell line, a recombinant cell). In one embodiment, the cell is a recombinant cell that is modified to express a KIF5B-RET fusion nucleic acid, e.g., is a recombinant cell transfected with a KIF5B-RET fusion nucleic acid. The transfected cell can show a change in response to the expressed KIF5B-RET fusion, e.g., increased proliferation, changes in morphology, increased tumorigenicity, and/or acquired a transformed phenotype. A change in any of the activities of the cell, e.g., the recombinant cell, in the presence of the candidate agent can be detected. For example, a decrease in one or more of: proliferation, tumorigenicity, transformed morphology, in the presence of the candidate agent can be indicative of an inhibitor of a KIF5B-RET fusion. In other embodiments, a change in binding activity or phosphorylation as described herein is detected.

In yet other embodiment, a change in a tumor present in an animal subject (e.g., an in vivo animal model) is detected. In one embodiment, the animal model is a tumor containing animal or a xenograft comprising cells expressing a KIF5B-RET fusion (e.g., tumorigenic cells expressing a KIF5B-RET fusion). The candidate agent can be administered to the animal subject and a change in the tumor is detected. In one embodiment, the change in the tumor includes one or more of a tumor growth, tumor size, tumor burden, survival, is evaluated. A decrease in one or more of tumor growth, tumor size, tumor burden, or an increased survival is indicative that the candidate agent is an inhibitor.

In other embodiments, a change in expression of a KIF5B-RET fusion can be monitored by detecting the nucleic acid or protein levels, e.g., using the methods described herein.

In certain embodiments, the screening methods described herein can be repeated and/or combined. In one embodiment, a candidate agent that is evaluated in a cell-free or cell-based described herein can be further tested in an animal subject.

In one embodiment, the candidate agent is a small molecule compound, e.g., a kinase inhibitor, a nucleic acid (e.g., antisense, siRNA, aptamer, ribozymes, microRNA), an antibody molecule (e.g., a full antibody or antigen binding fragment thereof that binds to KIF5B5 or RET). The candidate agent can be obtained from a library (e.g., a commercial library of kinase inhibitors) or rationally designed (e.g., based on the RET kinase domain).

Methods for Detecting KIF5B-RET Fusions

In another aspect, the invention features a method of determining the presence of a KIF5B-RET fusion, e.g., a KIF5B-RET fusion as described herein. In one embodiment, the KIF5B-RET fusion is detected in a nucleic acid molecule or a polypeptide. The method includes detecting whether a KIF5B-RET fusion nucleic acid molecule or polypeptide is present in a cell (e.g., a circulating cell), a tissue (e.g., a tumor), or a sample, e.g., a tumor sample, from a subject. In one embodiment, the sample is a nucleic acid sample. In one embodiment, the nucleic acid sample comprises DNA, e.g., genomic DNA or cDNA, or RNA, e.g., mRNA. In other embodiments, the sample is a protein sample.

In one embodiment, the sample is, or has been, classified as non-malignant using other diagnostic techniques, e.g., immunohistochemistry.

In one embodiment, the sample is acquired from a subject (e.g., a subject having or at risk of having a cancer, e.g., a patient), or alternatively, the method further includes acquiring a sample from the subject. The sample can be chosen from one or more of: tissue, e.g., cancerous tissue (e.g., a tissue biopsy), whole blood, serum, plasma, buccal scrape, sputum, saliva, cerebrospinal fluid, urine, stool, circulating tumor cells, circulating nucleic acids, or bone marrow. In certain embodiments, the sample is a tissue (e.g., a tumor biopsy), a circulating tumor cell or nucleic acid.

In embodiments, the tumor is from a cancer described herein, e.g., is chosen from a lung cancer, a colorectal cancer, an esophageal-gastric cancer, a thyroid cancer, an adenocarcinoma or a melanoma. In one embodiment, the tumor is from a lung cancer, e.g., a NSCLC, a SCLC, a SCC, or a combination thereof.

In one embodiment, the subject is at risk of having, or has a cancer (e.g., a patient with a cancer described herein). For example, in one embodiment, the subject is at risk for having, or has a lung cancer.

In other embodiments, the KIF5B-RET fusion is detected in a nucleic acid molecule by a method chosen from one or more of: nucleic acid hybridization assay, amplification-based assays (e.g., polymerase chain reaction (PCR)), PCR-RFLP assay, real-time PCR, sequencing, screening analysis (including metaphase cytogenetic analysis by standard karyotype methods, FISH (e.g., break away FISH), spectral karyotyping or MFISH, comparative genomic hybridization), in situ hybridization, SSP, HPLC or mass-spectrometric genotyping.

In one embodiment, the method includes: contacting a nucleic acid sample, e.g., a genomic DNA sample (e.g., a chromosomal sample or a fractionated, enriched or otherwise pre-treated sample) or a gene product (mRNA, cDNA), obtained from the subject, with a nucleic acid fragment (e.g., a probe or primer as described herein (e.g., an exon-specific probe or primer) under conditions suitable for hybridization, and determining the presence or absence of the KIF5B-RET nucleic acid molecule. The method can, optionally, include enriching a sample for the gene or gene product.

In a related aspect, a method for determining the presence of a KIF5B-RET fusion nucleic acid molecule is provided. The method includes: acquiring a sequence for a position in a nucleic acid molecule, e.g., by sequencing at least one nucleotide of the nucleic acid molecule (e.g., sequencing at least one nucleotide in the nucleic acid molecule that comprises the KIF5B-RET fusion), thereby determining that the KIF5B-RET fusion is present in the nucleic acid molecule. Optionally, the sequence acquired is compared to a reference sequence, or a wild type reference sequence. In one embodiment, the nucleic acid molecule is from a cell (e.g., a circulating cell), a tissue (e.g., a tumor), or any sample from a subject (e.g., blood or plasma sample). In other embodiments, the nucleic acid molecule from a tumor sample (e.g., a tumor or cancer sample) is sequenced. In one embodiment, the sequence is determined by a next generation sequencing method. The method further can further include acquiring, e.g., directly or indirectly acquiring, a sample, e.g., a tumor or cancer sample, from a subject (e.g., a patient). In certain embodiments, the cancer is chosen from a lung cancer, colorectal cancer, esophageal-gastric cancer or melanoma.

In another aspect, the invention features a method of analyzing a tumor or a circulating tumor cell. The method includes acquiring a nucleic acid sample from the tumor or the circulating cell; and sequencing, e.g., by a next generation sequencing method, a nucleic acid molecule, e.g., a nucleic acid molecule that includes a KIF5B-RET fusion described herein.

In yet another embodiment, a KIF5B-RET fusion polypeptide is detected. The method includes: contacting a protein sample with a reagent which specifically binds to a KIF5B-RET fusion polypeptide; and detecting the formation of a complex of the KIF5B-RET fusion polypeptide and the reagent. In one embodiment, the reagent is labeled with a detectable group to facilitate detection of the bound and unbound reagent. In one embodiment, the reagent is an antibody molecule, e.g., is selected from the group consisting of an antibody, and antibody derivative, and an antibody fragment.

In yet another embodiment, the level (e.g., expression level) or activity the KIF5B-RET fusion is evaluated. For example, the level (e.g., expression level) or activity of the KIF5B-RET fusion (e.g., mRNA or polypeptide) is detected and (optionally) compared to a pre-determined value, e.g., a reference value (e.g., a control sample).

In yet another embodiment, the KIF5B-RET fusion is detected prior to initiating, during, or after, a treatment in a subject, e.g., a treatment with a kinase inhibitor. In one embodiment, the KIF5B-RET fusion is detected at the time of diagnosis with a cancer. In other embodiment, the KIF5B-RET fusion is detected at a pre-determined interval, e.g., a first point in time and at least at a subsequent point in time.

In certain embodiments, responsive to a determination of the presence of the KIF5B-RET fusion, the method further includes one or more of:

(1) stratifying a patient population (e.g., assigning a subject, e.g., a patient, to a group or class);

(2) identifying or selecting the subject as likely or unlikely to respond to a treatment, e.g., a kinase inhibitor treatment as described herein;

(3) selecting a treatment option, e.g., administering or not administering a preselected therapeutic agent, e.g., a kinase inhibitor as described herein; or (4) prognosticating the time course of the disease in the subject (e.g., evaluating the likelihood of increased or decreased patient survival).

In certain embodiments, the kinase inhibitor is a multi-kinase inhibitor or a RET-specific inhibitor. In one embodiment, the kinase inhibitor is chosen from lenvatinib (E7080), sorafenib (NEXAVAR®), sunitinib (SUTENT®, SU11248), vandetanib (CAPRELSA®, ZACTIMA®, ZD6474), NVP-AST487, regorafenib (BAY-73-4506), motesanib (AMG 706), cabozantinib (XL-184), apatinib (YN-968D1), or DCC-2157.

In certain embodiments, responsive to the determination of the presence of the KIF5B-RET fusion, the subject is classified as a candidate to receive treatment with a kinase inhibitor, e.g., a kinase inhibitor as described herein. In one embodiment, responsive to the determination of the presence of the KIF5B-RET fusion, the subject, e.g., a patient, can further be assigned to a particular class if a KIF5B-RET fusion is identified in a sample of the patient. For example, a patient identified as having a KIF5B-RET fusion can be classified as a candidate to receive treatment with a kinase inhibitor, e.g., a kinase inhibitor as described herein. In one embodiment, the subject, e.g., a patient, is assigned to a second class if the mutation is not present. For example, a patient who has a lung tumor that does not contain a KIF5B-RET fusion, may be determined as not being a candidate to receive a kinase inhibitor, e.g., a kinase inhibitor as described herein.

In another embodiment, responsive to the determination of the presence of the KIF5B-RET fusion, the subject is identified as likely to respond to a treatment that comprises a kinase inhibitor e.g., a kinase inhibitor as described herein.

In yet another embodiment, responsive to the determination of the presence of the KIF5B-RET fusion, the method includes administering a kinase inhibitor, e.g., a kinase inhibitor as described herein, to the subject.

Method of Evaluating a Tumor or a Subject

In another aspect, the invention features a method of evaluating a subject (e.g., a patient), e.g., for risk of having or developing a cancer, e.g., a lung cancer, colorectal cancer or skin cancer. The method includes: acquiring information or knowledge of the presence of a KIF5B-RET fusion in a subject (e.g., acquiring genotype information of the subject that identifies a KIF5B-RET fusion as being present in the subject); acquiring a sequence for a nucleic acid molecule identified herein (e.g., a nucleic acid molecule that includes a KIF5B-RET fusion sequence); or detecting the presence of a KIF5B-RET fusion nucleic acid or polypeptide in the subject), wherein the presence of the KIF5B-RET fusion is positively correlated with increased risk for, or having, a cancer associated with the KIF5B-RET fusion.

The method can further include the step(s) of identifying (e.g., evaluating, diagnosing, screening, and/or selecting) the subject as being positively correlated with increased risk for, or having, a cancer associated with the KIF5B-RET fusion. In one embodiment, the subject is identified or selected as likely or unlikely to respond to a treatment, e.g., a kinase inhibitor treatment as described herein.

The method can further include treating the subject with a kinase inhibitor, e.g., a kinase inhibitor as described herein.

The method can further include acquiring, e.g., directly or indirectly, a sample from a patient and evaluating the sample for the present of a KIF5B-RET fusion as described herein.

In certain embodiments, the subject is a patient or patient population that has participated in a clinical trial. In one embodiment, the subject has participated in a clinical trial for evaluating a kinase inhibitor (e.g., a multikinase inhibitor or a RET inhibitor). In one embodiment, the clinical trial is discontinued or terminated. In other embodiments, the subject has participated in a clinical trial that evaluates a RET kinase, a KIF5B inhibitor (e.g., a kinesin inhibitor), an upstream or downstream component of RET or KIF5B. In one embodiment, the subject responded favorably to the clinical trial, e.g., experience an improvement in at least one symptom of a cancer (e.g., decreased in tumor size, rate of tumor growth, increased survival). In other embodiments, the subject did not respond in a detectable way to the clinical trial.

In a related aspect, a method of evaluating a patient or a patient population is provided. The method includes: identifying, selecting, or obtaining information or knowledge that the patient or patient population has participated in a clinical trial;

acquiring information or knowledge of the presence of a KIF5B-RET fusion in the patient or patient population (e.g., acquiring genotype information of the subject that identifies a KIF5B-RET fusion as being present in the subject); acquiring a sequence for a nucleic acid molecule identified herein (e.g., a nucleic acid molecule that includes a KIF5B-RET fusion sequence); or detecting the presence of a KIF5B-RET fusion nucleic acid or polypeptide in the subject), wherein the presence of the KIF5B-RET fusion is identifies the patient or patient population as having an increased risk for, or having, a cancer associated with the KIF5B-RET fusion.

In certain embodiments, the subject is a patient or patient population that has participated in a clinical trial. In one embodiment, the subject has participated in a clinical trial for evaluating a kinase inhibitor (e.g., a multikinase inhibitor or a RET inhibitor). In one embodiment, the clinical trial is discontinued or terminated. In other embodiments, the subject has participated in a clinical trial that evaluates a RET kinase, a KIF5B inhibitor (e.g., a kinesin inhibitor), an upstream or downstream component of RET or KIF5B. In one embodiment, the subject responded favorably to the clinical trial, e.g., experience an improvement in at least one symptom of a cancer (e.g., decreased in tumor size, rate of tumor growth, increased survival). In other embodiments, the subject did not respond in a detectable way to the clinical trial.

In embodiments, the method further includes treating the subject with a kinase inhibitor, e.g., a kinase inhibitor as described herein.

Reporting

Methods described herein can include providing a report, such as, in electronic, web-based, or paper form, to the patient or to another person or entity, e.g., a caregiver, e.g., a physician, e.g., an oncologist, a hospital, clinic, third-party payor, insurance company or government office. The report can include output from the method, e.g., the identification of nucleotide values, the indication of presence or absence of a KIF5B-RET fusion as described herein, or wildtype sequence. In one embodiment, a report is generated, such as in paper or electronic form, which identifies the presence or absence of an alteration described herein, and optionally includes an identifier for the patient from which the sequence was obtained.

The report can also include information on the role of a sequence, e.g., a KIF5B-RET fusion as described herein, or wildtype sequence, in disease. Such information can include information on prognosis, resistance, or potential or suggested therapeutic options. The report can include information on the likely effectiveness of a therapeutic option, the acceptability of a therapeutic option, or the advisability of applying the therapeutic option to a patient, e.g., a patient having a sequence, alteration or mutation identified in the test, and in embodiments, identified in the report. For example, the report can include information, or a recommendation on, the administration of a drug, e.g., the administration at a preselected dosage or in a preselected treatment regimen, e.g., in combination with other drugs, to the patient. In an embodiment, not all mutations identified in the method are identified in the report. For example, the report can be limited to mutations in genes having a preselected level of correlation with the occurrence, prognosis, stage, or susceptibility of the cancer to treatment, e.g., with a preselected therapeutic option. The report can be delivered, e.g., to an entity described herein, within 7, 14, or 21 days from receipt of the sample by the entity practicing the method.

In another aspect, the invention features a method for generating a report, e.g., a personalized cancer treatment report, by obtaining a sample, e.g., a tumor sample, from a subject, detecting a KIF5B-RET fusion as described herein in the sample, and selecting a treatment based on the mutation identified. In one embodiment, a report is generated that annotates the selected treatment, or that lists, e.g., in order of preference, two or more treatment options based on the mutation identified. In another embodiment, the subject, e.g., a patient, is further administered the selected method of treatment.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In case of conflict, the present specification, including definitions, will control. In addition, the materials, methods, and the example are illustrative only and not intended to be limiting.

The details of one or more embodiments featured in the invention are set forth in the accompanying drawings and the description below. Other features, objects, and advantages featured in the invention will be apparent from the description and drawings, and from the claims.

BRIEF DESCRIPTION OF DRAWINGS

FIGS. 3A to 3D are the predicted cDNA sequence (SEQ ID NO:1) and protein sequence of the KIF5B-RET fusion (SEQ ID NO:2). The KIF5B portion of the cDNA sequence is equivalent to nucleotides 471-2195 of RefSeq NM_004521.2, and the KIF5B portion of the protein sequence is equivalent to amino acids 1-575 of RefSeq NP_004512. The KIF5B portions of the cDNA and protein sequences are underlined. The RET portion of the cDNA sequence is equivalent to nucleotides 2327-3535 of RefSeq NM_020975, and the RET portion of the protein sequence is equivalent to amino acids 713-1114 of RefSeq NP_066124.1. The intact tyrosine kinase domain of RET is represented by a gray box (see FIG. 3C).

FIGS. 4A to 4D are the predicted cDNA sequence (SEQ ID NO:3) and protein sequence of the RET-KIF5B fusion (SEQ ID NO:4). The cDNA sequence of the RET portion of the fusion transcript is equivalent to nucleotides 190-2326 of RefSeq NM_020975, and the protein sequence is equivalent to amino acids 1-712 of RefSeq NP_066124.1. The cDNA sequence of the KIF5B portion of the fusion transcript is equivalent to nucleotides 2196-3362 of RefSeq NM_004521.2, and the protein portion is equivalent to amino acids 576-963 of RefSeq NP_004512. The KIF5B portions of the cDNA and protein sequences are underlined.

FIG. 7B is another representation of the predicted KIF5B-RET variant amino acid sequence.

Figure 1:
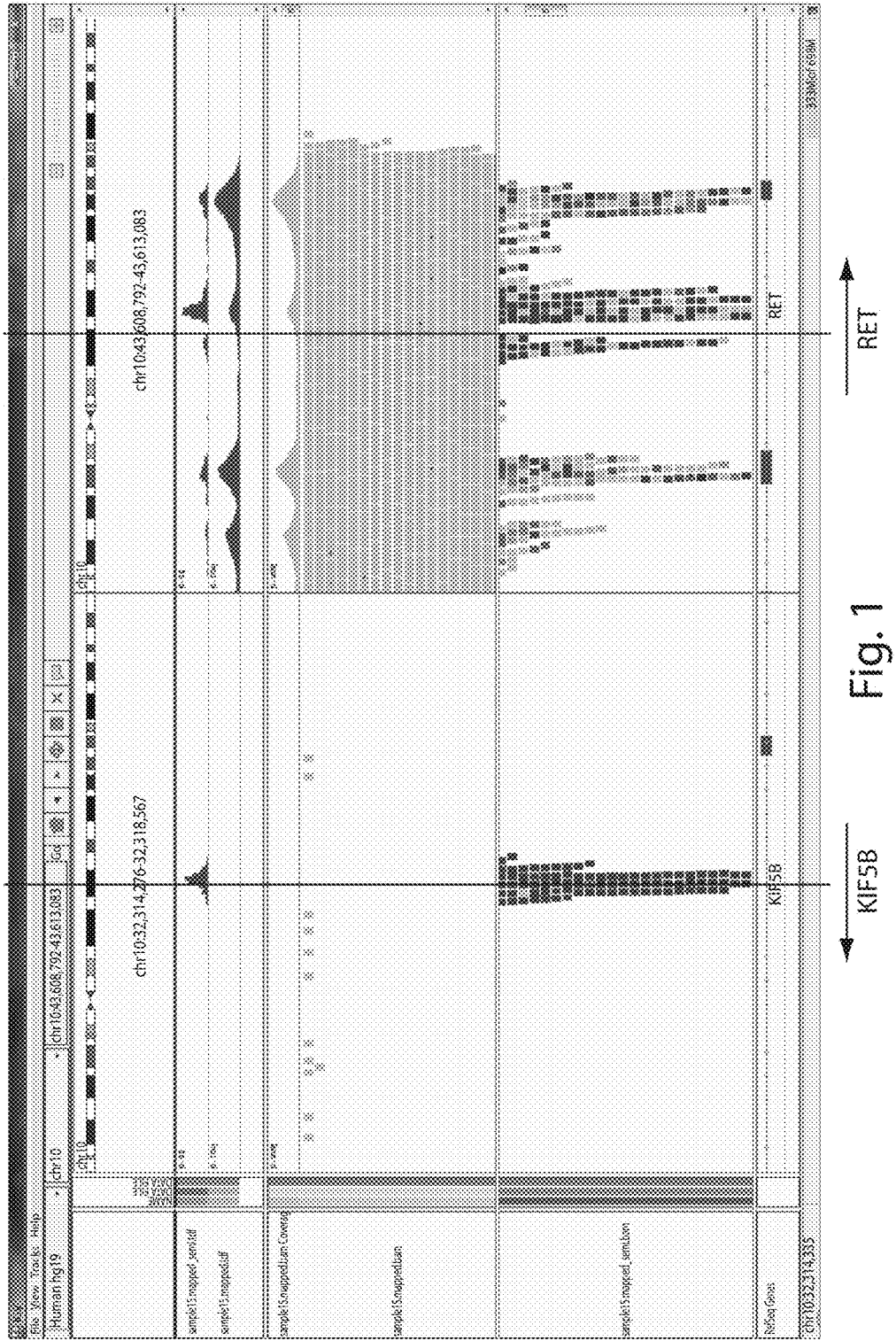
FIG. 1 is a snapshot of the sequencing reads illustrating that there are RET read pairs that map on one end to 5'KIF5B and on the other end to 3'RET, and other RET read pairs that map on one end to 5'RET and on the other end to 3'KIFB.
Figure 2A:
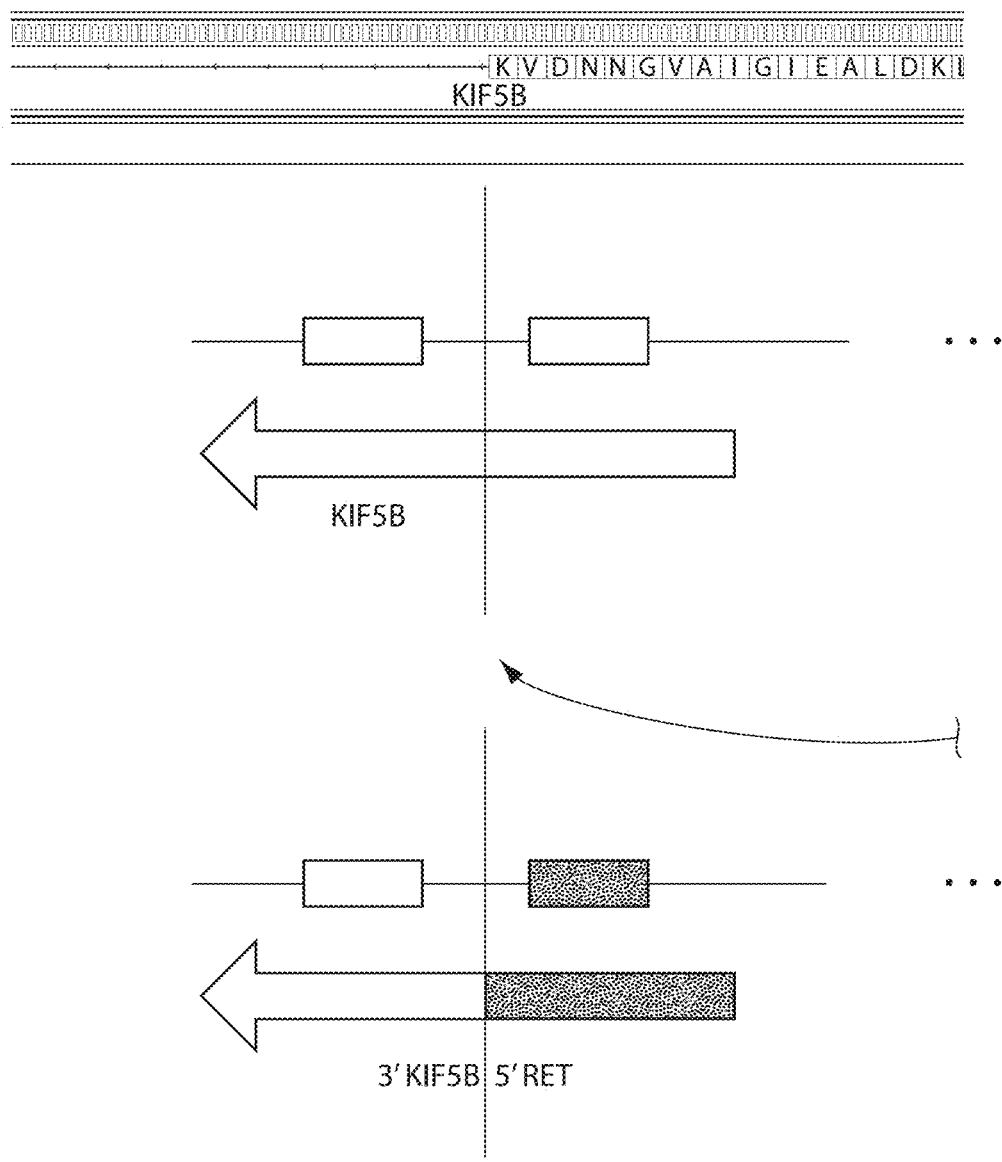
FIGS. 2A and 2B are schematic diagrams illustrating the inversion event that brings together exon 15 of KIF5B and exon 12 of RET.
Figure 2B:
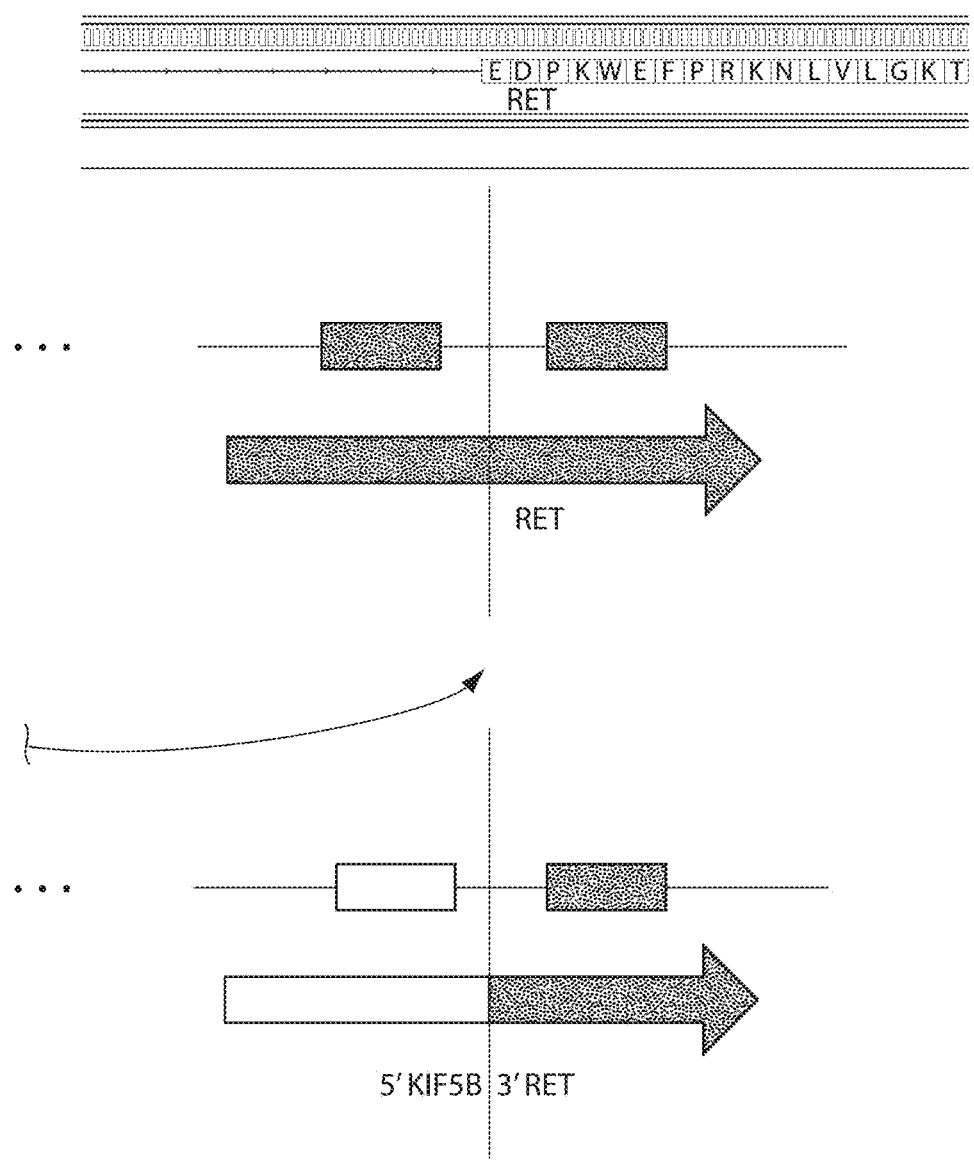

The Tables are described herein.

Table 1 is a summary of the distribution of 125 CRC mutations across 21 mutated cancer genes Table 2 provides a summary of NSCLC patients analyzed by RET immunohistochemistry.

Supplementary Table 1a provides a listing of the 145 genes sequenced across the entire coding sequence.

Supplementary Table 1b provides a listing of the 14 genes sequenced across selected introns.

Supplementary Table 2a provides a detailed summary of the alterations detected in 40 colorectal cancer cases.

Supplementary Table 2b provides a detailed summary of the alterations detected in 24 NSCLC cases.

Supplementary Table 3 provides a summary of the alterations that could be linked to a clinical treatment option or a clinical trial of novel targeted therapies.

Supplementary Table 4 provides a distribution of 51 mutations across 21 mutated NSCLC genes.

Supplementary Table 5 provides a summary of NSCLC alterations that could be linked to a clinical treatment option or clinical trial or novel targeted therapies.

DETAILED DESCRIPTION

The invention is based, at least in part, on the discovery of a novel chromosomal inversion event and its association with cancer, e.g., lung cancer. In one embodiment, Applicants have discovered an inversion on chromosome 10 that results in an in-frame fusion of a fragment of a KIF5B gene and a fragment of a RET gene.

The term "KIF5B-RET" or "KIF5B-RET fusion" is used generically herein, and includes any fusion molecule (e.g., gene, gene product (e.g., cDNA, mRNA, polypeptide), and variant thereof) that includes a fragment of KIF5B and a fragment of RET, in any configuration, including, e.g., a 5'KIF5B-3'RET or a 5'RET-3'KIF5B fusion molecule.

In one embodiment, a KIF5B-RET fusion includes an in-frame fusion of an exon of KIF5B (e.g., one more exons encoding a kinesin motor domain or a fragment thereof) and an exon of RET (e.g., one or more exons encoding a RET tyrosine kinase domain or a fragment thereof). For example, the KIF5B-RET fusion can include an in-frame fusion of at least exon 15 of KIF5B or a fragment thereof (e.g., exons 1-15 of KIF5B or a fragment thereof) with at least exon 12 of RET or a fragment thereof (e.g., exons 12-20 of RET or a fragment thereof). In certain embodiments, the KIF5B-RET fusion is in a 5'-KIF5B to 3'-RET configuration referred to herein as "5'KIF5B-3'RET."

In other embodiments, the KIF5B-RET fusion includes an in-frame fusion of at least exon 11 of RET or a fragment thereof (e.g., exons 1-11 of RET or a fragment thereof) with at least exon 16 or a fragment thereof (e.g., exons 16-25 of KIF5B or a fragment thereof). In certain embodiments, the KIF5B-RET fusion is in a 5'-RET to 3'-KIF5B configuration referred to herein as "5'RET-3'KIF5B").

The RET proto-oncogene is known to be associated with cancerous phenotypes, including papillary thyroid carcinomas (PTC), multiple endocrine neoplasias (MEN), phaeochromocytoma, among others. For example, chromosomal rearrangements that generate a fusion gene resulting in the juxtaposition of the C-terminal region of the RET protein with an N-terminal portion of another protein (known as RET/PTC) are known to be associated with PTC (Nikiforov, Y E (2002) *Endocr. Pathol.* 13 (1):3-16). Thus, the KIF5B-RET fusions disclosed herein (e.g., the 5'-KIF5B to 3'-RET fusions that include a RET tyrosine kinase domain) are likely to be associated with cancers, e.g., lung cancer.

Accordingly, the invention provides, at least in part, isolated KIF5B-RET nucleic acid molecules, nucleic acid constructs, host cells containing the nucleic acid molecules; purified KIF5B-RET polypeptides and binding agents; detection reagents (e.g., probes, primers, antibodies, kits); screening assays for identifying novel kinase inhibitors; as well as methods, assays and kits for evaluating, identifying, assessing and/or treating a subject having a cancer, e.g., a cancer having a KIF5B-RET fusion disclosed herein. The compositions and methods identified herein can be used, for example, to identify new KIF5B-RET inhibitors; to treat or prevent a cancer; as well as in methods or assays for evaluating a cancer (e.g., evaluating one or more of: cancer progression, cancer treatment response or resistance to cancer treatment; selecting a treatment option, stratifying a patient population, and/or more effectively monitoring, treating or preventing a cancer).

Certain terms are first defined. Additional terms are defined throughout the specification.

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

"Acquire" or "acquiring" as the terms are used herein, refer to obtaining possession of a physical entity, or a value, e.g., a numerical value, by "directly acquiring" or "indirectly acquiring" the physical entity or value. "Directly acquiring" means performing a process (e.g., performing a synthetic or analytical method) to obtain the physical entity or value. "Indirectly acquiring" refers to receiving the physical entity or value from another party or source (e.g., a third party laboratory that directly acquired the physical entity or value). Directly acquiring a physical entity includes performing a process that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent.

"Acquiring a sequence" as the term is used herein, refers to obtaining possession of a nucleotide sequence or amino acid sequence, by "directly acquiring" or "indirectly acquiring" the sequence. "Directly acquiring a sequence" means performing a process (e.g., performing a synthetic or analytical method) to obtain the sequence, such as performing a sequencing method (e.g., a Next Generation Sequencing (NGS) method). "Indirectly acquiring a sequence" refers to receiving information or knowledge of, or receiving, the sequence from another party or source (e.g., a third party laboratory that directly acquired the sequence). The sequence acquired need not be a full sequence, e.g., sequencing of at least one nucleotide, or obtaining information or knowledge, that identifies a KIF5B-RET fusion disclosed herein as being present in a subject constitutes acquiring a sequence.

Directly acquiring a sequence includes performing a process that includes a physical change in a physical substance, e.g., a starting material, such as a tissue sample, e.g., a biopsy, or an isolated nucleic acid (e.g., DNA or RNA) sample. Exemplary changes include making a physical entity from two or more starting materials, shearing or fragmenting a substance, such as a genomic DNA fragment; separating or purifying a substance (e.g., isolating a nucleic acid sample from a tissue); combining two or more separate entities into a mixture, performing a chemical reaction that includes breaking or forming a covalent or non-covalent bond. Directly acquiring a value includes performing a process that includes a physical change in a sample or another substance as described above.

"Acquiring a sample" as the term is used herein, refers to obtaining possession of a sample, e.g., a tissue sample or nucleic acid sample, by "directly acquiring" or "indirectly acquiring" the sample. "Directly acquiring a sample" means performing a process (e.g., performing a physical method such as a surgery or extraction) to obtain the sample. "Indirectly acquiring a sample" refers to receiving the sample from another party or source (e.g., a third party laboratory that directly acquired the sample). Directly acquiring a sample includes performing a process that includes a physical change in a physical substance, e.g., a starting material, such as a tissue, e.g., a tissue in a human patient or a tissue that has was previously isolated from a patient. Exemplary changes include making a physical entity from a starting material, dissecting or scraping a tissue; separating or purifying a substance (e.g., a sample tissue or a nucleic acid sample); combining two or more separate entities into a mixture; performing a chemical reaction that includes breaking or forming a covalent or non-covalent bond. Directly acquiring a sample includes performing a process that includes a physical change in a sample or another substance, e.g., as described above.

"Binding entity" means any molecule to which molecular tags can be directly or indirectly attached that is capable of specifically binding to an analyte. The binding entity can be an affinity tag on a nucleic acid sequence. In certain embodiments, the binding entity allows for separation of the nucleic acid from a mixture, such as an avidin molecule, or an antibody that binds to the hapten or an antigen-binding fragment thereof. Exemplary binding entities include, but are not limited to, a biotin molecule, a hapten, an antibody, an antibody binding fragment, a peptide, and a protein.

"Complementary" refers to sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In certain embodiments, the first region comprises a first portion and the second region comprises a second portion, whereby, when the first and second portions are arranged in an antiparallel fashion, at least about 50%, at least about 75%, at least about 90%, or at least about 95% of the nucleotide residues of the first portion are capable of base pairing with nucleotide residues in the second portion. In other embodiments, all nucleotide residues of the first portion are capable of base pairing with nucleotide residues in the second portion.

The term "cancer" or "tumor" is used interchangeably herein. These terms refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells can exist alone within an animal, or can be a non-tumorigenic cancer cell, such as a leukemia cell. These terms include a solid tumor, a soft tissue tumor, or a metastatic lesion. As used herein, the term "cancer" includes premalignant, as well as malignant cancers.

Cancer is "inhibited" if at least one symptom of the cancer is alleviated, terminated, slowed, or prevented. As used herein, cancer is also "inhibited" if recurrence or metastasis of the cancer is reduced, slowed, delayed, or prevented.

"Chemotherapeutic agent" means a chemical substance, such as a cytotoxic or cytostatic agent, that is used to treat a condition, particularly cancer.

As used herein, "cancer therapy" and "cancer treatment" are synonymous terms.

As used herein, "chemotherapy" and "chemotherapeutic" and "chemotherapeutic agent" are synonymous terms.

The terms "homology" or "identity," as used interchangeably herein, refer to sequence similarity between two polynucleotide sequences or between two polypeptide sequences, with identity being a more strict comparison. The phrases "percent identity or homology" and "% identity or homology" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar, or any integer value there between. Identity or similarity can be determined by comparing a position in each sequence that can be aligned for purposes of comparison. When a position in the compared sequence is occupied by the same nucleotide base or amino acid, then the molecules are identical at that position. A degree of similarity or identity between polynucleotide sequences is a function of the number of identical or matching nucleotides at positions shared by the polynucleotide sequences. A degree of identity of polypeptide sequences is a function of the number of identical amino acids at positions shared by the polypeptide sequences. A degree of homology or similarity of polypeptide sequences is a function of the number of amino acids at positions shared by the polypeptide sequences. The term "substantially identical," as used herein, refers to an identity or homology of at least 75%, at least 80%, at least 85%, at least 90%, 91%, 92%, 93%, 94%, 95%, 96%, 97%, 98%, 99%, or more.

"Likely to" or "increased likelihood," as used herein, refers to an increased probability that an item, object, thing or person will occur. Thus, in one example, a subject that is likely to respond to treatment with a kinase inhibitor, alone or in combination, has an increased probability of responding to treatment with the inhibitor alone or in combination, relative to a reference subject or group of subjects.

"Unlikely to" refers to a decreased probability that an event, item, object, thing or person will occur with respect to a reference. Thus, a subject that is unlikely to respond to treatment with a kinase inhibitor, alone or in combination, has a decreased probability of responding to treatment with a kinase inhibitor, alone or in combination, relative to a reference subject or group of subjects.

"Sequencing" a nucleic acid molecule requires determining the identity of at least 1 nucleotide in the molecule. In embodiments, the identity of less than all of the nucleotides in a molecule are determined. In other embodiments, the identity of a majority or all of the nucleotides in the molecule is determined.

"Next-generation sequencing or NGS or NG sequencing" as used herein, refers to any sequencing method that determines the nucleotide sequence of either individual nucleic acid molecules (e.g., in single molecule sequencing) or clonally expanded proxies for individual nucleic acid molecules in a highly parallel fashion (e.g., greater than $10^5$ molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. (2010) *Nature Biotechnology Reviews* 11:31-46, incorporated herein by reference. Next generation sequencing can detect a variant present in less than 5% of the nucleic acids in a sample.

"Sample," "tissue sample," "patient sample," "patient cell or tissue sample" or "specimen" each refers to a collection of similar cells obtained from a tissue of a subject or patient. The source of the tissue sample can be solid tissue as from a fresh, frozen and/or preserved organ, tissue sample, biopsy, or aspirate; blood or any blood constituents; bodily fluids such as cerebral spinal fluid, amniotic fluid, peritoneal fluid or interstitial fluid; or cells from any time in gestation or development of the subject. The tissue sample can contain compounds that are not naturally intermixed with the tissue in nature such as preservatives, anticoagulants, buffers, fixatives, nutrients, antibiotics or the like. In one embodiment, the sample is preserved as a frozen sample or as formaldehyde- or paraformaldehyde-fixed paraffin-embedded (FFPE) tissue preparation. For example, the sample can be embedded in a matrix, e.g., an FFPE block or a frozen sample.

A "tumor nucleic acid sample" as used herein, refers to nucleic acid molecules from a tumor or cancer sample. Typically, it is DNA, e.g., genomic DNA, or cDNA derived from RNA, from a tumor or cancer sample. In certain embodiments, the tumor nucleic acid sample is purified or isolated (e.g., it is removed from its natural state).

A "control" or "reference" "nucleic acid sample" as used herein, refers to nucleic acid molecules from a control or reference sample. Typically, it is DNA, e.g., genomic DNA, or cDNA derived from RNA, not containing the alteration or variation in the gene or gene product, e.g., not containing a KIF5B-RET fusion. In certain embodiments, the reference or control nucleic acid sample is a wild type or a non-mutated sequence. In certain embodiments, the reference nucleic acid sample is purified or isolated (e.g., it is removed from its natural state). In other embodiments, the reference nucleic acid sample is from a non-tumor sample, e.g., a blood control, a normal adjacent tumor (NAT), or any other non-cancerous sample from the same or a different subject.

Headings, e.g., (a), (b), (i) etc, are presented merely for ease of reading the specification and claims. The use of headings in the specification or claims does not require the steps or elements be performed in alphabetical or numerical order or the order in which they are presented.

Various aspects of the invention are described in further detail below. Additional definitions are set out throughout the specification.

Isolated Nucleic Acid Molecules

One aspect of the invention pertains to isolated nucleic acid molecules that include a KIF5B-RET fusion, including nucleic acids which encode a KIF5B-RET fusion polypeptide or a portion of such a polypeptide. The nucleic acid molecules include those nucleic acid molecules which reside in genomic regions identified herein. As used herein, the term "nucleic acid molecule" includes DNA molecules (e.g., cDNA or genomic DNA) and RNA molecules (e.g., mRNA) and analogs of the DNA or RNA generated using nucleotide analogs. The nucleic acid molecule can be single-stranded or double-stranded; in certain embodiments the nucleic acid molecule is double-stranded DNA.

Isolated nucleic acid molecules also include nucleic acid molecules sufficient for use as hybridization probes or primers to identify nucleic acid molecules that correspond to a KIF5B-RET fusion, e.g., those suitable for use as PCR primers for the amplification or mutation of nucleic acid molecules.

An "isolated" nucleic acid molecule is one which is separated from other nucleic acid molecules which are present in the natural source of the nucleic acid molecule. In certain embodiments, an "isolated" nucleic acid molecule is free of sequences (such as protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, less than about 4 kB, less than about 3 kB, less than about 2 kB, less than about 1 kB, less than about 0.5 kB or less than about 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

The language "substantially free of other cellular material or culture medium" includes preparations of nucleic acid molecule in which the molecule is separated from cellular components of the cells from which it is isolated or recombinantly produced. Thus, nucleic acid molecule that is substantially free of cellular material includes preparations of nucleic acid molecule having less than about 30%, less than about 20%, less than about 10%, or less than about 5% (by dry weight) of other cellular material or culture medium.

A KIF5B-RET fusion nucleic acid molecule can be isolated using standard molecular biology techniques and the sequence information in the database records described herein. Using all or a portion of such nucleic acid sequences, KIF5B-RET fusion nucleic acid molecules can be isolated using standard hybridization and cloning techniques (e.g., as described in Sambrook et al., ed., *Molecular Cloning: A Laboratory Manual,* 2nd ed., Cold Spring Harbor Laboratory Press, Cold Spring Harbor, N Y, 1989).

A KIF5B-RET fusion nucleic acid molecule can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule of the invention can be prepared by standard synthetic techniques, e.g., using an automated DNA synthesizer.

In another embodiment, a KIF5B-RET fusion nucleic acid molecule comprises a nucleic acid molecule which has a nucleotide sequence complementary to the nucleotide sequence of a KIF5B-RET fusion nucleic acid molecule or to the nucleotide sequence of a nucleic acid encoding a KIF5B-RET fusion protein. A nucleic acid molecule which is complementary to a given nucleotide sequence is one which is sufficiently complementary to the given nucleotide sequence that it can hybridize to the given nucleotide sequence thereby forming a stable duplex.

Moreover, a KIF5B-RET fusion nucleic acid molecule can comprise only a portion of a nucleic acid sequence, wherein the full length nucleic acid sequence or which encodes a KIF5B-RET fusion polypeptide. Such nucleic acid molecules can be used, for example, as a probe or primer. The probe/primer typically is used as one or more substantially purified oligonucleotides. The oligonucleotide typically comprises a region of nucleotide sequence that hybridizes under stringent conditions to at least about 7, at least about 15, at least about 25, at least about 50, at least about 75, at least about 100, at least about 125, at least about 150, at least about 175, at least about 200, at least about 250, at least about 300, at least about 350, at least about 400, at least about 500, at least about 600, at least about 700, at least about 800, at least about 900, at least about 1 kb, at least about 2 kb, at least about 3 kb, at least about 4 kb, at least about 5 kb, at least about 6 kb, at least about 7 kb, at least about 8 kb, at least about 9 kb, at least about 10 kb, at least about 15 kb, at least about 20 kb, at least about 25 kb, at least about 30 kb, at least about 35 kb, at least about 40 kb, at least about 45 kb, at least about 50 kb, at least about 60 kb, at least about 70 kb, at least about 80 kb, at least about 90 kb, at least about 100 kb, at least about 200 kb, at least about 300 kb, at least about 400 kb, at least about 500 kb, at least about 600 kb, at least about 700 kb, at least about 800 kb, at least about 900 kb, at least about 1 mb, at least about 2 mb, at least about 3 mb, at least about 4 mb, at least about 5 mb, at least about 6 mb, at least about 7 mb, at least about 8 mb, at least about 9 mb, at least about 10 mb or more consecutive nucleotides of a KIF5B-RET fusion nucleic acid.

The invention further encompasses nucleic acid molecules that are substantially identical to the gene mutations and/or gene products described herein, e.g., KIF5B-RET fusion having a nucleotide sequence of SEQ ID NO:1 or 2, or an amino acid sequence of SEQ ID NO:3 or 4) such that they are at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5% or greater. In other embodiments, the invention further encompasses nucleic acid molecules that are substantially homologous to the KIF5B-RET fusion gene mutations and/or gene products described herein, such that they differ by only or at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 30, at least 40, at least 50, at least 60, at least 70, at least 80, at least 90, at least 100, at least 200, at least 300, at least 400, at least 500, at least 600 nucleotides or any range in between.

In another embodiment, an isolated KIF5B-RET fusion nucleic acid molecule is at least 7, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 250, at least 300, at least 350, at least 400, at least 450, at least 550, at least 650, at least 700, at least 800, at least 900, at least 1000, at least 1200, at least 1400, at least 1600, at least 1800, at least 2000, at least 2200, at least 2400, at least 2600, at least 2800, at least 3000, or more nucleotides in length and hybridizes under stringent conditions to a KIF5B-RET fusion nucleic acid molecule or to a nucleic acid molecule encoding a protein corresponding to a marker of the invention.

As used herein, the term "hybridizes under stringent conditions" is intended to describe conditions for hybridization and washing under which nucleotide sequences at least 60%, at least 65%, at least 70%, at least 75%, at least 80%, or at least 85% identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). Another, non-limiting example of stringent hybridization conditions are hybridization in 6× sodium chloride/sodium citrate (SSC) at about 45° C., followed by one or more washes in 0.2×SSC, 0.1% SDS at 50-65° C.

The invention also includes molecular beacon nucleic acid molecules having at least one region which is complementary to a KIF5B-RET fusion nucleic acid molecule, such that the molecular beacon is useful for quantitating the presence of the nucleic acid molecule of the invention in a sample. A "molecular beacon" nucleic acid is a nucleic acid molecule comprising a pair of complementary regions and having a fluorophore and a fluorescent quencher associated therewith. The fluorophore and quencher are associated with different portions of the nucleic acid in such an orientation that when the complementary regions are annealed with one another, fluorescence of the fluorophore is quenched by the quencher. When the complementary regions of the nucleic acid molecules are not annealed with one another, fluorescence of the fluorophore is quenched to a lesser degree. Molecular beacon nucleic acid molecules are described, for example, in U.S. Pat. No. 5,876,930.

Probes

The invention also provides isolated KIF5B-RET nucleic acid molecules useful as probes.

Probes based on the sequence of a KIF5B-RET fusion nucleic acid molecule can be used to detect transcripts or genomic sequences corresponding to one or more markers of the invention. The probe comprises a label group attached thereto, e.g., a radioisotope, a fluorescent compound, an enzyme, or an enzyme co-factor. Such probes can be used as part of a test kit for identifying cells or tissues which express the KIF5B-RET protein, such as by measuring levels of a nucleic acid molecule encoding the protein in a sample of cells from a subject, e.g., detecting mRNA levels or determining whether a gene encoding the protein has been mutated or deleted.

Probes featured in the invention include those that will specifically hybridize to a gene sequence described in the Example, e.g., a KIF5B-RET fusion. Typically these probes are 12 to 20, e.g., 17 to 20 nucleotides in length (longer for large insertions) and have the nucleotide sequence corresponding to the region of the mutations at their respective nucleotide locations on the gene sequence. Such molecules can be labeled according to any technique known in the art, such as with radiolabels, fluorescent labels, enzymatic labels, sequence tags, biotin, other ligands, etc. As used herein, a probe that "specifically hybridizes" to a KIF5B-RET fusion gene sequence will hybridize under high stringency conditions.

A probe will typically contain one or more of the specific mutations described herein. Typically, a nucleic acid probe will encompass only one mutation. Such molecules may be labeled and can be used as allele-specific probes to detect the mutation of interest.

In one aspect, the invention features a probe or probe set that specifically hybridizes to a nucleic acid comprising an inversion resulting in a KIF5B-RET fusion.

Isolated pairs of allele specific oligonucleotide probes are also provided, where the first probe of the pair specifically hybridizes to the mutant allele, and the second probe of the pair specifically hybridizes to the wildtype allele. For example, in one exemplary probe pair, one probe will recognize the fusion junction in the KI5B-RET fusion, and the other probe will recognize a sequence downstream or upstream of KIF5B or RET, neither of which includes the fusion junction. These allele-specific probes are useful in detecting a RET somatic mutation in a tumor sample, e.g., a lung tumor sample.

Primers

The invention also provides isolated nucleic acid molecules useful as primers.

The term "primer" as used herein refers to a sequence comprising two or more deoxyribonucleotides or ribonucleotides, e.g., more than three, and more than eight, or at least 20 nucleotides of a gene described in the Example, where the sequence corresponds to a sequence flanking one of the mutations or a wild type sequence of a gene identified in the Example, e.g., a KIF5B or RET gene. Primers may be used to initiate DNA synthesis via the PCR (polymerase chain reaction) or a sequencing method. Primers featured in the invention include the sequences recited and complementary sequences which would anneal to the opposite DNA strand of the sample target. Since both strands of DNA are complementary and mirror images of each other, the same segment of DNA will be amplified.

Primers can be used to sequence a nucleic acid, e.g., an isolated nucleic acid described herein, such as by an NGS method, or to amplify a gene described in the Example, such as by PCR. The primers can specifically hybridize, for example, to the ends of the exons or to the introns flanking the exons. The amplified segment can then be further analyzed for the presence of the mutation such as by a sequencing method. The primers are useful in directing amplification of a target polynucleotide prior to sequencing. In another aspect, the invention features a pair of oligonucleotide primers that amplify a region that contains or is adjacent to a fusion junction identified in the Example. Such primers are useful in directing amplification of a target region that includes a fusion junction identified in the Example, e.g., prior to sequencing. The primer typically contains 12 to 20, or 17 to 20, or more nucleotides, although a primer may contain fewer nucleotides.

A primer is typically single stranded, e.g., for use in sequencing or amplification methods, but may be double stranded. If double stranded, the primer may first be treated to separate its strands before being used to prepare extension products. A primer must be sufficiently long to prime the synthesis of extension products in the presence of the inducing agent for polymerization. The exact length of primer will depend on many factors, including applications (e.g., amplification method), temperature, buffer, and nucleotide composition. A primer typically contains 12-20 or more nucleotides, although a primer may contain fewer nucleotides.

Primers are typically designed to be "substantially" complementary to each strand of a genomic locus to be amplified. Thus, the primers must be sufficiently complementary to specifically hybridize with their respective strands under conditions which allow the agent for polymerization to perform. In other words, the primers should have sufficient complementarity with the 5' and 3' sequences flanking the mutation to hybridize therewith and permit amplification of the genomic locus.

The term "substantially complementary to" or "substantially the sequence" refers to sequences that hybridize to the sequences provided under stringent conditions and/or sequences having sufficient homology with a sequence comprising a fusion junction identified in the Example, or the wildtype counterpart sequence, such that the allele specific oligonucleotides hybridize to the sequence. In one embodiment, a sequence is substantially complementary to a fusion junction in an inversion event, e.g., to a fusion junction in SEQ ID NO:1. "Substantially the same" as it refers to oligonucleotide sequences also refers to the functional ability to hybridize or anneal with sufficient specificity to distinguish between the presence or absence of the mutation. This is measurable by the temperature of melting being sufficiently different to permit easy identification of whether the oligonucleotide is binding to the normal or mutant gene sequence identified in the Example.

In one aspect, the invention features a primer or primer set for amplifying a nucleic acid comprising an inversion resulting in a KIF5B-RET fusion.

Isolated pairs of allele specific oligonucleotide primer are also provided, where the first primer of the pair specifically hybridizes to the mutant allele, and the second primer of the pair specifically hybridizes to a sequence upstream or downstream of a mutation, or a fusion junction resulting from, e.g., an inversion, duplication, deletion, insertion or translocation. For example, in one exemplary primer pair, one probe will recognize the a KIF5B-RET inversion, such as by hybridizing to a sequence at the fusion junction between the KIF5B and RET transcripts, and the other primer will recognize a sequence upstream or downstream of the fusion junction. These allele-specific primers are useful for amplifying a KIF5B-RET fusion sequence from a tumor sample, e.g., an adenocarcinoma, such as an adenocarcinoma of the lung.

In another exemplary primer pair, one primer can recognize a RET-KIF5B inversion (e.g., the reciprocal of the KIF5B-RET inversion), such as by hybridizing to a sequence at the fusion junction between the RET and KIF5B transcripts, and the other primer will recognize a sequence upstream or downstream of the fusion junction. These allele-specific primers are useful for amplifying a RET-KIF5B fusion sequence from a tumor sample, e.g., an adenocarcinoma, such as an adenocarcinoma of the lung.

Primers can be prepared using any suitable method, such as conventional phosphotriester and phosphodiester methods or automated embodiments thereof. In one such automated embodiment, diethylphosphoramidites are used as starting materials and may be synthesized as described by Beaucage, et al., Tetrahedron Letters, 22:1859-1862, (1981).

One method for synthesizing oligonucleotides on a modified solid support is described in U.S. Pat. No. 4,458,066.

An oligonucleotide probe or primer that hybridizes to a mutant or wildtype allele is said to be the complement of the allele. As used herein, a probe exhibits "complete complementarity" when every nucleotide of the probe is complementary to the corresponding nucleotide of the allele. Two polynucleotides are said to be "minimally complementary" if they can hybridize to one another with sufficient stability to permit them to remain annealed to one another under at least conventional "low-stringency" conditions. Similarly, the polynucleotides are said to be "complementary" if they can hybridize to one another with sufficient stability to permit them to remain annealed to one another under conventional "high-stringency" conditions. Conventional stringency conditions are known to those skilled in the art and can be found, for example in *Molecular Cloning: A Laboratory Manual,* 3rd edition Volumes 1, 2, and 3. J. F. Sambrook, D. W. Russell, and N. Irwin, Cold Spring Harbor Laboratory Press, 2000.

Departures from complete complementarity are therefore permissible, as long as such departures do not completely preclude the capacity of a probe to hybridize to an allele. Thus, in order for a polynucleotide to serve as a primer or probe it need only be sufficiently complementary in sequence to be able to form a stable double-stranded structure under the particular solvent and salt concentrations employed. Appropriate stringency conditions which promote DNA hybridization are, for example, 6.0× sodium chloride/sodium citrate (SSC) at about 45° C., followed by a wash of 2.0×SSC at 50° C. Such conditions are known to those skilled in the art and can be found, for example in *Current Protocols in Molecular Biology,* John Wiley & Sons, N.Y. (1989). Salt concentration and temperature in the wash step can be adjusted to alter hybridization stringency. For example, conditions may vary from low stringency of about 2.0×SSC at 40° C. to moderately stringent conditions of about 2.0×SSC at 50° C. to high stringency conditions of about 0.2×SSC at 50° C.

KIF5B-RET Fusion Proteins and Antibodies

One aspect of the invention pertains to purified KIF5B-RET fusion polypeptides, and biologically active portions thereof. In one embodiment, the native KIF5B-RET fusion polypeptide can be isolated from cells or tissue sources by an appropriate purification scheme using standard protein purification techniques. In another embodiment, a KIF5B-RET fusion polypeptide is produced by recombinant DNA techniques. Alternative to recombinant expression, a KIF5B-RET fusion polypeptide can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, less than about 20%, less than about 10%, or less than about 5% (by dry weight) of heterologous protein (also referred to herein as a "contaminating protein"). When the protein or biologically active portion thereof is recombinantly produced, it can be substantially free of culture medium, i.e., culture medium represents less than about 20%, less than about 10%, or less than about 5% of the volume of the protein preparation. When the protein is produced by chemical synthesis, it can substantially be free of chemical precursors or other chemicals, i.e., it is separated from chemical precursors or other chemicals which are involved in the synthesis of the protein. Accordingly such preparations of the protein have less than about 30%, less than about 20%, less than about 10%, less than about 5% (by dry weight) of chemical precursors or compounds other than the polypeptide of interest.

Biologically active portions of a KIF5B-RET fusion polypeptide include polypeptides comprising amino acid sequences sufficiently identical to or derived from the amino acid sequence of the KIF5B-RET fusion protein, which include fewer amino acids than the full length protein, and exhibit at least one activity of the corresponding full-length protein, e.g., a kinase activity, or a dimerizing or multimerizing activity. A biologically active portion of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide.

In certain embodiments, the KIF5B-RET fusion polypeptide has an amino acid sequence of a protein encoded by a nucleic acid molecule disclosed herein. Other useful proteins are substantially identical (e.g., at least 60, at least 65, at least 70, at least 75, at least 80, at least 85, at least 86, at least 87, at least 88, at least 89, at least 90, at least 91, at least 92, at least 93, at least 94, at least 95, at least 96, at least 97, at least 98, at least 99, at least 99.5% or greater) to one of these sequences and retain the functional activity of the protein of the corresponding full-length protein yet differ in amino acid sequence.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. Another, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See online at ncbi.nlm.nih.gov. Another non-limiting example of a mathematical algorithm utilized for the comparison of sequences is the algorithm of Myers and Miller, (1988) *Comput Appl Biosci,* 4:11-7. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

An isolated KIF5B-RET fusion polypeptide, or a fragment thereof, can be used as an immunogen to generate antibodies using standard techniques for polyclonal and monoclonal antibody preparation. The full-length KIF5B-RET fusion polypeptide can be used or, alternatively, the invention provides antigenic peptide fragments for use as immunogens. The antigenic peptide of a protein of the invention comprises at least 8 (or at least 10, at least 15, at least 20, or at least 30 or more) amino acid residues of the amino acid sequence of one of the polypeptides of the invention, and encompasses an epitope of the protein such that an antibody raised against the peptide forms a specific immune complex with a marker of the invention to which the protein corresponds. Exemplary epitopes encompassed by the antigenic peptide are regions that are located on the surface of the protein, e.g., hydrophilic regions. Hydrophobicity sequence analysis, hydrophilicity sequence analysis, or similar analyses can be used to identify hydrophilic regions.

An immunogen typically is used to prepare antibodies by immunizing a suitable (i.e., immunocompetent) subject such as a rabbit, goat, mouse, or other mammal or vertebrate. An appropriate immunogenic preparation can contain, for example, recombinantly-expressed or chemically-synthesized polypeptide. The preparation can further include an adjuvant, such as Freund's complete or incomplete adjuvant, or a similar immunostimulatory agent.

Accordingly, another aspect of the invention pertains to antibodies directed against a KIF5B-RET fusion polypeptide. In one embodiment, the antibody molecule specifically binds to KIF5B-RET fusion, e.g., specifically binds to an epitope formed by the KIF5B-RET fusion. In embodiments the antibody can distinguish wild type RET (or KIF5B) from KIF5B-RET.

The terms "antibody" and "antibody molecule" as used interchangeably herein refer to immunoglobulin molecules and immunologically active portions of immunoglobulin molecules, i.e., molecules that contain an antigen binding site which specifically binds an antigen, such as a polypeptide of the invention. A molecule which specifically binds to a given polypeptide of the invention is a molecule which binds the polypeptide, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope.

Polyclonal antibodies can be prepared as described above by immunizing a suitable subject with a polypeptide of the invention as an immunogen. Antibody-producing cells can be obtained from the subject and used to prepare monoclonal antibodies by standard techniques, such as the hybridoma technique originally described by Kohler and Milstein (1975) *Nature* 256:495-497, the human B cell hybridoma technique (see Kozbor et al., 1983, *Immunol. Today* 4:72), the EBV-hybridoma technique (see Cole et al., pp. 77-96 In *Monoclonal Antibodies and Cancer Therapy*, Alan R. Liss, Inc., 1985) or trioma techniques. The technology for producing hybridomas is well known (see generally *Current Protocols in Immunology*, Coligan et al. ed., John Wiley & Sons, New York, 1994). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody can be identified and isolated by screening a recombinant combinatorial immunoglobulin library (e.g., an antibody phage display library) with the polypeptide of interest. Kits for generating and screening phage display libraries are commercially available (e.g., the *Pharmacia Recombinant Phage Antibody System*, Catalog No. 27-9400-01; and the Stratagene *SurfZAP Phage Display Kit*, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734.

Additionally, recombinant antibodies, such as chimeric and humanized monoclonal antibodies, comprising both human and non-human portions can be made using standard recombinant DNA techniques. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559; Morrison (1985) *Science* 229:1202-1207; Oi et al. (1986) *Bio/Techniques* 4:214; U.S. Pat. No. 5,225,539; Jones et al. (1986) *Nature* 321:552-525; Verhoeyan et al. (1988) *Science* 239: 1534; and Beidler et al. (1988) *J. Immunol.* 141:4053-4060.

Completely human antibodies can be produced using transgenic mice which are incapable of expressing endogenous immunoglobulin heavy and light chains genes, but which can express human heavy and light chain genes. For an overview of this technology for producing human antibodies, see Lonberg and Huszar (1995) *Int. Rev. Immunol.* 13:65-93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Freemont, Calif.), can be engaged to provide human antibodies directed against a selected antigen using technology similar to that described above.

An antibody directed against a KIF5B-RET fusion polypeptide (e.g., a monoclonal antibody) can be used to isolate the polypeptide by standard techniques, such as affinity chromatography or immunoprecipitation. Moreover, such an antibody can be used to detect the marker (e.g., in a cellular lysate or cell supernatant) in order to evaluate the level and pattern of expression of the marker. The antibodies can also be used diagnostically to monitor protein levels in tissues or body fluids (e.g., in a tumor cell-containing body fluid) as part of a clinical testing procedure, e.g., to, for example, determine the efficacy of a given treatment regimen. Detection can be facilitated by coupling the antibody to a detectable substance. Examples of detectable substances include, but are not limited to, various enzymes, prosthetic groups, fluorescent materials, luminescent materials, bioluminescent materials, and radioactive materials. Examples of suitable enzymes include, but are not limited to, horseradish peroxidase, alkaline phosphatase, β-galactosidase, or acetylcholinesterase; examples of suitable prosthetic group complexes include, but are not limited to, streptavidin/biotin and avidin/biotin; examples of suitable fluorescent materials include, but are not limited to, umbelliferone, fluorescein, fluorescein isothiocyanate, rhodamine, dichlorotriazinylamine fluorescein, dansyl chloride or phycoerythrin; an example of a luminescent material includes, but is not limited to, luminol; examples of bioluminescent materials include, but are not limited to, luciferase, luciferin, and aequorin, and examples of suitable radioactive materials include, but are not limited to, $^{125}$I, $^{131}$I, $^{35}$S or $^{3}$H.

Antigens and Vaccines

Embodiments of the invention include preparations, e.g., antigenic preparations, of the entire fusion or a fragment thereof, e.g., a fragment capable of raising antibodies specific to the fusion protein, e.g., a fusion junction containing fragment (collectively referred to herein as a fusion specific polypeptides or FSP). The preparation can include an adjuvant or other component.

An FSP can be used as an antigen or vaccine. E.g., an FSP can be used as an antigen to immunize an animal, e.g., a rodent, e.g., a mouse or rat, rabbit, horse, goat, dog, or non-human primate, to obtain antibodies, e.g., fusion protein specific antibodies. In an embodiment a fusion specific antibody molecule is an antibody molecule described herein, e.g., a polyclonal. In other embodiments a fusion specific antibody molecule is monospecific, e.g., monoclonal, human, humanized, chimeric or other monospecific antibody molecule. The fusion protein specific antibody molecules can be used to treat a subject having cancer, e.g., a cancer described herein.

Embodiments of the invention include vaccine preparations that comprise an FSP capable of stimulating an immune response in a subject, e.g., by raising, in the subject, antibodies specific to the fusion protein. The vaccine preparation can include other components, e.g., an adjuvant. The vaccine preparations can be used to treat a subject having cancer, e.g., a cancer described herein.

Expression Vectors, Host Cells and Recombinant Cells

In another aspect, the invention includes vectors (e.g., expression vectors), containing a nucleic acid encoding a KIF5B-RET fusion polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a KIF5B-RET fusion nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors can be introduced into host cells to thereby produce KIF5B-RET fusion polypeptide, including fusion proteins or polypeptides encoded by nucleic acids as described herein, mutant forms thereof, and the like).

The term "recombinant host cell" (or simply "host cell" or "recombinant cell"), as used herein, is intended to refer to a cell into which a recombinant expression vector has been introduced. It should be understood that such terms are intended to refer not only to the particular subject cell, but to the progeny of such a cell. Because certain modifications may occur in succeeding generations due to either mutation or environmental influences, such progeny may not, in fact, be identical to the parent cell, but are still included within the scope of the term "host cell" as used herein.

The recombinant expression vectors can be designed for expression of KIF5B-RET fusion polypeptide in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified KIF5B-RET fusion polypeptides can be used in activity assays (e.g., direct assays or competitive assays described in detail below), or to generate antibodies specific for KIF5B-RET fusion polypeptides.

To maximize recombinant protein expression in *E. coli* is to express the protein in a host bacteria with an impaired capacity to proteolytically cleave the recombinant protein (Gottesman, S., (1990) *Gene Expression Technology: Methods in Enzymology* 185, Academic Press, San Diego, Calif. 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

The KIF5B-RET fusion polypeptide expression vector can be a yeast expression vector, a vector for expression in insect cells, e.g., a baculovirus expression vector or a vector suitable for expression in mammalian cells.

When used in mammalian cells, the expression vector's control functions can be provided by viral regulatory elements. For example, commonly used promoters are derived from polyoma, Adenovirus 2, cytomegalovirus and Simian Virus 40.

In another embodiment, the promoter is an inducible promoter, e.g., a promoter regulated by a steroid hormone, by a polypeptide hormone (e.g., by means of a signal transduction pathway), or by a heterologous polypeptide (e.g., the tetracycline-inducible systems, "Tet-On" and "Tet-Off"; see, e.g., Clontech Inc., CA, Gossen and Bujard (1992) *Proc. Natl. Acad. Sci. USA* 89:5547, and Paillard (1989) *Human Gene Therapy* 9:983).

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873, 316 and European Application Publication No. 264,166). Developmentally-regulated promoters are also encompassed, for example, the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus.

Another aspect the invention provides a host cell which includes a nucleic acid molecule described herein, e.g., a KIF5B-RET fusion nucleic acid molecule within a recombinant expression vector or a KIF5B-RET fusion nucleic acid molecule containing sequences which allow it to homologous recombination into a specific site of the host cell's genome.

A host cell can be any prokaryotic or eukaryotic cell. For example, a KIF5B-RET fusion polypeptide can be expressed in bacterial cells (such as *E. coli*), insect cells, yeast or mammalian cells (such as Chinese hamster ovary cells (CHO) or COS cells, e.g., COS-7 cells, CV-1 origin SV40 cells; Gluzman (1981) *Cell* 23:175-182). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell can be used to produce (e.g., express) a KIF5B-RET fusion polypeptide. Accordingly, the invention further provides methods for producing a KIF5B-RET fusion polypeptide using the host cells. In one embodiment, the method includes culturing the host cell of the invention (into which a recombinant expression vector encoding a KIF5B-RET fusion polypeptide has been introduced) in a suitable medium such that a KIF5B-RET fusion polypeptide is produced. In another embodiment, the method further includes isolating a KIF5B-RET fusion polypeptide from the medium or the host cell.

In another aspect, the invention features, a cell or purified preparation of cells which include a KIF5B-RET fusion transgene, or which otherwise misexpress KIF5B-RET fusion. The cell preparation can consist of human or non-human cells, e.g., rodent cells, e.g., mouse or rat cells, rabbit cells, or pig cells. In embodiments, the cell or cells include a KIF5B-RET fusion transgene, e.g., a heterologous form of a KIF5B-RET fusion, e.g., a gene derived from humans (in the case of a non-human cell). The KIF5B-RET fusion transgene can be misexpressed, e.g., overexpressed or underexpressed. In other preferred embodiments, the cell or cells include a gene that mis-expresses an endogenous KIF5B-RET fusion, e.g., a gene the expression of which is disrupted, e.g., a knockout. Such cells can serve as a model for studying disorders that are related to mutated or mis-expressed KIF5B-RET fusion alleles (e.g., cancers) or for use in drug screening, as described herein.

Therapeutic Methods

Alternatively, or in combination with the methods described herein, the invention features a method of treating a cancer or tumor harboring a KIF5B-RET fusion described herein. The methods include administering an anti-cancer agent, e.g., a kinase inhibitor, alone or in combination, e.g., in combination with other chemotherapeutic agents or procedures, in an amount sufficient to reduce or inhibit the tumor cell growth, and/or treat or prevent the cancer(s), in the subject.

"Treat," "treatment," and other forms of this word refer to the administration of a kinase inhibitor, alone or in combination with a second agent to impede growth of a cancer, to cause a cancer to shrink by weight or volume, to extend the expected survival time of the subject and or time to progression of the tumor or the like. In those subjects, treatment can include, but is not limited to, inhibiting tumor growth, reducing tumor mass, reducing size or number of metastatic lesions, inhibiting the development of new metastatic lesions, prolonged survival, prolonged progression-free survival, prolonged time to progression, and/or enhanced quality of life.

As used herein, unless otherwise specified, the terms "prevent," "preventing" and "prevention" contemplate an action that occurs before a subject begins to suffer from the re-growth of the cancer and/or which inhibits or reduces the severity of the cancer.

As used herein, and unless otherwise specified, a "therapeutically effective amount" of a compound is an amount sufficient to provide a therapeutic benefit in the treatment or management of the cancer, or to delay or minimize one or more symptoms associated with the cancer. A therapeutically effective amount of a compound means an amount of therapeutic agent, alone or in combination with other therapeutic agents, which provides a therapeutic benefit in the treatment or management of the cancer. The term "therapeutically effective amount" can encompass an amount that improves overall therapy, reduces or avoids symptoms or causes of the cancer, or enhances the therapeutic efficacy of another therapeutic agent.

As used herein, and unless otherwise specified, a "prophylactically effective amount" of a compound is an amount sufficient to prevent re-growth of the cancer, or one or more symptoms associated with the cancer, or prevent its recurrence. A prophylactically effective amount of a compound means an amount of the compound, alone or in combination with other therapeutic agents, which provides a prophylactic benefit in the prevention of the cancer. The term "prophylactically effective amount" can encompass an amount that improves overall prophylaxis or enhances the prophylactic efficacy of another prophylactic agent.

As used herein, the term "patient" or "subject" refers to an animal, typically a human (i.e., a male or female of any age group, e.g., a pediatric patient (e.g, infant, child, adolescent) or adult patient (e.g., young adult, middle-aged adult or senior adult) or other mammal, such as a primate (e.g., cynomolgus monkey, rhesus monkey); commercially relevant mammals such as cattle, pigs, horses, sheep, goats, cats, and/or dogs; and/or birds, including commercially relevant birds such as chickens, ducks, geese, and/or turkeys, that will be or has been the object of treatment, observation, and/or experiment. When the term is used in conjunction with administration of a compound or drug, then the patient has been the object of treatment, observation, and/or administration of the compound or drug.

In certain embodiments, the cancer includes, but is not limited to, a solid tumor, a soft tissue tumor, and a metastatic lesion (e.g., a cancer as described herein). In one embodiment, the cancer is chosen from a lung cancer, a pancreatic cancer, melanoma, a colorectal cancer, an esophageal-gastric cancer, a thyroid cancer, or an adenocarcinoma. In other embodiment, the lung cancer is chosen from one or more of the following: non-small cell lung cancer (NSCLC), small cell lung cancer (SCLC), squamous cell carcinoma (SCC), adenocarcinoma of the lung, bronchogenic carcinoma, or a combination thereof. In one embodiment, the lung cancer is NSCLC or SCC.

In other embodiments, the cancer is chosen from lung cancer, thyroid cancer, colorectal cancer, adenocarcinoma, melanoma, B cell cancer, breast cancer, bronchus cancer, cancer of the oral cavity or pharynx, cancer of hematological tissues, cervical cancer, colon cancer, esophageal cancer, esophageal-gastric cancer, gastric cancer, kidney cancer, liver cancer, multiple myeloma, ovarian cancer, pancreatic cancer, prostate cancer, salivary gland cancer, small bowel or appendix cancer, stomach cancer, testicular cancer, urinary bladder cancer, uterine or endometrial cancer, inflammatory myofibroblastic tumors, gastrointestinal stromal tumor (GIST), and the like.

In one embodiment, the anti-cancer agent is a kinase inhibitor. For example, the kinase inhibitor is a multi-kinase inhibitor or a RET-specific inhibitor. Exemplary kinase inhibitors include, but are not limited to, axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), lenvatinib (E7080), neratinib (HKI-272), nilotinib (TASIGNA®), semaxanib (semaxinib, SU5416), sunitinib (SUTENT®, SU11248), toceranib (PALLADIA®), vandetanib, vatalanib (PTK787, PTK/ZK), sorafenib (NEXAVAR®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and XL228.

In one embodiment, the kinase inhibitor is chosen from lenvatinib (E7080), sorafenib (NEXAVAR®), sunitinib (SUTENT®, SU11248), vandetanib (CAPRELSA®, ZACTIMA®, ZD6474), NVP-AST487, regorafenib (BAY-73-4506), motesanib (AMG 706), cabozantinib (XL-184), apatinib (YN-968D1), DCC-2157, or AST-487.

In other embodiments, the anti-cancer agent is a KIF5B-RET antagonist inhibits the expression of nucleic acid encoding KIF5B-RET. Examples of such KIF5B-RET antagonists include nucleic acid molecules, for example, antisense molecules, ribozymes, RNAi, triple helix molecules that hybridize to a nucleic acid encoding KIF5B-RET, or a transcription regulatory region, and blocks or reduces mRNA expression of KIF5B-RET.

In other embodiments, the kinase inhibitor is administered in combination with a second therapeutic agent or a different therapeutic modality, e.g., anti-cancer agents, and/or in combination with surgical and/or radiation procedures.

By "in combination with," it is not intended to imply that the therapy or the therapeutic agents must be administered at the same time and/or formulated for delivery together, although these methods of delivery are within the scope of the invention. The pharmaceutical compositions can be administered concurrently with, prior to, or subsequent to, one or more other additional therapies or therapeutic agents. In general, each agent will be administered at a dose and/or on a time schedule determined for that agent. In will further be appreciated that the additional therapeutic agent utilized in this combination can be administered together in a single composition or administered separately in different compositions. The particular combination to employ in a regimen will take into account compatibility of the inventive pharmaceutical composition with the additional therapeutically active agent and/or the desired therapeutic effect to be achieved.

For example, the second therapeutic agent can be a a cytotoxic or a cytostatic agent. Exemplary cytotoxic agents include antimicrotubule agents, topoisomerase inhibitors, or taxanes, antimetabolites, mitotic inhibitors, alkylating agents, intercalating agents, agents capable of interfering with a signal transduction pathway, agents that promote apoptosis and radiation. In yet other embodiments, the methods can be used in combination with immunodulatory agents, e.g., IL-1, 2, 4, 6, or 12, or interferon alpha or gamma, or immune cell growth factors such as GM-CSF.

Anti-cancer agents, e.g., kinase inhibitors, used in the therapeutic methods of the invention can be evaluated using the screening assays described herein. In one embodiment, the anti-cancer agents are evaluated in a cell-free system, e.g., a cell lysate or in a reconstituted system. In other embodiments, the anti-cancer agents are evaluated in a cell in culture, e.g., a cell expressing a KIF5B-RET fusion (e.g., a mammalian cell, a tumor cell or cell line, a recombinant cell). In yet other embodiments, the anti-cancer agents are evaluated cell in vivo (a KIF5B-RET-expressing cell present in a subject, e.g., an animal subject (e.g., an in vivo animal model).

Exemplary parameters evaluated include one or more of:

(i) a change in binding activity, e.g., direct binding of the candidate agent to a KIF5B-RET fusion polypeptide; a binding competition between a known ligand and the candidate agent to a KIF5B-RET fusion polypeptide;

(ii) a change in kinase activity, e.g., phosphorylation levels of a KIF5B-RET fusion polypeptide (e.g., an increased or decreased autophosphorylation); or a change in phosphorylation of a target of a RET kinase, e.g., focal adhesion kinase (FAK), persephin or glial derived neurotrophic factor (GDNF);

(iii) a change in an activity of a cell containing a KIF5B-RET fusion (e.g., a tumor cell or a recombinant cell), e.g., a change in proliferation, morphology or tumorigenicity of the cell;

(iv) a change in tumor present in an animal subject, e.g., size, appearance, proliferation, of the tumor; or (v) a change in the level, e.g., expression level, of a KIF5B-RET fusion polypeptide or nucleic acid molecule.

In one embodiment, a change in a cell free assay in the presence of a candidate agent is evaluated. For example, an activity of a KIF5B-RET fusion, or interaction of a KIF5B-RET fusion with a downstream ligand can be detected.

In other embodiments, a change in an activity of a cell is detected in a cell in culture, e.g., a cell expressing a KIF5B-RET fusion (e.g., a mammalian cell, a tumor cell or cell line, a recombinant cell). In one embodiment, the cell is a recombinant cell that is modified to express a KIF5B-RET fusion nucleic acid, e.g., is a recombinant cell transfected with a KIF5B-RET fusion nucleic acid. The transfected cell can show a change in response to the expressed KIF5B-RET fusion, e.g., increased proliferation, changes in morphology, increased tumorigenicity, and/or acquired a transformed phenotype. A change in any of the activities of the cell, e.g., the recombinant cell, in the presence of the candidate agent can be detected. For example, a decrease in one or more of: proliferation, tumorigenicity, transformed morphology, in the presence of the candidate agent can be indicative of an inhibitor of a KIF5B-RET fusion. In other embodiments, a change in binding activity or phosphorylation as described herein is detected.

In yet other embodiment, a change in a tumor present in an animal subject (e.g., an in vivo animal model) is detected. In one embodiment, the animal model is a tumor containing animal or a xenograft comprising cells expressing a KIF5B-RET fusion (e.g., tumorigenic cells expressing a KIF5B-RET fusion). The anti-cancer agents can be administered to the animal subject and a change in the tumor is detected. In one embodiment, the change in the tumor includes one or more of a tumor growth, tumor size, tumor burden, survival, is evaluated. A decrease in one or more of tumor growth, tumor size, tumor burden, or an increased survival is indicative that the candidate agent is an inhibitor.

The screening methods and assays are described in more detail herein below.

Screening Methods

In another aspect, the invention features a method, or assay, for screening for agents that modulate, e.g., inhibit, the expression or activity of a KIF5B-RET fusion, e.g., a KIF5B-RET fusion as described herein. The method includes contacting a KIF5B-RET fusion, or a cell expressing a KIF5B-RET fusion, with a candidate agent; and detecting a change in a parameter associated with a KIF5B-RET fusion, e.g., a change in the expression or an activity of the KIF5B-RET fusion. The method can, optionally, include comparing the treated parameter to a reference value, e.g., a control sample (e.g., comparing a parameter obtained from a sample with the candidate agent to a parameter obtained from a sample without the candidate agent). In one embodiment, if a decrease in expression or activity of the KIF5B-RET fusion is detected, the candidate agent is identified as an inhibitor. In another embodiment, if an increase in expression or activity of the KIF5B-RET fusion is detected, the candidate agent is identified as an activator. In certain embodiments, the KIF5B-RET fusion is a nucleic acid molecule or a polypeptide as described herein.

In one embodiment, the contacting step is effected in a cell-free system, e.g., a cell lysate or in a reconstituted system. In other embodiments, the contacting step is effected in a cell in culture, e.g., a cell expressing a KIF5B-RET fusion (e.g., a mammalian cell, a tumor cell or cell line, a recombinant cell). In yet other embodiments, the contacting step is effected in a cell in vivo (a KIF5B-RET-expressing cell present in a subject, e.g., an animal subject (e.g., an in vivo animal model).

Exemplary parameters evaluated include one or more of:

(i) a change in binding activity, e.g., direct binding of the candidate agent to a KIF5B-RET fusion polypeptide; a binding competition between a known ligand and the candidate agent to a KIF5B-RET fusion polypeptide;

(ii) a change in kinase activity, e.g., phosphorylation levels of a KIF5B-RET fusion polypeptide (e.g., an increased or decreased autophosphorylation); or a change in phosphorylation of a target of a RET kinase, e.g., focal adhesion kinase (FAK), persephin or glial derived neurotrophic factor (GDNF). In certain embodiments, a change in kinase activity, e.g., phosphorylation, is detected by any of Western blot (e.g., using an anti-KIF5B or anti-RET antibody; a phosphor-specific antibody, detecting a shift in the molecular weight of a KIF5B-RET fusion polypeptide), mass spectrometry, immunoprecipitation, immunohistochemistry, immunomagnetic beads, among others;

(iii) a change in an activity of a cell containing a KIF5B-RET fusion (e.g., a tumor cell or a recombinant cell), e.g., a change in proliferation, morphology or tumorigenicity of the cell;

(iv) a change in tumor present in an animal subject, e.g., size, appearance, proliferation, of the tumor; or (v) a change in the level, e.g., expression level, of a KIF5B-RET fusion polypeptide or nucleic acid molecule.

In one embodiment, a change in a cell free assay in the presence of a candidate agent is evaluated. For example, an activity of a KIF5B-RET fusion, or interaction of a KIF5B-RET fusion with a downstream ligand can be detected. In one embodiment, a KIF5B-RET fusion polypeptide is contacted with a ligand, e.g., in solution, and a candidate agent is monitored for an ability to modulate, e.g., inhibit, an interaction, e.g., binding, between the KIF5B-RET fusion polypeptide and the ligand. In one exemplary assay, purified KIF5B-RET fusion protein is contacted with a ligand, e.g., in solution, and a candidate agent is monitored for an ability to inhibit interaction of the fusion protein with the ligand, or to inhibit phosphorylation of the ligand by the fusion protein. An effect on an interaction between the fusion protein and a ligand can be monitored by methods known in the art, such as by absorbance, and an effect on phosphorylation of the ligand can be assayed, e.g., by Western blot, immunoprecipitation, or immunomagnetic beads.

In other embodiments, a change in an activity of a cell is detected in a cell in culture, e.g., a cell expressing a KIF5B-RET fusion (e.g., a mammalian cell, a tumor cell or cell line, a recombinant cell). In one embodiment, the cell is a recombinant cell that is modified to express a KIF5B-RET fusion nucleic acid, e.g., is a recombinant cell transfected with a KIF5B-RET fusion nucleic acid. The transfected cell can show a change in response to the expressed KIF5B-RET fusion, e.g., increased proliferation, changes in morphology, increased tumorigenicity, and/or acquired a transformed phenotype. A change in any of the activities of the cell, e.g., the recombinant cell, in the presence of the candidate agent can be detected. For example, a decrease in one or more of: proliferation, tumorigenicity, transformed morphology, in the presence of the candidate agent can be indicative of an inhibitor of a KIF5B-RET fusion. In other embodiments, a change in binding activity or phosphorylation as described herein is detected.

In an exemplary cell-based assay, a nucleic acid comprising a KIF5B-RET fusion can be expressed in a cell, such as a cell (e.g., a mammalian cell) in culture. The cell containing a nucleic acid expressing the KIF5B-RET fusion can be contacted with a candidate agent, and the cell is monitored for an effect of the candidate agent. A candidate agent that causes decreased cell proliferation or cell death can be determined to be a candidate for treating a tumor (e.g., a cancer) that carries a KIF5B-RET fusion.

In one embodiment, a cell containing a nucleic acid expressing a KIF5B-RET fusion can be monitored for expression of the KIF5B-RET fusion protein. Protein expression can be monitored by methods known in the art, such as by, e.g., mass spectrometry (e.g., tandem mass spectrometry), a reporter assay (e.g., a fluorescence-based assay), Western blot, and immunohistochemistry. By one method, decreased KIF5B-RET expression is detected. A candidate agent that causes decreased expression of the KIF5B-RET fusion protein as compared to a cell that does not contain the KIF5B-RET nucleic acid fusion can be determined to be a candidate for treating a tumor (e.g., a cancer) that carries a KIF5B-RET fusion.

A cell containing a nucleic acid expressing a KIF5B-RET fusion can be monitored for altered KIF5B-RET kinase activity. Kinase activity can be assayed by measuring the effect of a candidate agent on a known RET kinase target protein, such as focal adhesion kinase (FAK), persephin or GDNF (glial-cell-line-derived neurotrophic factor).

In yet other embodiment, a change in a tumor present in an animal subject (e.g., an in vivo animal model) is detected. In one embodiment, the animal model is a tumor containing animal or a xenograft comprising cells expressing a KIF5B-RET fusion (e.g., tumorigenic cells expressing a KIF5B-RET fusion). The candidate agent can be administered to the animal subject and a change in the tumor is detected. In one embodiment, the change in the tumor includes one or more of a tumor growth, tumor size, tumor burden, survival, is evaluated. A decrease in one or more of tumor growth, tumor size, tumor burden, or an increased survival is indicative that the candidate agent is an inhibitor.

In one exemplary animal model, a xenograft is created by injecting cells into mouse. A candidate agent is administered to the mouse, e.g., by injection (such as subcutaneous, intraperitoneal, or tail vein injection, or by injection directly into the tumor) or oral delivery, and the tumor is observed to determine an effect of the candidate anti-cancer agent. The health of the animal is also monitored, such as to determine if an animal treated with a candidate agent survives longer. A candidate agent that causes growth of the tumor to slow or stop, or causes the tumor to shrink in size, or causes decreased tumor burden, or increases survival time, can be considered to be a candidate for treating a tumor (e.g., a cancer) that carries a KIF5B-RET fusion.

In another exemplary animal assay, cells expressing a KIF5B-RET fusion are injected into the tail vein, e.g., of a mouse, to induce metastasis. A candidate agent is administered to the mouse, e.g., by injection (such as subcutaneous, intraperitoneal, or tail vein injection, or by injection directly into the tumor) or oral delivery, and the tumor is observed to determine an effect of the candidate anti-cancer agent. A candidate agent that inhibits or prevents or reduces metastasis, or increases survival time, can be considered to be a candidate for treating a tumor (e.g., a cancer) that carries a KIF5B-RET fusion.

Cell proliferation can be measured by methods known in the art, such as PCNA (Proliferating cell nuclear antigen) assay, 5-bromodeoxyuridine (BrdUrd) incorporation, Ki-67 assay, mitochondrial respiration, or propidium iodide staining. Cells can also be measured for apoptosis, such as by use of a TUNEL (Terminal Deoxynucleotide Transferase dUTP Nick End Labeling) assay. Cells can also be assayed for presence of angiogenesis using methods known in the art, such as by measuring endothelial tube formation or by measuring the growth of blood vessels from subcutaneous tissue, such as into a solid gel of basement membrane.

In other embodiments, a change in expression of a KIF5B-RET fusion can be monitored by detecting the nucleic acid or protein levels, e.g., using the methods described herein.

In certain embodiments, the screening methods described herein can be repeated and/or combined. In one embodiment, a candidate agent that is evaluated in a cell-free or cell-based described herein can be further tested in an animal subject.

In one embodiment, the candidate agent is identified and re-tested in the same or a different assay. For example, a test compound is identified in an in vitro or cell-free system, and re-tested in an animal model or a cell-based assay. Any order or combination of assays can be used. For example, a high throughput assay can be used in combination with an animal model or tissue culture.

Candidate agents suitable for use in the screening assays described herein include, e.g., small molecule compounds, nucleic acids (e.g., siRNA, aptamers, short hairpin RNAs, antisense oligonucleotides, ribozymes, antagomirs, microRNA mimics or DNA, e.g., for gene therapy) or polypeptides, e.g., antibodies (e.g., full length antibodies or antigen-binding fragments thereof, Fab fragments, or scFv fragments). The candidate anti-cancer agents can be obtained from a library (e.g., a commercial library), or can be rationally designed, such as to target an active site in a functional domain of RET (e.g., the kinase domain of RET), or a functional domain of KIF5B (e.g., the oligomerization domain or the kinesin domain).

In other embodiments, the method, or assay, includes providing a step based on proximity-dependent signal generation, e.g., a two-hybrid assay that includes a first fusion protein (e.g., a KIF5B-RET fusion protein), and a second fusion protein (e.g., a ligand), contacting the two-hybrid assay with a test compound, under conditions wherein said two hybrid assay detects a change in the formation and/or stability of the complex, e.g., the formation of the complex initiates transcription activation of a reporter gene.

In one non-limiting example, the three-dimensional structure of the active site of KIF5B-RET fusion is determined by crystallizing the complex formed by the KIF5B-RET fusion and a known inhibitor. Rational drug design is then used to identify new test agents by making alterations in the structure of a known inhibitor or by designing small molecule compounds that bind to the active site of the KIF5B-RET fusion.

The candidate agents can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner, U.S. Pat. No. 5,223,409), spores (Ladner U.S. Pat. No. 5,223,409), plasmids (Cull et al. (1992) *Proc Natl Acad Sci USA* 89:1865-1869) or on phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.).

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means known in the art (e.g., using a fluorimeter).

In another embodiment, determining the ability of the KIF5B-RET fusion protein to bind to a target molecule can be accomplished using real-time Biomolecular Interaction Analysis (BIA) (see, e.g., Sjolander, S. and Urbaniczky, C. (1991) *Anal. Chem.* 63:2338-2345 and Szabo et al. (1995) *Curr. Opin. Struct. Biol.* 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Nucleic Acid Inhibitors

In yet another embodiment, the KIF5B-RET fusion inhibitor inhibits the expression of nucleic acid encoding a KIF5B-RET fusion. Examples of such KIF5B-RET fusion inhibitors include nucleic acid molecules, for example, antisense molecules, ribozymes, siRNA, triple helix molecules that hybridize to a nucleic acid encoding a KIF5B-RET fusion, or a transcription regulatory region, and blocks or reduces mRNA expression of the KIF5B-RET fusion.

In one embodiment, the nucleic acid antagonist is a siRNA that targets mRNA encoding KIF5B-RET fusion. Other types of antagonistic nucleic acids can also be used, e.g., a dsRNA, a ribozyme, a triple-helix former, or an antisense nucleic acid. Accordingly, isolated nucleic acid molecules that are nucleic acid inhibitors, e.g., antisense, RNAi, to a KIF5B-RET fusion-encoding nucleic acid molecule are provided.

An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire KIF5B-RET fusion coding strand, or to only a portion thereof. In another embodiment, the antisense nucleic acid molecule is antisense to a "noncoding region" of the coding strand of a nucleotide sequence encoding KIF5B-RET fusion (e.g., the 5' and 3' untranslated regions). Anti-sense agents can include, for example, from about 8 to about 80 nucleobases (i.e. from about 8 to about 80 nucleotides), e.g., about 8 to about 50 nucleobases, or about 12 to about 30 nucleobases. Anti-sense compounds include ribozymes, external guide sequence (EGS) oligonucleotides (oligozymes), and other short catalytic RNAs or catalytic oligonucleotides which hybridize to the target nucleic acid and modulate its expression. Anti-sense compounds can include a stretch of at least eight consecutive nucleobases that are complementary to a sequence in the target gene. An oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA can interfere with one or more of the normal functions of mRNA. The functions of mRNA to be interfered with include all key functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

Exemplary antisense compounds include DNA or RNA sequences that specifically hybridize to the target nucleic acid, e.g., the mRNA encoding KIF5B-RET fusion. The complementary region can extend for between about 8 to about 80 nucleobases. The compounds can include one or more modified nucleobases. Modified nucleobases are known in the art. Descriptions of modified nucleic acid agents are also available. See, e.g., U.S. Pat. Nos. 4,987,071; 5,116,742; and U.S. Pat. No. 5,093,246; Woolf et al. (1992) *Proc Natl Acad Sci USA; Antisense RNA and DNA*, D. A. Melton, Ed., Cold Spring Harbor Laboratory, Cold Spring Harbor, N.Y. (1988); 89:7305-9; Haselhoff and Gerlach (1988) *Nature* 334:585-59; Helene, C. (1991) *Anticancer Drug Des.* 6:569-84; Helene (1992) *Ann. N.Y. Acad. Sci.* 660:27-36; and Maher (1992) Bioassays 14:807-15.

The antisense nucleic acid molecules of the invention are typically administered to a subject (e.g., by direct injection at a tissue site), or generated in situ such that they hybridize with or bind to cellular mRNA and/or genomic DNA encoding a KIF5B-RET fusion to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.*

15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215: 327-330).

siRNAs are small double stranded RNAs (dsRNAs) that optionally include overhangs. For example, the duplex region of an siRNA is about 18 to 25 nucleotides in length, e.g., about 19, 20, 21, 22, 23, or 24 nucleotides in length. Typically, the siRNA sequences are exactly complementary to the target mRNA. dsRNAs and siRNAs in particular can be used to silence gene expression in mammalian cells (e.g., human cells). siRNAs also include short hairpin RNAs (shRNAs) with 29-base-pair stems and 2-nucleotide 3' overhangs. See, e.g., Clemens et al. (2000) *Proc. Natl. Acad. Sci. USA* 97:6499-6503; Billy et al. (2001) Proc. Natl. Sci. USA 98:14428-14433; Elbashir et al. (2001) *Nature.* 411:494-8; Yang et al. (2002) *Proc. Natl. Acad. Sci. USA* 99:9942-9947; Siolas et al. (2005), *Nat. Biotechnol.* 23(2):227-31; 20040086884; U.S. 20030166282; 20030143204; 20040038278; and 20030224432.

In still another embodiment, an antisense nucleic acid of the invention is a ribozyme. A ribozyme having specificity for a KIF5B-RET fusion-encoding nucleic acid can include one or more sequences complementary to the nucleotide sequence of a KIF5B-RET fusion cDNA disclosed herein (i.e., SEQ ID NO:1 or SEQ ID NO:3), and a sequence having known catalytic sequence responsible for mRNA cleavage (see U.S. Pat. No. 5,093,246 or Haselhoff and Gerlach (1988) Nature 334:585-591). For example, a derivative of a Tetrahymena L-19 IVS RNA can be constructed in which the nucleotide sequence of the active site is complementary to the nucleotide sequence to be cleaved in a KIF5B-RET fusion-encoding mRNA. See, e.g., Cech et al. U.S. Pat. No. 4,987,071; and Cech et al. U.S. Pat. No. 5,116,742. Alternatively, KIF5B-RET fusion mRNA can be used to select a catalytic RNA having a specific ribonuclease activity from a pool of RNA molecules. See, e.g., Bartel, D. and Szostak, J. W. (1993) Science 261:1411-1418.

KIF5B-RET fusion gene expression can be inhibited by targeting nucleotide sequences complementary to the regulatory region of the KIF5B-RET fusion to form triple helical structures that prevent transcription of the KIF5B-RET fusion gene in target cells. See generally, Helene, C. (1991) *Anticancer Drug Des.* 6:569-84; Helene, C. i (1992) *Ann. N.Y. Acad. Sci.* 660:27-36; and Maher, L. J. (1992) *Bioassays* 14:807-15. The potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A KIF5B-RET fusion nucleic acid molecule can be modified at the base moiety, sugar moiety or phosphate backbone to improve, e.g., the stability, hybridization, or solubility of the molecule. For non-limiting examples of synthetic oligonucleotides with modifications see Toulmé (2001) *Nature Biotech.* 19:17 and Faria et al. (2001) *Nature Biotech.* 19:40-44. Such phosphoramidite oligonucleotides can be effective antisense agents.

For example, the deoxyribose phosphate backbone of the nucleic acid molecules can be modified to generate peptide nucleic acids (see Hyrup B. et al. (1996) *Bioorganic & Medicinal Chemistry* 4: 5-23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra and Perry-O'Keefe et al. *Proc. Natl. Acad. Sci.* 93: 14670-675.

PNAs of KIF5B-RET fusion nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of KIF5B-RET fusion nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. et al. (1996) supra)); or as probes or primers for DNA sequencing or hybridization (Hyrup B. et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; WO88/09810) or the blood-brain barrier (see, e.g., WO 89/10134). In addition, oligonucleotides can be modified with hybridization-triggered cleavage agents (see, e.g., Krol et al. (1988) *Bio-Techniques* 6:958-976) or intercalating agents (See, e.g., Zon (1988) *Pharm. Res.* 5:539-549). To this end, the oligonucleotide may be conjugated to another molecule, (e.g., a peptide, hybridization triggered cross-linking agent, transport agent, or hybridization-triggered cleavage agent).

Evaluation of Subjects

Subjects, e.g., patients, can be evaluated for the presence of a KIF5B-RET fusion. A patient can be evaluated, for example, by determining the genomic sequence of the patient, e.g., by an NGS method. Alternatively, or in addition, evaluation of a patient can include directly assaying for the presence of a KIF5B-RET fusion in the patient, such as by an assay to detect a KIF5B-RET nucleic acid (e.g., DNA or RNA), such as by, Southern blot, Northern blot, or RT-PCR, e.g., qRT-PCR. Alternatively, or in addition, a patient can be evaluated for the presence of a KIF5B-RET protein fusion, such as by immunohistochemistry, Western blot, immunoprecipitation, or immunomagnetic bead assay.

Evaluation of a patient can also include a cytogenetic assay, such as by fluorescence in situ hybridization (FISH), to identify the chromosomal rearrangement resulting in the KIF5B-RET fusion. For example, to perform FISH, at least a first probe tagged with a first detectable label can be designed to target KIF5B, such as in one or more of exons 1-15 of KIF5B (e.g., the exons containing the part of the protein that includes the kinesin motor domain and the oligomeric domain), and at least a second probe tagged with a second detectable label can be designed to target RET, such as in one or more of exons 12-25 of RET (e.g., the exons containing the part of the protein that includes the tyrosine kinase domain). The at least one first probe and the at least one second probe will be closer together in patients who carry the KIF5B-RET fusion than in patients who do not carry the KIF5B-RET fusion.

Additional methods for KIF5B-RET fusion detection are provided below.

In one aspect, the results of a clinical trial, e.g., a successful or unsuccessful clinical trial, can be repurposed to identify agents that target a KIF5B-RET fusion. By one exemplary method, a candidate agent used in a clinical trial can be reevaluated to determine if the agent in the trial targets a KIF5B-RET fusion, or is effective to treat a tumor containing a KIF5B-RET fusion. For example, subjects who participated in a clinical trial for an agent, such as a kinase inhibitor, can be identified. Patients who experienced an improvement in symptoms, e.g., cancer (e.g., lung cancer) symptoms, such as decreased tumor size, or decreased rate of tumor growth, can be evaluated for the presence of a KIF5B-RET fusion. Patients who did not experience an improvement in cancer symptoms can also be evaluated for the presence of a KIF5B-RET fusion. Where patients carrying a KIF5B-RET fusion are found to have been more likely to respond to the test agent than patients who did not carry a KIF5B-RET fusion, then the agent is determined to be an appropriate treatment option for a patient carrying the KIF5B-RET fusion.

"Reevaluation" of patients can include, for example, determining the genomic sequence of the patients, or a subset of the clinical trial patients, e.g., by an NGS method. Alternatively, or in addition, reevaluation of the patients can include directly assaying for the presence of a KIF5B-RET fusion in the patient, such as by an assay to detect a KIF5B-RET nucleic acid (e.g., RNA), such as by RT-PCR, e.g., qRT-PCR. Alternatively, or in addition, a patient can be evaluated for the presence of a KIF5B-RET protein fusion, such as by immunohistochemistry, Western blot, immunoprecipitation, or immunomagnetic bead assay.

Clinical trials suitable for repurposing as described above include trials that tested RET inhibitors, tyrosine kinase inhibitors, multikinase inhibitors, and drugs purported to act upstream or downstream of RET in a pathway involving RET. Other clinical trials suitable for repurposing as described above include trials that tested KIF5B inhibitors, kinesin inhibitors, inhibitors of cell trafficking and drugs purported to act upstream or downstream of KIF5B in a pathway involving KIF5B.

Methods for Detection of KIF5B-RET Fusion Nucleic Acids and Polypeptides

Methods for evaluating a KIF5B-RET gene, mutations and/or gene products are known to those of skill in the art. In one embodiment, the KIF5B-RET fusion is detected in a nucleic acid molecule by a method chosen from one or more of: nucleic acid hybridization assay, amplification-based assays (e.g., polymerase chain reaction (PCR)), PCR-RFLP assay, real-time PCR, sequencing, screening analysis (including metaphase cytogenetic analysis by standard karyotype methods, FISH (e.g., break away FISH), spectral karyotyping or MFISH, comparative genomic hybridization), in situ hybridization, SSP, HPLC or mass-spectrometric genotyping.

Additional exemplary methods include, traditional "direct probe" methods such as Southern blots or in situ hybridization (e.g., fluorescence in situ hybridization (FISH) and FISH plus SKY), and "comparative probe" methods such as comparative genomic hybridization (CGH), e.g., cDNA-based or oligonucleotide-based CGH, can be used. The methods can be used in a wide variety of formats including, but not limited to, substrate (e.g., membrane or glass) bound methods or array-based approaches.

In certain embodiments, the evaluation methods include the probes/primers described herein.

In one embodiment, probes/primers can be designed to detect a KIF5B/RET fusion. The KIF5B probes/primers can be from nucleotides 1-1725 of SEQ ID NO:1 (e.g., can hybridize to the nucleotides encoding exons 1-15 of the KIF5B protein). These probes/primers are suitable, e.g., for FISH or PCR amplification. The RET probes/primers can be from nucleotides 1726-2934 of SEQ ID NO:1 (e.g., can hybridize to the nucleotides encoding exons 12-20 of the RET protein). These probes/primers are suitable, e.g., for FISH or PCR amplification. For PCR, e.g., to amply the region including the KIF5B/RET fusion junction, forward primers can be designed to hybridize to KIF5B sequence from nucleotides 1-1725 of SEQ ID NO:1, and reverse primers can be designed to hybridize from nucleotides 1726-2934 of SEQ ID NO:1.

In another embodiment, probes/primers can be designed to detect a RET/KIF5B fusion. The RET probes/primers can be from nucleotides 1-2138 of SEQ ID NO:3 (i.e., can hybridize to the nucleotides encoding exons 1-11 of the RET protein). These probes/primers are suitable, e.g., for FISH or PCR amplification. The KIF5B probes/primers can be from nucleotides 2139-3360 of SEQ ID NO:3 (i.e., can hybridize to the nucleotides encoding exons 16-26 of the KIF5B protein). These probes/primers are suitable, e.g., for FISH or PCR amplification. For PCR, e.g., to amply the region including the RET/KIF5B fusion junction, forward primers can be designed to hybridize to Ret sequence from nucleotides 1-2138 of SEQ ID NO:3, and reverse primers can be designed to hybridize from nucleotides 2139-3360 of SEQ ID NO:3.

In one embodiment, FISH analysis is used to identify the chromosomal rearrangement resulting in the KIF5B-RET fusion as described above. For example, to perform FISH, at least a first probe tagged with a first detectable label can be designed to target KIF5B, such as in one or more of exons 1-15 of KIF5B (e.g., the exons containing the part of the protein that includes the kinesin motor domain and the oligomeric domain), and at least a second probe tagged with a second detectable label can be designed to target RET, such as in one or more of exons 12-25 of RET (e.g., the exons containing the part of the protein that includes the tyrosine kinase domain). The at least one first probe and the at least one second probe will be closer together in a subject who carries the KIF5B-RET fusion compared to a subject who does not carry the KIF5B-RET fusion.

In one approach, a variation of a FISH assay, e.g., "break-away FISH", is used to evaluate a patient. By this method, at least one probe targeting the RET intron 11/RET exon 12 junction and at least one probe targeting KIF5B, e.g., at one or more of exons 1-15, and or introns 1-14, are utilized. In normal cells, both probes with be observed (or a secondary color will be observed due to the close proximity of the KIF5B and RET genes), and only the KIF5B probe will be observed when the translocation occurs. Other variations of the FISH method known in the art are suitable for evaluating a patient.

Probes are used that contain DNA segments that are essentially complementary to DNA base sequences existing in different portions of chromosomes. Examples of probes useful according to the invention, and labeling and hybridization of probes to samples are described in two U.S. patents to Vysis, Inc. U.S. Pat. Nos. 5,491,224 and 6,277,569 to Bittner, et al.

Additional protocols for FISH detection are described below.

Chromosomal probes are typically about 50 to about $10^5$ nucleotides in length. Longer probes typically comprise smaller fragments of about 100 to about 500 nucleotides in length. Probes that hybridize with centromeric DNA and locus-specific DNA are available commercially, for example, from Vysis, Inc. (Downers Grove, Ill.), Molecular Probes, Inc. (Eugene, Oreg.) or from Cytocell (Oxfordshire, UK). Alternatively, probes can be made non-commercially from chromosomal or genomic DNA through standard techniques. For example, sources of DNA that can be used include genomic DNA, cloned DNA sequences, somatic cell hybrids that contain one, or a part of one, chromosome (e.g., human chromosome) along with the normal chromosome complement of the host, and chromosomes purified by flow cytometry or microdissection. The region of interest can be isolated through cloning, or by site-specific amplification via the polymerase chain reaction (PCR). See, for example, Nath and Johnson, Biotechnic Histochem., 1998, 73(1):6-22, Wheeless et al., Cytometry 1994, 17:319-326, and U.S. Pat. No. 5,491,224.

The probes to be used hybridize to a specific region of a chromosome to determine whether a cytogenetic abnormality is present in this region. One type of cytogenetic abnormality is a deletion. Although deletions can be of one or more entire chromosomes, deletions normally involve loss of part of one or more chromosomes. If the entire region of a chromosome that is contained in a probe is deleted from a cell, hybridization of that probe to the DNA from the cell will normally not occur and no signal will be present on that chromosome. If the region of a chromosome that is partially contained within a probe is deleted from a cell, hybridization of that probe to the DNA from the cell can still occur, but less of a signal can be present. For example, the loss of a signal is compared to probe hybridization to DNA from control cells that do not contain the genetic abnormalities which the probes are intended to detect. In some embodiments, at least 1, 5, 10, 20, 30, 40, 50, 60, 70, 80, 90, 100, 110, 120, 130, 140, 150, 160, 170, 180, 190, 200, or more cells are enumerated for presence of the cytogenetic abnormality.

Cytogenetic abnormalities to be detected can include, but are not limited to, non-reciprocal translocations, intra-chromosomal inversions, point mutations, deletions, gene copy number changes, gene expression level changes, and germ line mutations. In particular, one type of cytogenetic abnormality is a duplication. Duplications can be of entire chromosomes, or of regions smaller than an entire chromosome. If the region of a chromosome that is contained in a probe is duplicated in a cell, hybridization of that probe to the DNA from the cell will normally produce at least one additional signal as compared to the number of signals present in control cells with no abnormality of the chromosomal region contained in the probe.

Chromosomal probes are labeled so that the chromosomal region to which they hybridize can be detected. Probes typically are directly labeled with a fluorophore, an organic molecule that fluoresces after absorbing light of lower wavelength/higher energy. The fluorophore allows the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides. See, U.S. Pat. No. 5,491,224.

U.S. Pat. No. 5,491,224 describes probe labeling as a number of the cytosine residues having a fluorescent label covalently bonded thereto. The number of fluorescently labeled cytosine bases is sufficient to generate a detectable fluorescent signal while the individual so labeled DNA segments essentially retain their specific complementary binding (hybridizing) properties with respect to the chromosome or chromosome region to be detected. Such probes are made by taking the unlabeled DNA probe segment, transaminating with a linking group a number of deoxycytidine nucleotides in the segment, covalently bonding a fluorescent label to at least a portion of the transaminated deoxycytidine bases.

Probes can also be labeled by nick translation, random primer labeling or PCR labeling. Labeling is done using either fluorescent (direct)- or haptene (indirect)-labeled nucleotides. Representative, non-limiting examples of labels include: AMCA-6-dUTP, CascadeBlue-4-dUTP, Fluorescein-12-dUTP, Rhodamine-6-dUTP, TexasRed-6-dUTP, Cy3-6-dUTP, Cy5-dUTP, Biotin(BIO)-11-dUTP, Digoxygenin(DIG)-11-dUTP or Dinitrophenyl (DNP)-11-dUTP.

Probes also can be indirectly labeled with biotin or digoxygenin, or labeled with radioactive isotopes such as $^{32}p$ and $^3H$, although secondary detection molecules or further processing then is required to visualize the probes. For example, a probe labeled with biotin can be detected by avidin conjugated to a detectable marker. For example, avidin can be conjugated to an enzymatic marker such as alkaline phosphatase or horseradish peroxidase. Enzymatic markers can be detected in standard colorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

Probes can also be prepared such that a fluorescent or other label is not part of the DNA before or during the hybridization, and is added after hybridization to detect the probe hybridized to a chromosome. For example, probes can be used that have antigenic molecules incorporated into the DNA. After hybridization, these antigenic molecules are detected using specific antibodies reactive with the antigenic molecules. Such antibodies can themselves incorporate a fluorochrome, or can be detected using a second antibody with a bound fluorochrome.

However treated or modified, the probe DNA is commonly purified in order to remove unreacted, residual products (e.g., fluorochrome molecules not incorporated into the DNA) before use in hybridization.

Prior to hybridization, chromosomal probes are denatured according to methods well known in the art. Probes can be hybridized or annealed to the chromosomal DNA under hybridizing conditions. "Hybridizing conditions" are conditions that facilitate annealing between a probe and target chromosomal DNA. Since annealing of different probes will vary depending on probe length, base concentration and the like, annealing is facilitated by varying probe concentration, hybridization temperature, salt concentration and other factors well known in the art.

Hybridization conditions are facilitated by varying the concentrations, base compositions, complexities, and lengths of the probes, as well as salt concentrations, temperatures, and length of incubation. For example, in situ hybridizations are typically performed in hybridization buffer containing 1-2×SSC, 50-65% formamide and blocking DNA to suppress non-specific hybridization. In general, hybridization conditions, as described above, include temperatures of about 25° C. to about 55° C., and incubation lengths of about 0.5 hours to about 96 hours.

Non-specific binding of chromosomal probes to DNA outside of the target region can be removed by a series of washes. Temperature and concentration of salt in each wash are varied to control stringency of the washes. For example, for high stringency conditions, washes can be carried out at about 65° C. to about 80° C., using 0.2× to about 2×SSC, and about 0.1% to about 1% of a non-ionic detergent such as Nonidet P-40 (NP40). Stringency can be lowered by decreasing the temperature of the washes or by increasing the concentration of salt in the washes. In some applications it is necessary to block the hybridization capacity of repetitive sequences. Thus, in some embodiments, tRNA, human genomic DNA, or Cot-I DNA is used to block non-specific hybridization. After washing, the slide is allowed to drain and air dry, then mounting medium, a counterstain such as DAPI, and a coverslip are applied to the slide. Slides can be viewed immediately or stored at −20° C. before examination.

For fluorescent probes used in fluorescence in situ hybridization (FISH) techniques, fluorescence can be viewed with a fluorescence microscope equipped with an appropriate filter for each fluorophore, or by using dual or triple bandpass filter sets to observe multiple fluorophores. See, for example, U.S. Pat. No. 5,776,688. Alternatively, techniques such as flow cytometry can be used to examine the hybridization pattern of the chromosomal probes.

In CGH methods, a first collection of nucleic acids (e.g., from a sample, e.g., a possible tumor) is labeled with a first label, while a second collection of nucleic acids (e.g., a control, e.g., from a healthy cell/tissue) is labeled with a second label. The ratio of hybridization of the nucleic acids is determined by the ratio of the two (first and second) labels binding to each fiber in the array. Where there are chromosomal deletions or multiplications, differences in the ratio of the signals from the two labels will be detected and the ratio will provide a measure of the copy number. Array-based CGH can also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays.

Hybridization protocols suitable for use with the methods of the invention are described, e.g., in Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology*, Vol. 33: In situ Hybridization Protocols, Choo, ed., Humana Press, Totowa, N.J. (1994), etc. In one embodiment, the hybridization protocol of Pinkel, et al. (1998) *Nature Genetics* 20: 207-211, or of Kallioniemi (1992) *Proc. Natl Acad Sci USA* 89:5321-5325 (1992) is used. Array-based CGH is described in U.S. Pat. No. 6,455,258, the contents of each of which are incorporated herein by reference.

In still another embodiment, amplification-based assays can be used to measure presence/absence and copy number. In such amplification-based assays, the nucleic acid sequences act as a template in an amplification reaction (e.g., Polymerase Chain Reaction (PCR). In a quantitative amplification, the amount of amplification product will be proportional to the amount of template in the original sample. Comparison to appropriate controls, e.g., healthy tissue, provides a measure of the copy number.

Methods of "quantitative" amplification are well known to those of skill in the art. For example, quantitative PCR involves simultaneously co-amplifying a known quantity of a control sequence using the same primers. This provides an internal standard that can be used to calibrate the PCR reaction. Detailed protocols for quantitative PCR are provided in Innis, et al. (1990) *PCR Protocols, A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR can also be used in the methods of the invention. In fluorogenic quantitative PCR, quantitation is based on amount of fluorescence signals, e.g., TaqMan and sybr green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

Nucleic Acid Samples

A variety of tissue samples can be the source of the nucleic acid samples used in the present methods. Genomic or subgenomic DNA fragments can be isolated from a subject's sample (e.g., a tumor sample, a normal adjacent tissue (NAT), a blood sample or any normal control)). In certain embodiments, the tissue sample is preserved as a frozen sample or as formaldehyde- or paraformaldehyde-fixed paraffin-embedded (FFPE) tissue preparation. For example, the sample can be embedded in a matrix, e.g., an FFPE block or a frozen sample. The isolating step can include flow-sorting of individual chromosomes; and/or micro-dissecting a subject's sample (e.g., a tumor sample, a NAT, a blood sample).

Protocols for DNA isolation from a tissue sample are known in the art. Additional methods to isolate nucleic acids (e.g., DNA) from formaldehyde- or paraformaldehyde-fixed, paraffin-embedded (FFPE) tissues are disclosed, e.g., in Cronin M. et al., (2004) *Am J Pathol.* 164(1):35-42; Masuda N. et al., (1999) *Nucleic Acids Res.* 27(22):4436-4443; Specht K. et al., (2001) *Am J Pathol.* 158(2):419-429, Ambion RecoverAll™ Total Nucleic Acid Isolation Protocol (Ambion, Cat. No. AM1975, September 2008), and QIAamp® DNA FFPE Tissue Handbook (Qiagen, Cat. No. 37625, October 2007). RecoverAll™ Total Nucleic Acid Isolation Kit uses xylene at elevated temperatures to solubilize paraffin-embedded samples and a glass-fiber filter to capture nucleic acids. QIAamp® DNA FFPE Tissue Kit uses QIAamp® DNA Micro technology for purification of genomic and mitochondrial DNA.

The isolated nucleic acid samples (e.g., genomic DNA samples) can be fragmented or sheared by practicing routine techniques. For example, genomic DNA can be fragmented by physical shearing methods, enzymatic cleavage methods, chemical cleavage methods, and other methods well known to those skilled in the art. The nucleic acid library can contain all or substantially all of the complexity of the genome. The term "substantially all" in this context refers to the possibility that there can in practice be some unwanted loss of genome complexity during the initial steps of the procedure. The methods described herein also are useful in cases where the nucleic acid library is a portion of the genome, i.e., where the complexity of the genome is reduced by design. In some embodiments, any selected portion of the genome can be used with the methods described herein. In certain embodiments, the entire exome or a subset thereof is isolated.

Methods can further include isolating a nucleic acid sample to provide a library (e.g., a nucleic acid library). In certain embodiments, the nucleic acid sample includes whole genomic, subgenomic fragments, or both. The isolated nucleic acid samples can be used to prepare nucleic acid libraries. Thus, in one embodiment, the methods featured in the invention further include isolating a nucleic acid sample to provide a library (e.g., a nucleic acid library as described herein). Protocols for isolating and preparing libraries from whole genomic or subgenomic fragments are known in the art (e.g., Illumina's genomic DNA sample preparation kit). In certain embodiments, the genomic or subgenomic DNA fragment is isolated from a subject's sample (e.g., a tumor sample, a normal adjacent tissue (NAT), a blood sample or any normal control)). In one embodiment, the sample (e.g., the tumor or NAT sample) is a preserved. For example, the sample is embedded in a matrix, e.g., an FFPE block or a frozen sample. In certain embodiments, the isolating step includes flow-sorting of individual chromosomes; and/or microdissecting a subject's sample (e.g., a tumor sample, a NAT, a blood sample). In certain embodiments, the nucleic acid sample used to generate the nucleic acid library is less than 5, less than 1 microgram, less than 500 ng, less than 200 ng, less than 100 ng, less than 50 ng or less than 20 ng (e.g., 10 ng or less).

In still other embodiments, the nucleic acid sample used to generate the library includes RNA or cDNA derived from RNA. In some embodiments, the RNA includes total cellular RNA. In other embodiments, certain abundant RNA sequences (e.g., ribosomal RNAs) have been depleted. In some embodiments, the poly(A)-tailed mRNA fraction in the total RNA preparation has been enriched. In some embodiments, the cDNA is produced by random-primed cDNA synthesis methods. In other embodiments, the cDNA synthesis is initiated at the poly(A) tail of mature mRNAs by priming by oligo(dT)-containing oligonucleotides. Methods for depletion, poly(A) enrichment, and cDNA synthesis are well known to those skilled in the art.

The method can further include amplifying the nucleic acid sample (e.g., DNA or RNA sample) by specific or non-specific nucleic acid amplification methods that are well known to those skilled in the art. In some embodiments, certain embodiments, the nucleic acid sample is amplified, e.g., by whole-genome amplification methods such as random-primed strand-displacement amplification.

In other embodiments, the nucleic acid sample is fragmented or sheared by physical or enzymatic methods and ligated to synthetic adapters, size-selected (e.g., by preparative gel electrophoresis) and amplified (e.g., by PCR). In other embodiments, the fragmented and adapter-ligated group of nucleic acids is used without explicit size selection or amplification prior to hybrid selection.

In other embodiments, the isolated DNA (e.g., the genomic DNA) is fragmented or sheared. In some embodiments, the library includes less than 50% of genomic DNA, such as a subfraction of genomic DNA that is a reduced representation or a defined portion of a genome, e.g., that has been subfractionated by other means. In other embodiments, the library includes all or substantially all genomic DNA.

In some embodiments, the library includes less than 50% of genomic DNA, such as a subfraction of genomic DNA that is a reduced representation or a defined portion of a genome, e.g., that has been subfractionated by other means. In other embodiments, the library includes all or substantially all genomic DNA. Protocols for isolating and preparing libraries from whole genomic or subgenomic fragments are known in the art (e.g., Illumina's genomic DNA sample preparation kit). Alternative DNA shearing methods can be more automatable and/or more efficient (e.g., with degraded FFPE samples). Alternatives to DNA shearing methods can also be used to avoid a ligation step during library preparation.

The methods described herein can be performed using a small amount of nucleic acids, e.g., when the amount of source DNA is limiting (e.g., even after whole-genome amplification). In one embodiment, the nucleic acid comprises less than about 5 µg, 4 µg, 3 µg, 2 µg, 1 µg, 0.8 µg, 0.7 µg, 0.6 µg, 0.5 µg, or 400 ng, 300 ng, 200 ng, 100 ng, 50 ng, or 20 ng or less of nucleic acid sample. For example, to prepare 500 ng of hybridization-ready nucleic acids, one typically begins with 3 µg of genomic DNA. One can start with less, however, if one amplifies the genomic DNA (e.g., using PCR) before the step of solution hybridization. Thus it is possible, but not essential, to amplify the genomic DNA before solution hybridization.

In some embodiments, a library is generated using DNA (e.g., genomic DNA) from a sample tissue, and a corresponding library is generated with RNA (or cDNA) isolated from the same sample tissue.

Design of Baits

A bait can be a nucleic acid molecule, e.g., a DNA or RNA molecule, which can hybridize to (e.g., be complementary to), and thereby allow capture of a target nucleic acid. In one embodiment, a bait is an RNA molecule. In other embodiments, a bait includes a binding entity, e.g., an affinity tag, that allows capture and separation, e.g., by binding to a binding entity, of a hybrid formed by a bait and a nucleic acid hybridized to the bait. In one embodiment, a bait is suitable for solution phase hybridization.

Baits can be produced and used by methods and hybridization conditions as described in US 2010/0029498 and Gnirke, A. et al. (2009) *Nat Biotechnol.* 27(2):182-189, and U.S. Ser. No. 61/428,568, filed Dec. 30, 2010, incorporated herein by reference. For example, biotinylated RNA baits can be produced by obtaining a pool of synthetic long oligonucleotides, originally synthesized on a microarray, and amplifying the oligonucleotides to produce the bait sequences. In some embodiments, the baits are produced by adding an RNA polymerase promoter sequence at one end of the bait sequences, and synthesizing RNA sequences using RNA polymerase. In one embodiment, libraries of synthetic oligodeoxynucleotides can be obtained from commercial suppliers, such as Agilent Technologies, Inc., and amplified using known nucleic acid amplification methods.

Each bait sequence can include a target-specific (e.g., a member-specific) bait sequence and universal tails on each end. As used herein, the term "bait sequence" can refer to the target-specific bait sequence or the entire oligonucleotide including the target-specific "bait sequence" and other nucleotides of the oligonucleotide. In one embodiment, a target-specific bait hybridizes to a nucleic acid sequence comprising a nucleic acid sequence in intron 15 of KIF5B, in intron 11 of RET, or a fusion junction joining exon 15 of KIF5B and exon 12 of RET.

In one embodiment, the bait is an oligonucleotide about 200 nucleotides in length, of which 170 nucleotides are target-specific "bait sequence". The other 30 nucleotides (e.g., 15 nucleotides on each end) are universal arbitrary tails used for PCR amplification. The tails can be any sequence selected by the user. For example, the pool of synthetic oligonucleotides can include oligonucleotides of the sequence of 5'-ATCGCACCAGCGTGTN$_{170}$CACTGCGGCTCCTCA-3' with N$_{170}$ indicating the target-specific bait sequences.

The bait sequences described herein can be used for selection of exons and short target sequences. In one embodiment, the bait is between about 100 nucleotides and 300 nucleotides in length. In another embodiment, the bait is between about 130 nucleotides and 230 nucleotides in length. In yet another embodiment, the bait is between about 150 nucleotides and 200 nucleotides in length. The target-specific sequences in the baits, e.g., for selection of exons and short target sequences, are between about 40 nucleotides and 1000 nucleotides in length. In one embodiment, the target-specific sequence is between about 70 nucleotides and 300 nucleotides in length. In another embodiment, the target-specific sequence is between about 100 nucleotides and 200 nucleotides in length. In yet another embodiment, the target-specific sequence is between about 120 nucleotides and 170 nucleotides in length.

Sequencing

The invention also includes methods of sequencing nucleic acids. In one embodiment, any of a variety of sequencing reactions known in the art can be used to directly sequence at least a portion of a KIF5B-RET fusion. In one embodiment, the KIF5B-RET fusion sequence is compared to a corresponding reference (control) sequence.

In one embodiment, the sequence of the KIF5B-RET fusion nucleic acid molecule is determined by a method that includes one or more of: hybridizing an oligonucleotide, e.g., an allele specific oligonucleotide for one alteration described herein to said nucleic acid; hybridizing a primer, or a primer set (e.g., a primer pair), that amplifies a region comprising the mutation or a fusion junction of the allele; amplifying, e.g., specifically amplifying, a region comprising the mutation or a fusion junction of the allele; attaching an adapter oligonucleotide to one end of a nucleic acid that comprises the mutation or a fusion junction of the allele; generating an optical, e.g., a colorimetric signal, specific to the presence of the one of the mutation or fusion junction; hybridizing a nucleic acid comprising the mutation or fusion junction to a second nucleic acid, e.g., a second nucleic acid attached to a substrate; generating a signal, e.g., an electrical or fluorescent signal, specific to the presence of the mutation or fusion junction; and incorporating a nucleotide into an oligonucleotide that is hybridized to a nucleic acid that contains the mutation or fusion junction.

In another embodiment, the sequence is determined by a method that comprises one or more of: determining the nucleotide sequence from an individual nucleic acid molecule, e.g., where a signal corresponding to the sequence is derived from a single molecule as opposed, e.g., from a sum of signals from a plurality of clonally expanded molecules; determining the nucleotide sequence of clonally expanded proxies for individual nucleic acid molecules; massively parallel short-read sequencing; template-based sequencing; pyrosequencing; real-time sequencing comprising imaging the continuous incorporation of dye-labeling nucleotides during DNA synthesis; nanopore sequencing; sequencing by hybridization; nano-transistor array based sequencing; polony sequencing; scanning tunneling microscopy (STM) based sequencing; or nanowire-molecule sensor based sequencing.

Any method of sequencing known in the art can be used. Exemplary sequencing reactions include those based on techniques developed by Maxam and Gilbert (*Proc. Natl Acad Sci USA* (1977) 74:560) or Sanger (Sanger et al. (1977) *Proc. Nat. Acad. Sci* 74:5463). Any of a variety of automated sequencing procedures can be utilized when performing the assays (*Biotechniques* (1995) 19:448), including sequencing by mass spectrometry (see, for example, U.S. Pat. No. 5,547,835 and international patent application Publication Number WO 94/16101, entitled DNA Sequencing by Mass Spectrometry by H. Köster; U.S. Pat. No. 5,547,835 and international patent application Publication Number WO 94/21822 entitled DNA Sequencing by Mass Spectrometry Via Exonuclease Degradation by H. Köster), and U.S. Pat. No. 5,605,798 and International Patent Application No. PCT/US96/03651 entitled DNA Diagnostics Based on Mass Spectrometry by H. Köster; Cohen et al. (1996) *Adv Chromatogr* 36:127-162; and Griffin et al. (1993) *Appl Biochem Biotechnol* 38:147-159).

Sequencing of nucleic acid molecules can also be carried out using next-generation sequencing (NGS). Next-generation sequencing includes any sequencing method that determines the nucleotide sequence of either individual nucleic acid molecules or clonally expanded proxies for individual nucleic acid molecules in a highly parallel fashion (e.g., greater than $10^5$ molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. (2010) *Nature Biotechnology Reviews* 11:31-46, incorporated herein by reference.

In one embodiment, the next-generation sequencing allows for the determination of the nucleotide sequence of an individual nucleic acid molecule (e.g., Helicos BioSciences' HeliScope Gene Sequencing system, and Pacific Biosciences' PacBio RS system). In other embodiments, the sequencing method determines the nucleotide sequence of clonally expanded proxies for individual nucleic acid molecules (e.g., the Solexa sequencer, Illumina Inc., San Diego, Calif; 454 Life Sciences (Branford, Conn.), and Ion Torrent). e.g., massively parallel short-read sequencing (e.g., the Solexa sequencer, Illumina Inc., San Diego, Calif.), which generates more bases of sequence per sequencing unit than other sequencing methods that generate fewer but longer reads. Other methods or machines for next-generation sequencing include, but are not limited to, the sequencers provided by 454 Life Sciences (Branford, Conn.), Applied Biosystems (Foster City, Calif.; SOLiD sequencer), and Helicos BioSciences Corporation (Cambridge, Mass.).

Platforms for next-generation sequencing include, but are not limited to, Roche/454's Genome Sequencer (GS) FLX System, Illumina/Solexa's Genome Analyzer (GA), Life/APG's Support Oligonucleotide Ligation Detection (SOLiD) system, Polonator's G.007 system, Helicos BioSciences' HeliScope Gene Sequencing system, and Pacific Biosciences' PacBio RS system.

NGS technologies can include one or more of steps, e.g., template preparation, sequencing and imaging, and data analysis.

Template Preparation

Methods for template preparation can include steps such as randomly breaking nucleic acids (e.g., genomic DNA or cDNA) into smaller sizes and generating sequencing templates (e.g., fragment templates or mate-pair templates). The spatially separated templates can be attached or immobilized to a solid surface or support, allowing massive amounts of sequencing reactions to be performed simultaneously. Types of templates that can be used for NGS reactions include, e.g., clonally amplified templates originating from single DNA molecules, and single DNA molecule templates.

Methods for preparing clonally amplified templates include, e.g., emulsion PCR (emPCR) and solid-phase amplification.

EmPCR can be used to prepare templates for NGS. Typically, a library of nucleic acid fragments is generated, and adapters containing universal priming sites are ligated to the ends of the fragment. The fragments are then denatured into single strands and captured by beads. Each bead captures a single nucleic acid molecule. After amplification and enrichment of emPCR beads, a large amount of templates can be attached or immobilized in a polyacrylamide gel on a standard microscope slide (e.g., Polonator), chemically crosslinked to an amino-coated glass surface (e.g., Life/APG; Polonator), or deposited into individual PicoTiterPlate (PTP) wells (e.g., Roche/454), in which the NGS reaction can be performed.

Solid-phase amplification can also be used to produce templates for NGS. Typically, forward and reverse primers are covalently attached to a solid support. The surface density of the amplified fragments is defined by the ratio of the primers to the templates on the support. Solid-phase amplification can produce hundreds of millions spatially separated template clusters (e.g., Illumina/Solexa). The ends of the template clusters can be hybridized to universal sequencing primers for NGS reactions.

Other methods for preparing clonally amplified templates also include, e.g., Multiple Displacement Amplification (MDA) (Lasken R. S. *Curr Opin Microbiol.* 2007; 10(5): 510-6). MDA is a non-PCR based DNA amplification technique. The reaction involves annealing random hexamer primers to the template and DNA synthesis by high fidelity enzyme, typically Φ29 at a constant temperature. MDA can generate large sized products with lower error frequency.

Template amplification methods such as PCR can be coupled with NGS platforms to target or enrich specific regions of the genome (e.g., exons). Exemplary template enrichment methods include, e.g., microdroplet PCR technology (Tewhey R. et al., *Nature Biotech.* 2009, 27:1025-1031), custom-designed oligonucleotide microarrays (e.g., Roche/NimbleGen oligonucleotide microarrays), and solution-based hybridization methods (e.g., molecular inversion probes (MIPs) (Porreca G. J. et al., *Nature Methods,* 2007, 4:931-936; Krishnakumar S. et al., *Proc. Natl. Acad. Sci. USA,* 2008, 105:9296-9310; Turner E. H. et al., *Nature Methods,* 2009, 6:315-316), and biotinylated RNA capture sequences (Gnirke A. et al., *Nat. Biotechnol.* 2009; 27(2): 182-9)

Single-molecule templates are another type of templates that can be used for NGS reaction. Spatially separated single molecule templates can be immobilized on solid supports by various methods. In one approach, individual primer molecules are covalently attached to the solid support. Adapters are added to the templates and templates are then hybridized to the immobilized primers. In another approach, single-molecule templates are covalently attached to the solid support by priming and extending single-stranded, single-molecule templates from immobilized primers. Universal primers are then hybridized to the templates. In yet another approach, single polymerase molecules are attached to the solid support, to which primed templates are bound.

Sequencing and Imaging

Exemplary sequencing and imaging methods for NGS include, but are not limited to, cyclic reversible termination (CRT), sequencing by ligation (SBL), single-molecule addition (pyrosequencing), and real-time sequencing.

CRT uses reversible terminators in a cyclic method that minimally includes the steps of nucleotide incorporation, fluorescence imaging, and cleavage. Typically, a DNA polymerase incorporates a single fluorescently modified nucleotide corresponding to the complementary nucleotide of the template base to the primer. DNA synthesis is terminated after the addition of a single nucleotide and the unincorporated nucleotides are washed away. Imaging is performed to determine the identity of the incorporated labeled nucleotide. Then in the cleavage step, the terminating/inhibiting group and the fluorescent dye are removed. Exemplary NGS platforms using the CRT method include, but are not limited to, Illumina/Solexa Genome Analyzer (GA), which uses the clonally amplified template method coupled with the four-color CRT method detected by total internal reflection fluorescence (TIRF); and Helicos BioSciences/HeliScope, which uses the single-molecule template method coupled with the one-color CRT method detected by TIRF.

SBL uses DNA ligase and either one-base-encoded probes or two-base-encoded probes for sequencing. Typically, a fluorescently labeled probe is hybridized to its complementary sequence adjacent to the primed template. DNA ligase is used to ligate the dye-labeled probe to the primer. Fluorescence imaging is performed to determine the identity of the ligated probe after non-ligated probes are washed away. The fluorescent dye can be removed by using cleavable probes to regenerate a 5'-$PO_4$ group for subsequent ligation cycles. Alternatively, a new primer can be hybridized to the template after the old primer is removed. Exemplary SBL platforms include, but are not limited to, Life/APG/SOLiD (support oligonucleotide ligation detection), which uses two-base-encoded probes.

Pyrosequencing method is based on detecting the activity of DNA polymerase with another chemiluminescent enzyme. Typically, the method allows sequencing of a single strand of DNA by synthesizing the complementary strand along it, one base pair at a time, and detecting which base was actually added at each step. The template DNA is immobile, and solutions of A, C, G, and T nucleotides are sequentially added and removed from the reaction. Light is produced only when the nucleotide solution complements the first unpaired base of the template. The sequence of solutions which produce chemiluminescent signals allows the determination of the sequence of the template. Exemplary pyrosequencing platforms include, but are not limited to, Roche/454, which uses DNA templates prepared by emPCR with 1-2 million beads deposited into PTP wells.

Real-time sequencing involves imaging the continuous incorporation of dye-labeled nucleotides during DNA synthesis. Exemplary real-time sequencing platforms to include, but are not limited to, Pacific Biosciences platform, which uses DNA polymerase molecules attached to the surface of individual zero-mode waveguide (ZMW) detectors to obtain sequence information when phospholinked nucleotides are being incorporated into the growing primer strand; Life/VisiGen platform, which uses an engineered DNA polymerase with an attached fluorescent dye to generate an enhanced signal after nucleotide incorporation by fluorescence resonance energy transfer (FRET); and LI- COR Biosciences platform, which uses dye-quencher nucleotides in the sequencing reaction.

Other sequencing methods for NGS include, but are not limited to, nanopore sequencing, sequencing by hybridization, nano-transistor array based sequencing, polony sequencing, scanning tunneling microscopy (STM) based sequencing, and nanowire-molecule sensor based sequencing.

Nanopore sequencing involves electrophoresis of nucleic acid molecules in solution through a nano-scale pore which provides a highly confined space within which single-nucleic acid polymers can be analyzed. Exemplary methods of nanopore sequencing are described, e.g., in Branton D. et al., *Nat Biotechnol.* 2008; 26(10):1146-53.

Sequencing by hybridization is a non-enzymatic method that uses a DNA microarray. Typically, a single pool of DNA is fluorescently labeled and hybridized to an array containing known sequences. Hybridization signals from a given spot on the array can identify the DNA sequence. The binding of one strand of DNA to its complementary strand in the DNA double-helix is sensitive to even single-base mismatches when the hybrid region is short or is specialized mismatch detection proteins are present. Exemplary methods of sequencing by hybridization are described, e.g., in Hanna G. J. et al., *J. Clin. Microbiol.* 2000; 38 (7): 2715-21; and Edwards J. R. et al., *Mut. Res.* 2005; 573 (1-2): 3-12.

Polony sequencing is based on polony amplification and sequencing-by-synthesis via multiple single-base-extensions (FISSEQ). Polony amplification is a method to amplify DNA in situ on a polyacrylamide film. Exemplary polony sequencing methods are described, e.g., in US Patent Application Publication No. 2007/0087362.

Nano-transistor array based devices, such as Carbon NanoTube Field Effect Transistor (CNTFET), can also be used for NGS. For example, DNA molecules are stretched and driven over nanotubes by micro-fabricated electrodes. DNA molecules sequentially come into contact with the carbon nanotube surface, and the difference in current flow from each base is produced due to charge transfer between the DNA molecule and the nanotubes. DNA is sequenced by recording these differences. Exemplary Nano-transistor array based sequencing methods are described, e.g., in U.S. Patent Application Publication No. 2006/0246497.

Scanning tunneling microscopy (STM) can also be used for NGS. STM uses a piezo-electric-controlled probe that performs a raster scan of a specimen to form images of its surface. STM can be used to image the physical properties of single DNA molecules, e.g., generating coherent electron tunneling imaging and spectroscopy by integrating scanning tunneling microscope with an actuator-driven flexible gap. Exemplary sequencing methods using STM are described, e.g., in U.S. Patent Application Publication No. 2007/0194225.

A molecular-analysis device which is comprised of a nanowire-molecule sensor can also be used for NGS. Such device can detect the interactions of the nitrogenous material disposed on the nanowires and nucleic acid molecules such as DNA. A molecule guide is configured for guiding a molecule near the molecule sensor, allowing an interaction and subsequent detection. Exemplary sequencing methods using nanowire-molecule sensor are described, e.g., in U.S. Patent Application Publication No. 2006/0275779.

Double ended sequencing methods can be used for NGS. Double ended sequencing uses blocked and unblocked primers to sequence both the sense and antisense strands of DNA. Typically, these methods include the steps of annealing an unblocked primer to a first strand of nucleic acid; annealing a second blocked primer to a second strand of nucleic acid; elongating the nucleic acid along the first strand with a polymerase; terminating the first sequencing primer; deblocking the second primer; and elongating the nucleic acid along the second strand. Exemplary double ended sequencing methods are described, e.g., in U.S. Pat. No. 7,244,567.

Data Analysis

After NGS reads have been generated, they can be aligned to a known reference sequence or assembled de novo.

For example, identifying genetic variations such as single-nucleotide polymorphism and structural variants in a sample (e.g., a tumor sample) can be accomplished by aligning NGS reads to a reference sequence (e.g., a wild-type sequence). Methods of sequence alignment for NGS are described e.g., in Trapnell C. and Salzberg S. L. *Nature Biotech.*, 2009, 27:455-457.

Examples of de novo assemblies are described, e.g., in Warren R. et al., *Bioinformatics,* 2007, 23:500-501; Butler J. et al., *Genome Res.,* 2008, 18:810-820; and Zerbino D. R. and Birney E., *Genome Res.,* 2008, 18:821-829.

Sequence alignment or assembly can be performed using read data from one or more NGS platforms, e.g., mixing Roche/454 and Illumina/Solexa read data.

Algorithms and methods for data analysis are described in U.S. Ser. No. 61/428,568, filed Dec. 30, 2010, incorporated herein by reference.

KIF5B-RET Fusion Expression Level

In certain embodiments, KIF5B-RET fusion expression level can also be assayed. KIF5B-RET fusion expression can be assessed by any of a wide variety of methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In certain embodiments, activity of a particular gene is characterized by a measure of gene transcript (e.g., mRNA), by a measure of the quantity of translated protein, or by a measure of gene product activity. KIF5B-RET fusion expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

Methods of detecting and/or quantifying the KIF5B-RET gene transcript (mRNA or cDNA made therefrom) using nucleic acid hybridization techniques are known to those of skill in the art (see Sambrook et al. supra). For example, one method for evaluating the presence, absence, or quantity of cDNA involves a Southern transfer as described above. Briefly, the mRNA is isolated (e.g., using an acid guanidinium-phenol-chloroform extraction method, Sambrook et al. supra.) and reverse transcribed to produce cDNA. The cDNA is then optionally digested and run on a gel in buffer and transferred to membranes. Hybridization is then carried out using the nucleic acid probes specific for the KIF5B-RET fusion cDNA, e.g., using the probes and primers described herein.

In other embodiments, KIF5B-RET expression is assessed by preparing genomic DNA or mRNA/cDNA (i.e., a transcribed polynucleotide) from cells in a subject sample, and by hybridizing the genomic DNA or mRNA/cDNA with a reference polynucleotide which is a complement of a polynucleotide comprising the KIF5B-RET fusion, and fragments thereof. cDNA can, optionally, be amplified using any of a variety of polymerase chain reaction methods prior to hybridization with the reference polynucleotide. Expression of KIF5B-RET fusion can likewise be detected using quantitative PCR (QPCR) to assess the level of KIF5B-RET expression.

Detection of KIF5B-RET Fusion Polypeptide

The activity or level of a KIF5B-RET fusion polypeptide can also be detected and/or quantified by detecting or quantifying the expressed polypeptide. The KIF5B-RET fusion polypeptide can be detected and quantified by any of a number of means known to those of skill in the art. These can include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, immunohistochemistry (IHC) and the like. A skilled artisan can adapt known protein/antibody detection methods.

Another agent for detecting a KIF5B-RET fusion polypeptide is an antibody molecule capable of binding to a polypeptide corresponding to a marker of the invention, e.g., an antibody with a detectable label. Techniques for generating antibodies are described herein. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

In another embodiment, the antibody is labeled, e.g., a radio-labeled, chromophore-labeled, fluorophore-labeled, or enzyme-labeled antibody. In another embodiment, an antibody derivative (e.g., an antibody conjugated with a substrate or with the protein or ligand of a protein-ligand pair {e.g., biotin-streptavidin}), or an antibody fragment (e.g., a single-chain antibody, an isolated antibody hypervariable domain, etc.) which binds specifically with a KIF5B-RET fusion protein, is used.

KIF5B-RET fusion polypeptides from cells can be isolated using techniques that are known to those of skill in the art. The protein isolation methods employed can, for example, be such as those described in Harlow and Lane (Harlow and Lane, 1988, *Antibodies: A Laboratory Manual*, Cold Spring Harbor Laboratory Press, Cold Spring Harbor, New York).

Means of detecting proteins using electrophoretic techniques are well known to those of skill in the art (see generally, R. Scopes (1982) *Protein Purification*, Springer-Verlag, N.Y.; Deutscher, (1990) *Methods in Enzymology* Vol. 182: *Guide to Protein Purification*, Academic Press, Inc., N.Y.).

In another embodiment, Western blot (immunoblot) analysis is used to detect and quantify the presence of a polypeptide in the sample.

In another embodiment, the polypeptide is detected using an immunoassay. As used herein, an immunoassay is an assay that utilizes an antibody to specifically bind to the analyte. The immunoassay is thus characterized by detection of specific binding of a polypeptide to an anti-antibody as opposed to the use of other physical or chemical properties to isolate, target, and quantify the analyte.

The KIF5B-RET fusion polypeptide is detected and/or quantified using any of a number of immunological binding assays (see, e.g., U.S. Pat. Nos. 4,366,241; 4,376,110; 4,517,288; and 4,837,168). For a review of the general immunoassays, see also Asai (1993) *Methods in Cell Biology* Volume 37: *Antibodies in Cell Biology*, Academic Press, Inc. New York; Stites & Terr (1991) *Basic and Clinical Immunology* 7th Edition.

Kits

In one aspect, the invention features, a kit, e.g., containing an oligonucleotide having a mutation described herein, e.g., a KIT5B-RET fusion. Optionally, the kit can also contain an oligonucleotide that is the wildtype counterpart of the mutant oligonucleotide.

A kit featured in the invention can include a carrier, e.g., a means being compartmentalized to receive in close confinement one or more container means. In one embodiment the container contains an oligonucleotide, e.g., a primer or probe as described above. The components of the kit are useful, for example, to diagnose identify a mutation in a tumor sample in a patient, and to accordingly identify an appropriate therapeutic agent to treat the cancer. The probe or primer of the kit can be used in any sequencing or nucleotide detection assay known in the art, e.g., a sequencing assay, e.g., an NGS method, RT-PCR, or in situ hybridization.

A kit featured in the invention can include, e.g., assay positive and negative controls, nucleotides, enzymes (e.g., RNA or DNA polymerase or ligase), solvents or buffers, a stabilizer, a preservative, a secondary antibody, e.g., an anti-HRP antibody (IgG) and a detection reagent.

An oligonucleotide can be provided in any form, e.g., liquid, dried, semi-dried, or lyophilized, or in a form for storage in a frozen condition.

Typically, an oligonucleotide, and other components in a kit are provided in a form that is sterile. When an oligonucleotide, e.g., an oligonucleotide that contains a RET mutation, e.g., a KIF5B-RET fusion, described herein, or an oligonucleotide complementary to a mutation RET mutation described herein, is provided in a liquid solution, the liquid solution generally is an aqueous solution, e.g., a sterile aqueous solution. When the oligonucleotide is provided as a dried form, reconstitution generally is accomplished by the addition of a suitable solvent. The solvent, e.g., sterile buffer, can optionally be provided in the kit.

The kit can include one or more containers for the composition containing an oligonucleotide in a concentration suitable for use in the assay or with instructions for dilution for use in the assay. In some embodiments, the kit contains separate containers, dividers or compartments for the oligonucleotide and assay components, and the informational material. For example, the oligonucleotides can be contained in a bottle or vial, and the informational material can be contained in a plastic sleeve or packet. In other embodiments, the separate elements of the kit are contained within a single, undivided container. For example, an oligonucleotide composition is contained in a bottle or vial that has attached thereto the informational material in the form of a label. In some embodiments, the kit includes a plurality (e.g., a pack) of individual containers, each containing one or more unit forms (e.g., for use with one assay) of an oligonucleotide. For example, the kit includes a plurality of ampoules, foil packets, or blister packs, each containing a single unit of oligonucleotide for use in a sequencing or detecting a mutation in a tumor sample. The containers of the kits can be air tight and/or waterproof. The container can be labeled for use.

For antibody-based kits, the kit can include: (1) a first antibody (e.g., attached to a solid support) which binds to a KIF5B-RET fusion polypeptide; and, optionally, (2) a second, different antibody which binds to either the polypeptide or the first antibody and is conjugated to a detectable agent.

In one embodiment, the kit can include informational material for performing and interpreting the sequencing or diagnostic. In another embodiment, the kit can provide guidance as to where to report the results of the assay, e.g., to a treatment center or healthcare provider. The kit can include forms for reporting the results of a sequencing or diagnostic assay described herein, and address and contact information regarding where to send such forms or other related information; or a URL (Uniform Resource Locator) address for reporting the results in an online database or an online application (e.g., an app). In another embodiment, the informational material can include guidance regarding whether a patient should receive treatment with a particular chemotherapeutic drug, depending on the results of the assay.

The informational material of the kits is not limited in its form. In many cases, the informational material, e.g., instructions, is provided in printed matter, e.g., a printed text, drawings, and/or photographs, e.g., a label or printed sheet. However, the informational material can also be provided in other formats, such as computer readable material, video recording, or audio recording. In another embodiment, the informational material of the kit is contact information, e.g., a physical address, email address, website, or telephone number, where a user of the kit can obtain substantive information about the sequencing or diagnostic assay and/or its use in the methods described herein. The informational material can also be provided in any combination of formats.

In some embodiments, a biological sample is provided to an assay provider, e.g., a service provider (such as a third party facility) or a healthcare provider, who evaluates the sample in an assay and provides a read out. For example, in one embodiment, an assay provider receives a biological sample from a subject, such as a blood or tissue sample, e.g., a biopsy sample, and evaluates the sample using an assay described herein, e.g., a sequencing assay or in situ hybridization assay, and determines that the sample contains a nucleic acid containing a mutation described in the Example. The assay provider, e.g., a service provider or healthcare provider, can then conclude that the subject is, or is not, a candidate for a particular drug or a particular cancer treatment regimen.

The assay provider can provide the results of the evaluation, and optionally, conclusions regarding one or more of diagnosis, prognosis, or appropriate therapy options to, for example, a healthcare provider, or patient, or an insurance company, in any suitable format, such as by mail or electronically, or through an online database. The information collected and provided by the assay provider can be stored in a database.

The invention is further illustrated by the following example, which should not be construed as further limiting.

EXAMPLES

Example 1: Massively Parallel Sequencing Assays to Identify Novel Alterations

The following exemplifies the use of massively parallel sequencing assays to identify novel alterations, such as KIF5B-RET fusions. Based on the results shown herein, additional alterations, e.g., RET translocations, can be screened using, e.g., either qRT-PCR analysis of cDNA prepared from a pre-selected tumor sample.

INTRODUCTION

Figure 5:
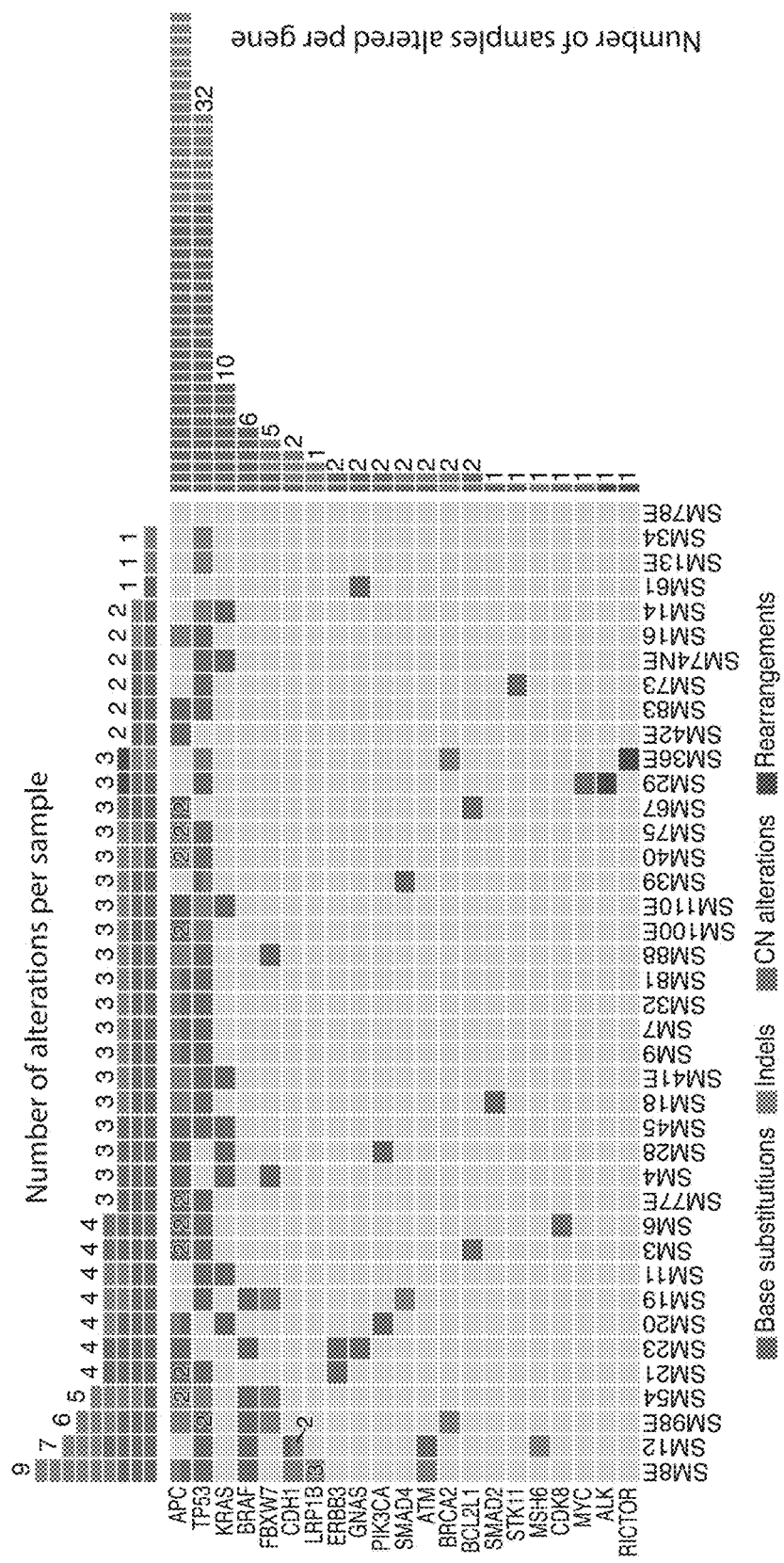
FIG. 5 is a summary of the DNA alterations identified in colorectal cancer cells.

A pan-cancer diagnostic assay based on massively parallel sequencing technology was developed to interrogate 2574 coding exons representing 145 cancer relevant genes (associated with cancer-related pathways, targeted-therapy or prognosis), plus 37 introns from 14 genes frequently rearranged in cancer, using minimal DNA from formalin fixed paraffin embedded (FFPE) tumor specimens. This assay can identify all classes of DNA alterations (e.g., base substitutions, insertions and deletions, copy number alterations and rearrangements) in a single diagnostic test. In a cohort of 40 colorectal cancer (CRC) and 24 non-small cell lung cancer (NSCLC) specimens, 175 alterations were identified in 33 cancer genes. 38 samples (59%) harbored at least one alteration that could be linked to a clinical treatment option or clinical trial of novel targeted therapies, including a novel KIF5B-RET gene fusion in NSCLC (the KIF5B-RET gene fusions is described in Example 2 herein).
Results An evaluation of assays using genomic DNA derived from 40 CRC and 24 NSCLC FFPE tissue samples was performed (Supplementary Table 1). In total, 2574 coding exons representing 145 cancer genes, plus 37 introns from 15 frequently rearranged cancer genes (Supplementary Table 2) were selected using solution phase hybrid capture and sequenced on the Illumina HiSeq2000 platform (Illumina, Inc., San Diego, Calif.) to an average coverage of 253X.175 alterations in 33 cancer genes were identified of which 116 were single base substitutions (75 non synonymous, 41 nonsense), 46 were small insertions or deletions (indels) (44 frameshift, 2 in-frame), 10 were copy number alterations (9 amplifications, 1 homozygous deletion) and 3 were rearrangements (FIG. 5, Supplementary Table 2).

The percentage distribution of DNA alterations in 40 CRCs is roughly as follows: about 58% are base substitutions, 28% are insertions and deletions, 12% are copy number alterations, about 1% are gene fusions.

The percentage distribution of DNA alterations in 24 NSCLCs is roughly as follows: about 72% are base substitutions, 14% are insertions and deletions, 12% are copy number alterations, about 2% are gene fusions.
Mutations Identified in CRC Cases Among 40 CRCs, 125 alterations were identified in 21 genes. 39 tumors carried at least one mutation (range 1-9) and 25 tumors (62.5%) contained at least two different classes of DNA alteration (FIG. 5). TP53 and APC were the most frequently altered genes (32/40 (80%) and 27/40 (67.5%), respectively), with both mutated at higher frequencies than reported in COSMIC (on the worldwide web at sanger.ac.uk/genetics/CGP/cosmic/). 41/42 (98%) of the APC mutations in the cohort were truncating (21 nonsense, 17 frameshift indel), an observation unique to CRC tumors which indicates the specificity of the assay. 15 samples had bi-allelic inactivation and 12 a single truncating APC mutation and LOH.

In addition, 11 known cancer genes were mutated, amplified or rearranged in multiple CRC cases: KRAS (10), BRAF (6), FBXW7 (5), ATM (2), BCL2L1 (2), BRCA2 (2), CDH1 (2), ERBB3 (2), GNAS (2), PIK3CA (2) and SMAD4 (2), ALK, CDK8, LRP1B, MYC, MSH6, RICTOR, SMAD2 and STK11 were each altered in a single case (FIG. 5, Supplementary Table 1). Notably, 21 CRCs (52.5%) harbored at least one alteration that could be linked to a clinical treatment option or clinical trial of novel targeted therapies. Examples include mutations in KRAS and BRAF (resistance to cetuximab (Lievre et al., Cancer Res 66:3992-3995, 2006; Di Nicolantonio et al., J Clin Oncol. 26:5705-5712, 2008) or panitumumab (Di Nicolantonio et al., supra; Lievre et al., Bull Cancer 95:133-140, 2008), FBXW7 (resistance to anti-tubulins (Wertz, et al., Nature 471:110-114, 2011)), BRCA2 (clinical trials of PARP inhibitors (Turner et al., Curr Opin Pharmacol 5:388-393, 2005), GNAS (clinical trials of MEK or ERK inhibitors), PIK3CA (clinical trials of PI3 kinase/mTOR inhibitors), and CDK8 (clinical trials of CDK inhibitors ref) (Supplementary Table 3).

Mutations Identified in NSCLC Cases

Among 24 NSCLCs, 50 mutations were identified in 21 genes. 20 of 24 tumors harbored at least one mutation (range 1-7) (Supplementary FIGS. 4 and 5, Supplementary Table 2). Twelve genes were altered in multiple tumors: KRAS (10), TP53 (7), STK11 (4), LRP1B (3), JAK2 (3), EGFR (2), BRAF (2), CDKN2A (2), CTNNB1 (2), MDM2 (2), PIK3CA (2) and ATM (2). APC, CCNE1, CDK4, MLH1, MSH6, NF1, RB1, RET and TSC1 were each mutated in a single case. In addition, 3 patients had a truncating mutation in the putative tumor suppressor gene LRP1B (Liu et al., Genomics 69:271-274, 2000), further supporting the role of inactivation of this gene in oncogenesis. In 72% (36/50) of NSCLCs at least one alteration was associated with a current clinical treatment or targeted therapy trial, including mutations in KRAS (resistance to EGFR kinase inhibitors (Pao et al., PLoS Med 2:e17, 2005); clinical trials of PI3K and MEK inhibitors) and BRAF (clinical trials of BRAF inhibitors including vemurafenibref and GSK 2118436 ref), EGFR (sensitivity to gefitinib or erlotinib ref), MDM2 (clinical trials of nutlins (Vassilev et al., Science 303:844-848, 2004), CDKN2A, CCNE1 and CDK4 (clinical trials of CDK4 inhibitors (Finn et al., Breast Cancer Res. 11:R77, 2009; Toogood et al., J Med Chem 48:2388-2406, 2005; Konecny et al., Clin Cancer Res 17:1591-1602, 2011), and PIK3CA (clinical trials of PI3 kinase/mTOR inhibitors ref) (Supplementary Table 4). Although the test detects the EMIR-ALK inversions in cell lines, EML4-ALK was not identified in this patient cohort (Soda et al., Nature 448:561-566, 2007).

Surprisingly, three patients were found to have a c.1849G>Tp.V617F mutation in JAK, which is commonly observed myelodysplastic syndromes (MDS) but has not been identified in solid tumors (James et al., Nature 434: 1144-1148, 2005) (see online at sanger.ac.uk/genetics/CGP/cosmic/), although one patient had a history of polycythemia vera with a bone marrow positive for the JAK2 mutation. Sequencing a larger series of NSCLC specimens can be conducted to further characterize JAK2 mutations in NSCLC, and further studies can be conducted to assess whether these predict clinical sensitivity to JAK2 inhibitors.

Example 2A: Novel KIF5B-RET Fusions

Figure 6A:
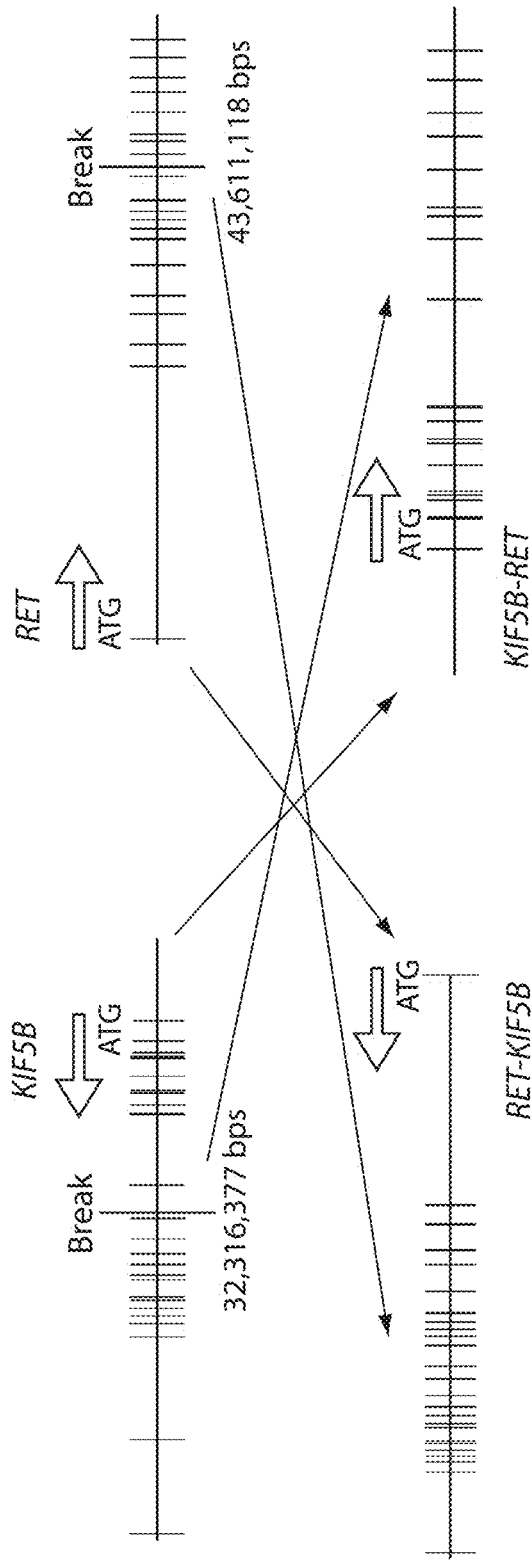
FIG. 6A provides a schematic representation of the 11,294,741 bp inversion in NSCLC that generates an in-frame KIF5B-RET gene fusion (not to scale). The inverted region of chromosome 10 starts at 32,316,377 bps (within KIF5B intron 15) and ends at 43,611,118 bps (within RET intron 11).

A novel inversion event was identified in a lung adenocarcinoma using NGS (Next Generation) sequencing. The adenocarcinoma was from a 44-year old, male Caucasian never-smoker. A genomic sequence suggestive of a novel chromosome 10 rearrangement, specifically an 11 MB pericentric inversion with breakpoints in intron 15 of KIF5B and intron 11 of RET, was observed. The breakpoints were determined to be at Chr10:32,316,376-32,316,416 within intron 15 of KIF5B and Chr 10:43,611,042-43,611,118 within intron 11 of RET (see FIG. 1). More specifically, an 11,294,741 bp pericentric inversion generates the RET gene fusion joining exons 1-15 of KIF5B to exon 12-20 of RET. FIG. 6A provides a schematic representation of the 11,294,741 bp inversion in NSCLC that generates an in-frame KIF5B-RET gene fusion (not to scale). The inverted region of chromosome 10 starts at 32,316,377 bps (within KIF5B intron 15) and ends at 43,611,118 bps (within RET intron 11). FIG. 6D is a summary of the exons present or absent in the KIF5B-RET fusion.

The inversion results in an in-frame fusion of the 5'end of KIF5B and the 3'end of RET, which fusion is expressed to generate a fusion protein that includes a tyrosine kinase domain in the RET protein. More specifically, the protein fusion results in an in-frame fusion of exon 15 of KIF5B with exon 12 of RET. See FIGS. 2B and 3A-3D. In FIGS. 3A-3D, SEQ ID NO:1 is the cDNA sequence of the KIF5B-RET fusion (i.e., 5'-KIF5B-3'-RET fusion) and SEQ ID NO:2 is the amino acid sequence of the KIF5B-RET fusion protein. The underlined sequence in FIGS. 3A-3D represents KIF5B cDNA sequence (nucleotides 471-2195 of RefSeq No. NM_004521.2 (GenBank Record Aug. 14, 2011)) and KIF5B protein sequence (amino acids 1-575 of RefSeq No. NP_004512 (GenBank Record Aug. 14, 2011)). The sequence not underlined in FIGS. 3A-3D represents RET cDNA sequence (nucleotides 2327-3535 of RefSeq No. NM_020975 (GenBank Record Aug. 14, 2011) and RET protein sequence (amino acids 713-1114 of RefSeq No. NP_066124.1 (GenBank Record Aug. 14, 2011)). The RET protein sequence in the KIF5B-RET fusion maintains the intact tyrosine kinase domain of RET, and this domain is indicated by a gray box in FIG. 3C. The KIF5B protein sequence in the fusion maintains the intact kinesin motor domain, and this domain is indicated by a double-underlining in FIGS. 3A-3B. KIF5B exons 1 to 15 also contain the coiled-coil domain that mediates homodimerization. At least because the KIF5B-RET fusion is an in-frame fusion that maintains the intact tyrosine kinase domain of RET, and the kinesin motor domain and coiled-coil domain of KIF5B, this fusion protein is likely to contribute to the oncogenic phenotype of the lung tumor sample.

Figure 7A:
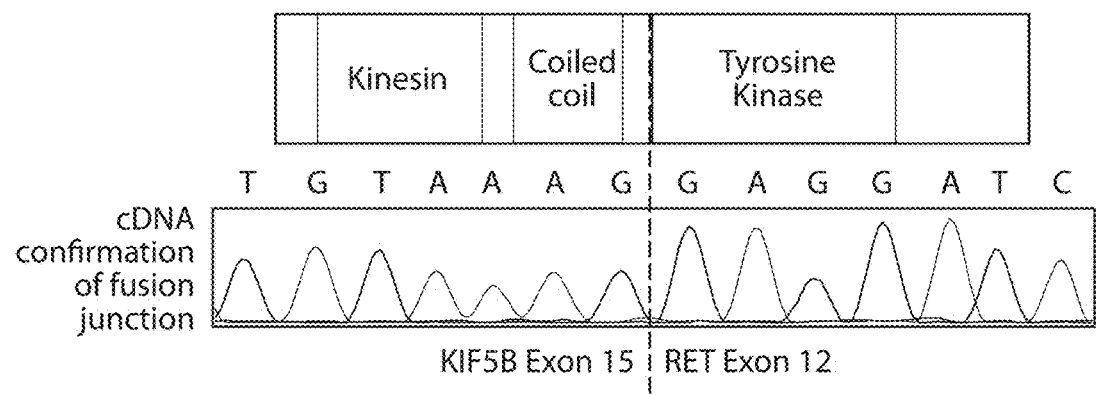
FIG. 7A provides another schematic representation of the KIF5B-RET fusion. This variant was identified in 8 CRC cases, where KIF5B exon 15 is fused in-frame to RET exon 12. The predicted full length fusion protein is 977 amino acids in length, with amino acids 1-575 derived from KIF5B and amino acids 576-977 derived from RET (shown above). Capillary sequence confirmation of the exon junction boundaries derived from cDNA is shown below.

FIG. 7A provides another schematic representation of the KIF5B-RET fusion. This variant was identified in 10 CRC cases, where KIF5B exon 15 is fused in-frame to RET exon 12. The predicted full length fusion protein is 977 amino acids in length, with amino acids 1-575 derived from KIF5B and amino acids 576-977 derived from RET (shown above). Capillary sequence confirmation of the exon junction boundaries derived from cDNA is shown below. FIG. 7B is another representation of the predicted KIF5B-RET variant amino acid sequence. Amino acids derived from KIF5B (normal text). Amino acids derived from RET (italics, underlined).

KIF5B exons 1-15 comprise a kinesin motor domain and a coiled-coil domain that directly mediates homodimerization. KIF5B exon 15 is a known fusion point in NSCLC patients with KIF5B-ALK fusions (Wong et al., Cancer, 2011; Takeuchi et al., Clin Cancer Res 15:3143-3149, 2009).

Figure 6B:
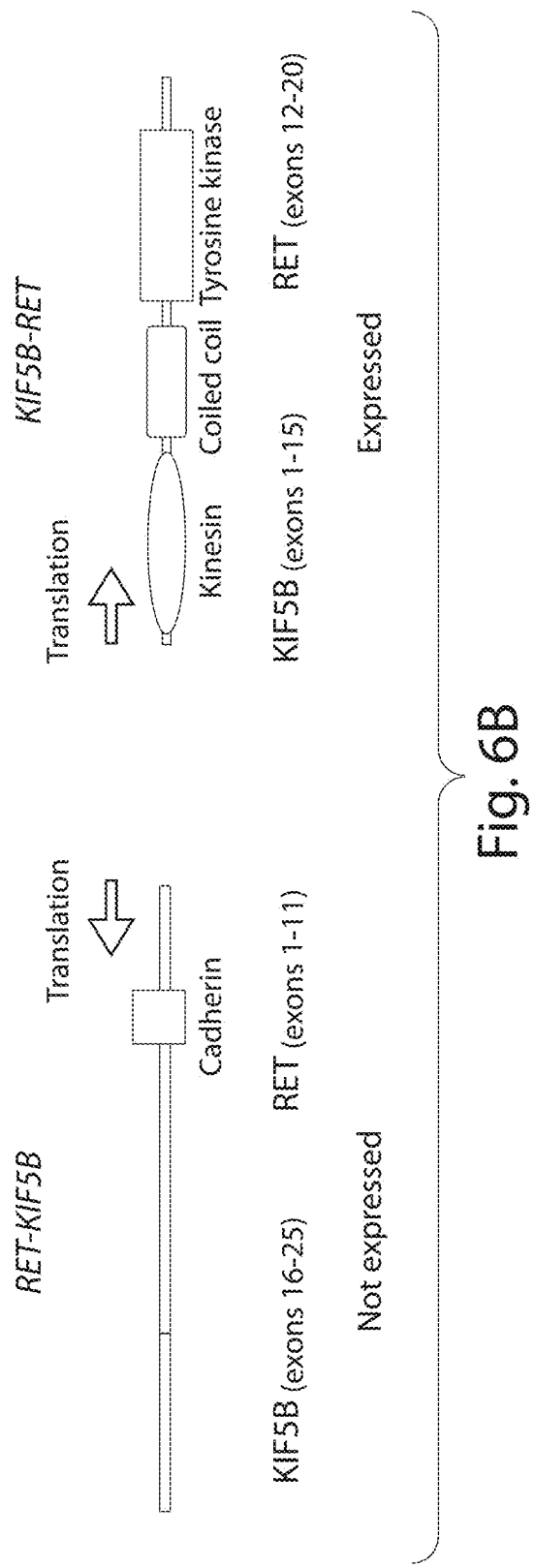
FIG. 6B is a schematic of the protein domain structure of the RET-KIF5B and KIF5B-RET gene fusions. The cadherin domain of RET is included in the predicted RET-KIF5B protein. The kinesin and coiled coil domains of KIF5B and the tyrosine kinase domain of RET are included in the KIF5B-RET fusion protein. RT-PCR of primer designed to RET exon 11 and KIF5B exon 16 yielded no product. RT-PCR of primer designed to KIF5B exon 15 and RET exon 12 yielded a strong product (data not shown).

FIG. 6B is a schematic of the protein domain structure of the RET-KIF5B and KIF5B-RET gene fusions. The cadherin domain of RET is included in the predicted RET-KIF5B protein. The kinesin and coiled coil domains of KIF5B and the tyrosine kinase domain of RET are included in the KIF5B-RET fusion protein. RT-PCR of primer designed to RET exon 11 and KIF5B exon 16 yielded no product. RT-PCR of primer designed to KIF5B exon 15 and RET exon 12 yielded a strong product. Using cDNA sequencing, a 7.3 fold RET expression increase beginning at exon 12 relative to exons 1 to 11, suggesting the KIF5B-RET fusion transcript results in RET kinase domain overexpression. In addition, cDNA sequencing revealed that 490 unique read pairs spanned the fusion junction.

Figure 6C:
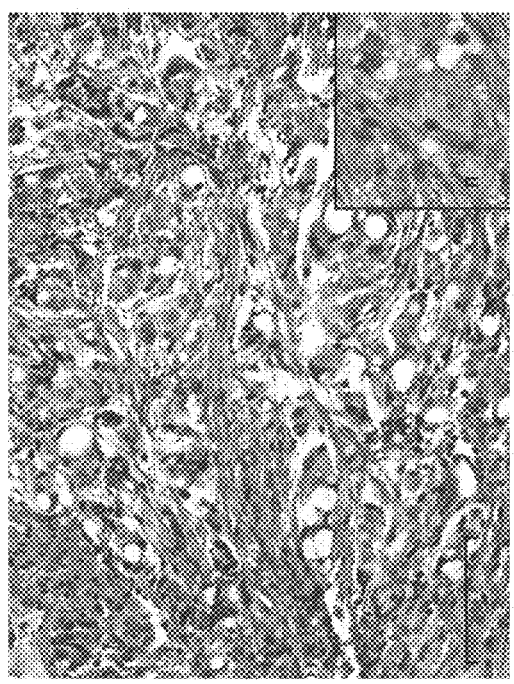
FIG. 6C is a photograph depicting the distribution of RET expression in the case of NSCLC with confirmed RET fusion on DNA sequencing by NGS. Note focal moderate cytoplasmic immunoreactivity for RET protein expression (avidin-biotin perxodase×200). High magnification detail of cytoplasmic immunostaining for RET is shown in the insert at the lower right.
Figure 6D:
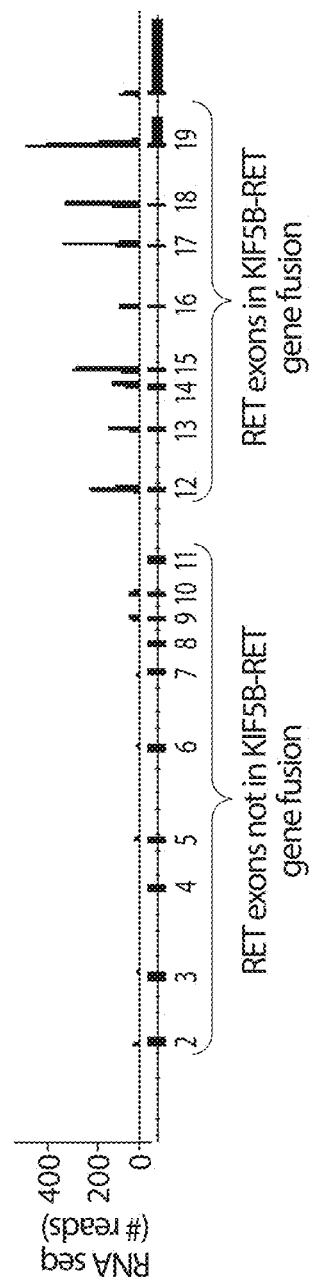
FIG. 6D is a summary of the exons present or absent in the KIF5B-RET fusion.

IHC demonstrated focal moderate cytoplasmic immunoreactivity for RET protein expression (FIG. 6C). FIG. 6C is a photograph depicting the distribution of RET expression in the case of NSCLC with confirmed RET fusion on DNA sequencing by NGS. Note focal moderate cytoplasmic immunoreactivity for RET protein expression (avidin-biotin perxodase×200). High magnification detail of cytoplasmic immunostaining for RET is shown in the insert at the lower right.

Previous RET fusion proteins have been identified in cancers other than lung cancer. For example, the RET oncogene has been shown to be activated through somatic rearrangements in papillary thyroid carcinomas. RET exons 12-20 comprise the RET tyrosine kinase domain which commonly forms the 3' portion of the PTC/RET fusions observed in ~35% of papillary thyroid carcinomas. KIF5B-ALK fusions have been previously identified in ALK-positive lung cancer. To our knowledge, this is the first demonstration of a RET fusion cDNA in a lung cancer, and also the first demonstration of a KIF5B-RET fusion.

Thyroid cancer and cell lines harboring oncogenic PTC/RET translocations, which overexpress the RET kinase domain, are sensitive to RET inhibitor sorafenib suggesting that this KIF5B-RET gene fusion may identify a new druggable subset of NSCLC tumors (Henderson et al., *Clin Cancer Res* 14:4908-4914, 2008; Carlomagno et al., *J Natl Cancer Inst* 98:326-334, 2006). Other RET activating mutations have been shown to be sensitive to treatment with the multikinase inhibitor sorafenib (e.g., Plaza-Menacho et al., *Jour. Biol. Chem.* 282:29230-29240, 2007). It is, therefore, expected that cancers carrying a KIF5B-RET fusion as described herein is likely to be susceptible to treatment with multikinase inhibitors, such as sorafenib and sunitinib.

Together these results suggest druggable gene fusions can occur broadly in cancer at low frequency and are more effectively identified with a sequencing-based diagnostic such as the one described herein.

RET Fusion Recurrence

To determine whether the RET fusion is recurrently expressed in NSCLC, a series of 117 NSCLCs (92 Caucasian, 5 African-American, 20 ethnicity unknown) were screened for RET by IHC; 22/117 cases showed moderate to intense staining. RT-PCR and cDNA sequencing of RNA from 15 IHC-positive tumors identified one additional KIF5B-RET fusion in a male Caucasian smoking patient (Table 2).

Example 2B: Additional KIF5B-RET Fusions

The chromosome 10 inversion that creates the KIF5B-RET fusion, can also create a reciprocal RET-KIF5B fusion (i.e., 5'-RET-3'-KIF5B fusion). See FIGS. 2A and 4A-4D. The predicted RET-KIF5B protein fusion results in a fusion of exon 11 of RET with exon 16 of KIF5B. See FIGS. 2A and 4A-4D. In FIGS. 4A-4D, SEQ ID NO:3 is the cDNA sequence of the RET-KIF5B fusion and SEQ ID NO:4 is the amino acid sequence of the predicted RET-KIF5B fusion protein. The underlined sequence in FIGS. 4A-4D represents KIF5B cDNA sequence (nucleotides 2196-3362 of RefSeq No. NM_004521.2 (GenBank Record Aug. 14, 2011)) and KIF5B protein sequence (amino acids 576-963 of RefSeq No. NP_004512 (GenBank Record Aug. 14, 2011)). The sequence not underlined in FIGS. 4A-4D represents RET cDNA sequence (nucleotides 190-2326 of RefSeq No. NM_020975 (GenBank Record Aug. 14, 2011) and RET protein sequence (amino acids 1-712 of RefSeq No. NP_066124.1 (GenBank Record Aug. 14, 2011)). The predicted RET protein sequence in the RET-KIF5B fusion does not include the tyrosine kinase domain. RT-PCR studies designed to RET exon 11 and KIF5B exon 16 yielded no product. Thus, this orientation of the fusion is not expressed.

Further screening of tumor samples has identified additional KIF5B-RET gene fusions that contain a RET catalytic domain.

Figure 8:
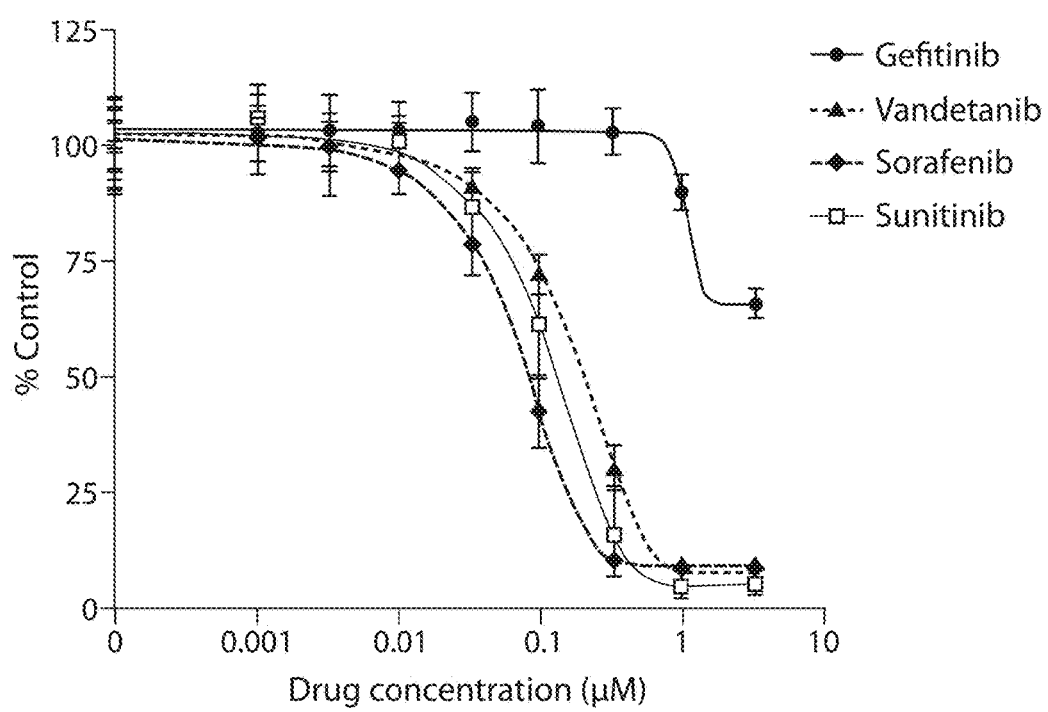
FIG. 8 is a graph showing the effects of different drugs on Ba/F3 cells transfected with KIF5B-RET fusion constructs.
Figure 9:
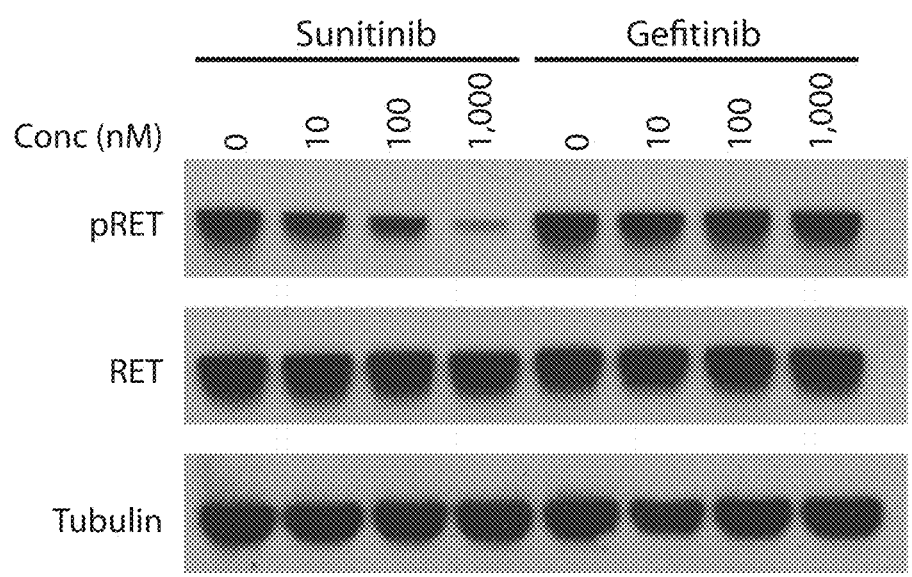
FIG. 9 is a Western blot showing the effects of sunitinib and gefitinib on RET phosphorylation in Ba/R3 cells expressing KIF5B-RET.

Thyroid cancers and cell lines harboring PTC-RET translocations are sensitive to sorafenib which inhibits RET, suggesting the KIF5B-RET gene fusion in NSCLC may be druggable. KIF5B-RET expression in Ba/F3 cells led to oncogenic transformation as determined by IL-3 independent growth. These cells were sensitive to sunitinib, sorafenib and vandetinib, multi-targeted kinase inhibitors that inhibit RET, but not gefitinib, an EGFR kinase inhibitor (FIG. 8). Sunitinib, but not gefitinib, inhibited RET phosphorylation in KIF5B-RET Ba/F3 cells (FIG. 9). These findings suggest RET kinase inhibitors should be tested in prospective clinical trials for therapeutic benefit in NSCLC patients bearing KIF5B-RET rearrangements.

DISCUSSION

In the current study, a comprehensive genomic profiling assay that robustly identifies base substitutions, insertions, deletions, copy number alterations and genomic rearrangements from FFPE tumor tissue is described. Results show that genomic alterations with direct clinical therapeutic relevance are detected in a large fraction of CRCs and NSCLCs demonstrating the value of systematically testing for such alterations in cancer patients. Due to the wide range of targeted therapies already approved or under clinical development, performing simultaneous, comprehensive querying for a wide breadth of genomic alterations will speed identification of appropriate patient subsets for these therapeutic approaches.

The method additionally identified two previously unknown genomic rearrangements, each of which could potentially lead to a therapeutic intervention. The first is an ALK rearrangement similar to those previously detected in anaplastic lymphoma (Morris et al., *Science* 263:1281-1284, 1994), NSCLC (Soda et al., *Nature* 448:561-566, 2007, supra) and inflammatory myofibroblastic tumor (Lawrence et al., *Am J Pathol* 157: 377-384, 2000) that are associated with clinical sensitivity to the ALK kinase inhibitor crizotinib (Kwak et al., *N Engl J Med* 363:1693-1703, 2010; Butrynski et al., *N Engl J Med* 363:1727-1733, 2010). The current findings suggest that other cancers, including CRC, can contain additional previously undetected ALK rearrangements that could be drug sensitive.

More importantly, applying comprehensive genomic profiling to tumor specimens identified recurrent novel KIF5B-RET inversions in NSCLC patients. This fusion gene contains the entire kinase domain of RET and results in increased RET kinase domain expression. Oncogenic PTC/RET translocations detected in thyroid cancer and cell lines are sensitive in vitro and in vivo to RET inhibitors (Henderson et al., *Clin Cancer Res* 14:4908-4914, 2008; Carlomagno et al., *J Natl Cancer Inst* 98:326-334, 2006; Kim et al., *J Clin Endocrinol Metab* 91:4070-4076, 2006; Dawson et al., *Anticancer Drugs* 19:547-552, 2008). It is possible that sunitinib or other RET tyrosine kinase inhibitors, including vandetinib or sorafenib (Henderson et al., supra), can be clinically effective in KIF5B-RET NSCLC. Identification of even a small subpopulation of NSCLC patients responsive to a molecular targeted therapy can have large clinical impact as highlighted by the recent FDA approval of crizotinib for ALK-rearranged NSCLC. It is clear is that harnessing the power of massively parallel sequencing to generate comprehensive genomic profiles for patient tumors will be increasingly clinically informative and eventually critical to effective therapeutic management in the oncology clinic.

Example 3: Methods

The following exemplifies certain embodiments of the methods and experimental conditions used to identify the KIF5B-RET fusion according to Examples 1-2. Additional RET translocation screening can be done using, e.g., either qRT-PCR analysis of cDNA prepared from a pre-selected tumor sample.

Massively parallel DNA sequencing was done on hybridization captured, adaptor ligation-based libraries using DNA isolated from archived fixed paraffin-embedded tissue. A combination of analysis tools were used to analyze the data and assign DNA alteration calls. Additional RET translocation screening was done using either qRT-PCR analysis of cDNA prepared from frozen tumors or RET IHC assessment of archived FFPE specimens. Massively parallel cDNA sequencing was performed to confirm expression of both novel translocations using RNA isolated from FFPE tissue. Matched normal reference genomic DNA from blood was sequenced for the index KIF5B-RET NSCLC patient to confirm the somatic origin of the rearrangement.

Genomic DNA Sequencing

Sequencing of 2574 exons of 145 cancer genes was performed using DNA from archived formalin fixed paraffin embedded (FFPE) tumor specimens; 24 from NSCLC patients and 40 from colorectal (CRC) pateints. Sequencing libraries of the 606,675 bp content were constructed by the adapter ligation method using genomic DNA followed by solution phase hybridization selection with optimized RNA hybridization capture probes (Agilent SureSelect custom kit). Sequencing on the HiSeq2000 instrument (Illumina) was performed using 36×36 paired reads to an average coverage of 229× with 84% exons at ≥100× (Supplementary Tables 2A and 2B). Data processing and mutation assignments for base substitutions, indels, copy number alterations and genomic rearrangements was performed using a combination of tools optimized for mutation calling from tumor tissue. To maximize mutation detection sensitivity in heterogeneous cancer biopsies, the test was validated to detect base substitutions at ≥10% mutant allele frequency with ≥99% sensitivity and indels at ≥20% mutant allele frequency with ≥95% sensitivity, with a false discovery rate of <1%.

cDNA Sequencing cDNA was generated from total RNA extracted from a single 5-10 um FFPE tissue section using the Roche High Pure kit and reverse transcribed to cDNA with random hexamer primers by the SuperScript® III First-Strand Synthesis System (Invitrogen). Double stranded cDNA was made with the NEBNext® mRNA Second Strand Synthesis Module (New England Biolabs) and used as input to library construction, hybrid capture and sequencing as for FFPE DNA samples. Analysis of expression levels was done with a combination of analysis tools.

RET Protein Immunohistochemistry

NSCLC were immunostained after microwave-based epitope retrieval by automated methods (Ventana Medical Systems, Tucson, Ariz.) for RET expression using the mouse monoclonal RET Oncoprotein clone 3F8 (Vector Laboratories, Burlingame, Calif.). Slides were scored semi-quantitatively for tumor cell staining intensity and distribution using the H Score system.

TABLE 1

Distribution of 125 CRC mutations across 21 mutated cancer genes

| Gene | Mutated Samples | Total Mutations | Non Synonymous | Nonsense | INDEL frameshift | Amplification | Rearrangement |
|---|---|---|---|---|---|---|---|
| TP53 | 32 | 34 | 23 | 3 | 8 | — | — |
| APC | 27 | 42 | 1 | 24 | 17 | — | — |
| KRAS | 10 | 10 | 10 | — | — | — | — |
| BRAF | 6 | 6 | 6 | — | — | — | — |
| FBXW7 | 5 | 5 | — | 2 | 3 | — | — |
| ATM | 2 | 2 | — | 1 | 1 | — | — |
| BCL2L1 | 2 | 2 | — | — | — | 2 | — |
| BRCA2 | 2 | 2 | — | — | 2 | — | — |
| CDH1 | 2 | 4 | — | 1 | 3 | — | — |
| ERBB3 | 2 | 2 | 2 | — | — | — | — |
| GNAS | 2 | 2 | 2 | — | — | — | — |
| PIK3CA | 2 | 2 | 2 | — | — | — | — |
| SMAD4 | 2 | 2 | 1 | — | 1 | — | — |
| ALK | 1 | 1 | — | — | — | — | 1 |
| CDK8 | 1 | 1 | — | — | — | 1 | — |
| LRP1B | 1 | 3 | — | — | 3 | — | — |
| MYC | 1 | 1 | — | — | — | 1 | — |
| MSH6 | 1 | 1 | — | — | 1 | — | — |
| RICTOR | 1 | 1 | — | — | — | — | 1 |
| SMAD2 | 1 | 1 | — | 1 | — | — | — |
| STK11 | 1 | 1 | — | 1 | — | — | — |

TABLE 2

Summary of non-small cell lung cancer patients analyzed by RET immunohistochemistry

| Characteristic | No. of Patients (n = 117) |
|---|---|
| Gender | |
| Male | 62 |
| Female | 55 |
| Histology | |
| Adenocarcinoma | 83 |
| Squamous cell Carcinoma | 26 |
| Carcinoid | 8 |
| Other | |
| Smoking | |
| Never | 5 |
| Limited former | 53 |
| Current | 34 |
| Unknown | 25 |
| Stage | |
| I | 77 |
| II | 16 |
| III | 13 |
| IV | 8 |
| N/A | 3 |

TABLE 2-continued

Summary of non-small cell lung cancer patients analyzed by RET immunohistochemistry

| Characteristic | No. of Patients (n = 117) |
|---|---|
| RET IHC | |
| 0 | 78 |
| 1+/2+ | 17 |
| 3+/4+ | 22 |

No of KIF5B-RET fusions: 1
Frequency in all patients: 1/117: 0.85%
Frequency Adenocarcinoma: 1/89: 1.1%

SUPPLEMENTARY TABLE 1b genes sequenced across selected introns (n = 14)

| Gene | RefSeq | Introns sequenced |
|---|---|---|
| ALK | NM_004304 | 19 |
| BCR | NM_004327 | 8, 13, 14 |
| BRAF | NM_004333 | 7, 8, 9, 10 |
| EGFR | NM_005228 | 7 |
| ETV1 | NM_004956 | 3, 4 |
| ETV4 | NM_001986 | 8 |
| ETV5 | NM_004454 | 6, 7 |
| ETV6 | NM_001987 | 5, 6 |
| EWSR1 | NM_005243 | 8, 9, 10, 11, 12, 13 |
| MLL | NM_005933 | 6, 7, 8, 9 |

SUPPLEMENTARY TABLE 1a 145 genes sequenced across entire coding sequence

| Gene | RefSeq | Gene | RefSeq | Gene | RefSeq | Gene | RefSeq | Gene | RefSeq |
|---|---|---|---|---|---|---|---|---|---|
| ABL1 | NM_007313 | NF1 | NM_000267 | CDK6 | NM_001259 | MDM2 | NM_002392 | SMARCB1 | NM_003073 |
| AKT1 | NM_005163 | NOTCH1 | NM_017617 | CDK8 | NM_001260 | MDM4 | NM_002393 | SOX10 | NM_006941 |
| AKT2 | NM_001626 | NPM1 | NM_002520 | CHEK1 | NM_001274 | MEN1 | NM_000244 | SOX2 | NM_003106 |
| AKT3 | NM_181690 | NRAS | NM_002524 | CHEK2 | NM_007194 | MITF | NM_198159 | SRC | NM_005417 |
| ALK | NM_004304 | NTRK3 | NM_002530 | CRKL | NM_005207 | MLH1 | NM_000249 | TET2 | NM_017628 |
| APC | NM_000038 | PDGFRA | NM_006206 | EPHA6 | NM_173655 | MPL | NM_005373 | TGFBR2 | NM_005242 |
| AR | NM_000044 | PIK3CA | NM_006218 | EPHB4 | NM_004444 | MRE11A | NM_005590 | TOP1 | NM_003286 |
| BRAF | NM_004333 | PIK3R1 | NM_181523 | EPHB6 | NM_004445 | MSH2 | NM_000251 | TSC1 | NM_000368 |
| CCND1 | NM_053056 | PTCH1 | NM_000264 | ERBB3 | NM_001982 | MSH6 | NM_000179 | TSC2 | NM_000548 |
| CDK4 | NM_000075 | PTEN | NM_000314 | ERBB4 | NM_005235 | MTOR | NM_004958 | VHL | NM_000551 |
| CDKN2A | NM_000077 | RB1 | NM_000321 | FBXW7 | NM_018315 | MYCL1 | NM_005376 | WT1 | NM_000378 |
| CEBPA | NM_004364 | RET | NM_020630 | FGFR4 | NM_002011 | MYCN | NM_005378 | ARFRP1 | NM_003224 |
| CTNNB1 | NM_001904 | SMO | NM_005631 | FLT1 | NM_002019 | NF2 | NM_000268 | BCL2A1 | NM_004049 |
| EGFR | NM_005228 | STK11 | NM_000455 | FLT4 | NM_182925 | NKX2-1 | NM_003317 | CDH20 | NM_051891 |
| ERBB2 | NM_004448 | TP53 | NM_000546 | GATA1 | NM_002049 | NTRK1 | NM_002529 | CDH5 | NM_001795 |
| ESR1 | NM_000125 | ABL2 | NM_005158 | GNAS | NM_016592 | PAX5 | NM_016734 | EPHA3 | NM_005233 |
| FGFR1 | NM_015850 | ATM | NM_000051 | HOXA3 | NM_030661 | PDGFRB | NM_002609 | EPHA5 | NM_004439 |
| FGFR2 | NM_000141 | AURKA | NM_003600 | HSP90AA1 | NM_005348 | PKHD1 | NM_138694 | EPHA7 | NM_004440 |
| FGFR3 | NM_000142 | AURKB | NM_004217 | IDH1 | NM_005896 | PRKDC | NM_006904 | EPHB1 | NM_004441 |
| FLT3 | NM_004119 | BCL2 | NM_000633 | IDH2 | NM_002168 | PTPN11 | NM_002834 | FOXP4 | NM_138457 |
| HRAS | NM_005343 | BCL2L1 | NM_001191 | IGF1R | NM_000875 | RAF1 | NM_002880 | GPR124 | NM_032777 |
| JAK2 | NM_004972 | BCL2L2 | NM_004050 | IGF2R | NM_000876 | RARA | NM_000964 | GUCY1A2 | NM_000855 |
| KIT | NM_000222 | BCL6 | NM_001706 | IKBKE | NM_014002 | RICTOR | NM_152756 | LRP1B | NM_018557 |
| KRAS | NM_004985 | BRCA1 | NM_007294 | INHBA | NM_002192 | RPTOR | NM_020761 | LTK | NM_002344 |
| MAP2K1 | NM_002755 | BRCA2 | NM_000059 | IRS2 | NM_003749 | RUNX1 | NM_001754 | PAK3 | NM_002578 |
| MAP2K2 | NM_030662 | CBL | NM_005138 | JAK3 | NM_000215 | SMAD2 | NM_005901 | PLCG1 | NM_002660 |
| MET | NM_000245 | CCNE1 | NM_001238 | KDR | NM_002253 | SMAD3 | NM_005902 | PTPRD | NM_002839 |
| MLL | NM_005933 | CDH1 | NM_004360 | MAP2K4 | NM_003010 | SMAD4 | NM_005359 | TBX22 | NM_016954 |
| MYC | NM_002467 | CDH2 | NM_001792 | MCL1 | NM_021960 | SMARCA4 | NM_003072 | USP9X | NM_001039590 |

| Gene | Group | # markers | RefSeq |
|---|---|---|---|
| CDKN2A | Del. A | 52 | NM_000077 |
| MAP2K4 | Del. B | 118 | NM_003010 |
| PTEN | Del. A | 97 | NM_000314 |
| RB1 | Del. A | 105 | NM_000321 |
| WT1 | Del. B | 94 | NM_000378 |

| | |
|---|---|
| Exons | 45 |
| Introns | −2 |
| PGx | −2 |
| Amp/Del | 4 |
| Exons + Intros | 152 |
| Ex + Int + PGx | 184 |

SUPPLEMENTARY TABLE 1b-continued genes sequenced across selected introns (n = 14)

| Gene | RefSeq | Introns sequenced |
|---|---|---|
| RAF1 | NM_002880 | 5, 6, 7, 8, 9 |
| RARA | NM_000964 | 2 |
| RET | NM_020630 | 9, 10, 11 |
| TMPRSS2 | NM_005656 | 1, 2 |

SUPPLEMENTARY TABLE 2a a Alterations in 40 CRC cases

| Sample | Total alterations | Substitutions | INDELs | Copy number changes | Rearrangement | APC | TP53 | KRAS | BRAF | FBXW7 |
|---|---|---|---|---|---|---|---|---|---|---|
| SM77E | 3 | 3 | | | | S1346* R213* | R213* | | | |
| SM1B | 3 | 3 | | | | D13941s*21 | R243W | | | |
| SM41E | 3 | 2 | 1 | | | DEL | G245S | G12A | | |
| SMB8E | 8 | 3 | 3 | | | DEL | R273CR181C | | V600E | DEL |
| SM75 | 3 | 1 | 2 | | | DEL DEL | C242F | | | |
| SM16 | 2 | 1 | 1 | | | E130012*4 | R306* | | | |
| SM21 | 4 | 4 | | | | E1353* E1374* E1544* | R175H | | | |
| SM0 | 3 | 2 | 1 | | | DEL | V272M | | | |
| SM7 | 3 | 2 | 1 | | | G1288* DEL | R248W | | | |
| SM42E | 2 | 2 | | | | K1370* | | G12V | | |
| SM83 | 2 | 2 | | | | K534* | C238Y | | | |
| SM20 | 4 | 3 | 1 | | | L14881A*19 R213* | | G12A | | |
| SM32 | 3 | 2 | 1 | | | P1324K*91 Q1406* | K132R | | | |
| SM40 | 3 | 1 | 2 | | | P1373K*42 DEL | C176Y | | | |
| SM4 | 4 | 3 | | | | Q1294* | | G12D | | R278* |
| SM6 | 4 | 3 | | 1 | | Q1406* L1120S | R2BOT | | | |
| SM2B | 3 | 3 | | | | Q1429* | | G12C | | |
| SM23 | 4 | 4 | | | | Q160V* | | | V600E | |
| SM91 | 3 | 2 | 1 | | | Q789* DEL | L194F | | | |
| SM8B | 3 | 2 | 1 | | | R139918*9 R1450* | E258G | | | R858* |
| SM8E | 9 | 3 | 8 | | | DEL | R196* | | V600E | |
| SM45 | 3 | 3 | | | | R213* R216* | R262W | G12V | | |
| SM100E | 3 | 2 | 1 | | | C1252* R232* | V122fs*26 | | | |
| SM67 | 9 | 2 | 1 | | | Q1131* | | | | |
| SM110E | 3 | 2 | 1 | | | R564* R584* | F212fs*3 | G12V | | |
| SM3 | 4 | 3 | | 1 | | E1322* S1465fs*3 | R282W | | | |
| SM64 | 5 | 1 | 4 | | | INS | DEL | | V600E | INS |
| SM29 | 3 | 1 | | 1 | 1 | | C135F | | | |
| SM14 | 2 | 1 | 1 | | | | DEL | G12V | | |
| SM13E | 1 | | 1 | | | | DEL | | | |
| SM34 | 1 | | 1 | | | | E204fs*43 | | | |
| SM19 | 4 | 2 | 2 | | | | E258A | | V600E | S688fs*28 |
| SM36E | 3 | 0 | 2 | | 1 | | INS | | | |
| SM12 | 7 | 3 | 4 | | | | P260H | | V600E | |
| SM11 | 2 | 2 | | | | | R248W | G12V | | |
| SM30 | 3 | 2 | 1 | | | | R273C DEL | | | |
| SM73 | 2 | 2 | | | | | S240R | | | |
| SM74NE | 2 | 2 | | | | | V173M | G12C | | |
| SM61 | 1 | 1 | | | | | | | | |
| SM78E | 0 | | | | | | | | | |
| Total | 125 | 80 | 39 | 4 | 2 | 42 | 34 | 10 | 6 | 5 |

SUPPLEMENTARY TABLE 2a-continued

| Sample | CDH1 | MYC | ATM | BCL2L1 | BRCA2 | ERBB3 | GNAS | PIK3CA | SMAD4 | ALK |
|---|---|---|---|---|---|---|---|---|---|---|
| SM77E | | | | | | | | | | |
| SM1B | | | | | | | | | S434* | |
| SM41E | | | | | | | | | | |
| SMB8E | | | | DEL | | | | | | |
| SM75 | | | | | | | | | | |
| SM16 | | | | | | | | | | |
| SM21 | | | | | | G284R | | | | |
| SM0 | | | | | | | | | | |
| SM7 | | | | | | | | | | |
| SM42E | | | | | | | | | | |
| SM83 | | | | | | | | | | |
| SM20 | | | | | | | | E645K | | |
| SM32 | | | | | | | | | | |
| SM40 | | | | | | | | | | |
| SM4 | | | | | | | | | | |
| SM6 | | | | | | | | | | |
| SM2B | | | | | | | | E545K | | |
| SM23 | | | | | | V104M | R201H | | | |
| SM91 | | | | | | | | | | |
| SM8B | | | | | | | | | | |
| SM8E | P1281s*39 | | DEL | | | | | | | |
| SM45 | | | | | | | | | | |
| SM100E | | | | | | | | | | |
| SM67 | | | | Amp | | | | | | |
| SM110E | | | | | | | | | | |
| SM3 | | | | Amp | | | | | | |
| SM64 | | | | | | | | | | |
| SM29 | | Amp | | | | | | | | Rearranged |
| SM14 | | | | | | | | | | |
| SM13E | | | | | | | | | | |
| SM34 | | | | | | | | | | |
| SM19 | | | | | | | | | DEL | |
| SM36E | R74* | | | | S1982fs*22 | | | | | |
| | P201fs*14 | | | | | | | | | |
| SM12 | P126fs*89 | | R1876* | | | | | | | |
| SM11 | | | | | | | | | | |
| SM30 | | | | | | | | | A118V | |
| SM73 | | | | | | | | | | |
| SM74NE | | | | | | | | | | |
| SM61 | | | | | | | 201H | | | |
| SM78E | | | | | | | | | | |
| Total | 4 | 3 | 2 | 2 | 2 | 2 | 2 | 2 | 2 | 1 |

| Sample | CDK8 | LRP1B | MSH6 | RICTOR | SMAD2 | STK11 |
|---|---|---|---|---|---|---|
| SM77E | | | | | | |
| SM1B | | | | | S434* | |
| SM41E | | | | | | |
| SMB8E | | | | | | |
| SM75 | | | | | | |
| SM16 | | | | | | |
| SM21 | | | | | | |
| SM0 | | | | | | |
| SM7 | | | | | | |
| SM42E | | | | | | |
| SM83 | | | | | | |
| SM20 | | | | | | |
| SM32 | | | | | | |
| SM40 | | | | | | |
| SM4 | | | | | | |
| SM6 | Amp | | | | | |
| SM2B | | | | | | |
| SM23 | | | | | | |
| SM91 | | | | | | |
| SM8B | | | DEL, | DEL | | |
| SM8E | | | | | | |
| SM45 | | | | | | |
| SM100E | | | | | | |
| SM67 | | | | | | |
| SM110E | | | | | | |
| SM3 | | | | | | |
| SM64 | | | | | | |
| SM29 | | | | | | |
| SM14 | | | | | | |
| SM13E | | | | | | |

SUPPLEMENTARY TABLE 2a-continued

| Sample | | | | | | | | | | | |
|---|---|---|---|---|---|---|---|---|---|---|---|
| SM34 | | | | | | | | | | | |
| SM19 | | | | | | | | | | | |
| SM36E | | | | | | Rearranged | | | | | |
| SM12 | | | | P1037fs*6 | | | | | | | |
| SM11 | | | | | | | | | | | |
| SM30 | | | | | | | | | | | |
| SM73 | | | | | | | | | | Q214R | |
| SM74NE | | | | | | | | | | | |
| SM61 | | | | | | | | | | | |
| SM78E | | | | | | | | | | | |
| Total | 1 | 1 | 1 | 1 | | 1 | | 1 | | | | b Alterations in 24 NSCLC cases

| Sample | Total alterations | Substitutions | Total INDELs | Copy number changes | Gene fusion | KRAS | TP63 | STK11 | LAP1B | JAK2 | CTNNB1 | RET | EGFR |
|---|---|---|---|---|---|---|---|---|---|---|---|---|---|
| SM109 | 1 | 1 | | | | D1NJC | | | | | | | |
| SM86 | 4 | 4 | | | | G12C | | | | V617F | 135S | | |
| SM51 | 3 | 3 | | | | G12C | | E165* | | | | | |
| SM71E | 1 | 1 | | | | G12C | | | | | | | |
| SM89 | 2 | 1 | 1 | | | G12F | | | | | | | |
| SM90 | 2 | 2 | | | | G12V | M2371 | | | | | | |
| SM96 | 3 | 3 | | | | G12V | | | Q2940* | | | | |
| SM44 | 3 | 2 | 1 | | | G12V | | DEL | | | S37Y | | |
| SM7DE | 1 | 1 | | | | G12V | | | | | | | |
| SM107 | 1 | 1 | | | | G12A | | | | | | | |
| 5M91A3 | 7 | 6 | 1 | | | | C229fs*10 | D194Y | K4112* | V617F | | | |
| SM93 | 2 | 2 | | | | | C242F | | | | | | |
| SM63 | 1 | 1 | | | | | G2455 | | | | | | |
| SM48 | 3 | 2 | 1 | | | | K132* | | E3058* | | | | |
| SM114 | 3 | 1 | | 1 | 1 | | R24BL | Hom del | | | | FUSION | |
| SM53 | 3 | 1 | 1 | 1 | | | Y163C | | | | | | |
| SM92 | 8 | 4 | | 2 | | | | | | V617F | | | |
| SM87 | 2 | | | 2 | | | | | | | | | AMP D770_M771 insSVD |
| SM64E | 1 | | 1 | | | | | | | | | | |
| SM113 | 1 | | 1 | | | | | | | | | | |
| SM46 | 0 | | | | | | | | | | | | |
| SM112 | 0 | | | | | | | | | | | | |
| SM4DASE | 0 | | | | | | | | | | | | |
| SM55 | 0 | | | | | | | | | | | | |
| Total | 50 | 36 | 7 | 6 | 1 | 10 | 7 | 4 | 3 | 3 | 2 | 1 | 2 |

| Sample | BRAF | CDKN2A | MDN2 | PIK3CA | ATM | T6C1 | CDNE1 | NF1 | RB1 | APC | MLH1 | MSH6 | CCK4 |
|---|---|---|---|---|---|---|---|---|---|---|---|---|---|
| SM109 | | | | | | | | | | | | | |
| SM86 | | | | E645K | | | | | | | | | |
| SM51 | G468A | | | | | | | | | | | | |
| SM71E | | | | | | | | | | | | | |
| SM89 | | | | | DEL | | | | | | | | |
| SM90 | | | | | | | | | | | | | |
| SM96 | | H83Y | | | | | | | | | | | |
| SM44 | | | | | | | | | | | | | |
| SM7DE | | | | | | | | | | | | | |
| SM107 | | | | | | | | | | | | | |
| 5M91A3 | | | | | | | | | Y1635* | E290 | L11295 | | |
| SM93 | | | | | | | | | | | E13* | | |
| SM63 | | | | | | | | | | | | | |
| SM48 | | DEL | | | | | | | | | | | |
| SM114 | | | | | | | | | | | | | |
| SM53 | | | | | | | INS | AMP | | | | | |
| SM92 | G458V | | AMP | N345K | | | | | | | | V50RA | AMP |
| SM87 | | | AMP | | | | | | | | | | |
| SM64E | | | | | | | | | | | | | |
| SM113 | | | | | DEL | | | | | | | | |
| SM46 | | | | | | | | | | | | | |
| SM112 | | | | | | | | | | | | | |
| SM4DA5E | | | | | | | | | | | | | |
| SM55 | | | | | | | | | | | | | |
| Total | 2 | 2 | 2 | 2 | 2 | 1 | 1 | 1 | 1 | 1 | 1 | 1 | 1 |

SUPPLEMENTARY TABLE 3 alterations that could be linked to a clinical treatment option or clinical trial of novel targeted therapies

| Gene | Mutated Samples | Potential therapeutic treatment or clinical trial |
|---|---|---|
| TP53 | 32 | Presently unknown |
| APC | 27 | Presently unknown |
| KRAS | 10 | Resistance to cetuximab and panitumumab |
| BRAF | 6 | Resistance to cetuximab and panitumumab |
| FBXW7 | 5 | Potential resistance to tubulins |
| ATM | 2 | PARP inhibitors |
| BCL2L1 | 2 | Presently unknown |
| BRCA2 | 2 | PARP inhibitors |
| CDH1 | 2 | Presently unknown |
| ERBB3 | 2 | Presently unknown |
| GNAS | 2 | MEK or ERK inhibitors |
| PIK3CA | 2 | PI3 kinase/mTOR inhibitors |
| SMAD4 | 2 | prognostic poor |
| ALK | 1 | ALK inhibitors e.g. Crizotinib |
| CDK8 | 1 | CDK inhibitors e.g PD0332991 |
| LRP1B | 1 | Presently unknown |
| MYC | 1 | Presently unknown |
| MSH6 | 1 | Prognostic factor |
| RICTOR | 1 | Presently unknown |
| SMAD2 | 1 | Presently unknown |
| STK11 | 1 | Presently unknown |

SUPPLEMENTARY TABLE 4

Distribution of 51 mutations across 21 mutated NSCLC genes

| Gene | Mutated Samples | Total Mutations | Non Synonymous | Nonsense | INDEL frameshift | Amplification | Homozygous Deletion | Gene Fusion |
|---|---|---|---|---|---|---|---|---|
| KRAS | 10 | 10 | 10 | — | — | — | — | — |
| TP53 | 7 | 7 | 5 | 1 | 1 | — | — | — |
| STK11 | 4 | 4 | 1 | 1 | 1 | — | 1 | — |
| LRP1B | 3 | 3 | — | 3 | — | — | — | — |
| JAK2 | 3 | 3 | 3 | — | — | — | — | — |
| EGFR | 2 | 2 | — | — | — | 1 | — | — |
| BRAF | 2 | 2 | 2 | — | — | — | — | — |
| CDKN2A | 2 | 2 | 1 | — | — | — | — | — |
| RET | 1 | 1 | — | — | — | — | — | 1 |
| CTNNB1 | 2 | 2 | 2 | — | — | — | — | — |
| MDM2 | 2 | 2 | — | — | — | 2 | — | — |
| PIK3CA | 2 | 2 | 2 | — | — | — | — | — |
| ATM | 2 | 2 | — | — | 2 | — | — | — |
| TSCI | 1 | 1 | — | — | 1 | — | — | — |
| CCNE1 | 1 | 1 | — | — | — | 1 | — | — |
| NF1 | 1 | 1 | — | 1 | — | — | — | — |
| RB1 | 1 | 1 | — | 1 | — | — | — | — |
| APC | 1 | 1 | 1 | — | — | — | — | — |
| MLH1 | 1 | 1 | — | 1 | — | — | — | — |
| MSH6 | 1 | 1 | 1 | — | — | — | — | — |
| CDK4 | 1 | 1 | — | — | — | 1 | — | — |

SUPPLEMENTARY TABLE 5

NSCLC alteration that could be linked to a clinical treatment option or clinical trial of novel targeted therapies

| Gene | Total Mutations | Potential therapeutic treatment or clinical trial |
|---|---|---|
| KRAS | 10 | Resistance to EGFR kinase inhibitors, clinical trials of PI3K and MEK inhibitors |
| STK11 | 4 | Presently unknown |
| JAK2 | 3 | JAK2 inhibitors |
| EGFR | 2 | Erlotinib or gefitinib |
| BRAF | 2 | Vemurafenib and GSK 2118436 |
| CDKN2A | 2 | CDK inhibitors e.g., PD0332991 |
| RET | 2 | RET inhibitors e.g., Sorafanib or sunitinib |
| CTNNB1 | 2 | Presently unknown |
| MDM2 | 2 | Nutlins |
| PIK3CA | 2 | PI3 kinase/mTOR inhibitors |
| ATM | 2 | PARP inhibitors |
| TSC1 | 1 | mTOR inhibitors |
| CCNE1 | 1 | CDK4 inhibitors e.g., PD0332991 |
| NF1 | 1 | Presently unknown |
| RB1 | 1 | Presently unknown |
| MLH1 | 1 | Presently unknown |
| MSH6 | 1 | Presently unknown |
| CDK4 | 1 | CDK4 inhibitors e.g., PD0332991 |

ADDITIONAL REFERENCES

James et al., *Nucl. Acids Res.* 16:1999-2014, 1988.

Levin et al., *Genome Biol.* 10:R115, 2009.

Li and Durbin, *Bioinformatics* 26:589-95, 2010.

Li et al., *Bioinformatics* 25:2078-9, 2009.

online at picard.sourceforge.net

McKenna et al., *Genome Res.* 20:1297-303, 2010.

Forbes et al, *Nucl. Acids Res.* 39 (suppl 1): D945-D950, 2011.

Smigielski et al., *Nucl. Acids Res.* 28:352-355, 2000.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by the COSMIC database, available on the worldwide web at sanger.ac.uk/genetics/CGP/cosmic/; and the Institute for Genomic Research (TIGR) on the world wide web at tigr.org and/or the National Center for Biotechnology Information (NCBI) on the world wide web at ncbi.nlm.nih.gov.

EQUIVALENTS

Those skilled in the art will recognize, or be able to ascertain using no more than routine experimentation, many equivalents to the specific embodiments described herein. Such equivalents are intended to be encompassed by the following claims.

We claim:

1. A method of treating a subject having a lung cancer or a colorectal cancer, comprising:
   responsive to the determination of the presence of a Kinesin Family Member 5B (KIF5B)-RET fusion polypeptide or a nucleic acid molecule encoding the KIF5B-RET fusion polypeptide, administering to the subject an effective amount of a kinase inhibitor or a RET-specific inhibitor,
   wherein the KIF5B-RET fusion polypeptide comprises a RET tyrosine kinase domain and a KIF5B kinesin motor domain and coiled-coil domain, of SEQ ID NO:2,
   thereby treating the cancer in the subject.

2. The method of claim 1, wherein said kinase inhibitor is a multi-kinase inhibitor.

3. The method of claim 1, wherein the kinase inhibitor is chosen from lenvatinib, sorafenib, sunitinib, vandetanib, NVP-AST487, regorafenib, motesanib, cabozantinib, apatinib, or DCC-2157.

4. The method of claim 1, wherein the presence of the nucleic acid molecule encoding the KIF5B-RET fusion polypeptide is determined by sequencing.

5. The method of claim 1, wherein said cancer is a colorectal cancer.

6. The method of claim 1, wherein said cancer is lung cancer.

7. The method of claim 6, wherein said lung cancer is chosen from: small cell lung cancer (SCLC), adenocarcinoma of the lung, bronchogenic carcinoma, or a combination thereof.

8. The method of claim 6, wherein the lung cancer is non-small cell lung cancer (NSCLC).

9. The method of claim 6, wherein the lung cancer is squamous cell carcinoma (SCC).

10. The method of claim 6, wherein the method comprises administering a multi-kinase inhibitor to the subject.

11. The method of claim 1, wherein the method comprises administering a RET-specific inhibitor.

12. The method of claim 1, wherein the kinase inhibitor is sorafenib.

13. The method of claim 1, wherein the kinase inhibitor is sunitinib.

14. The method of claim 1, wherein the kinase inhibitor is vandetanib.

15. The method of claim 1, wherein the kinase inhibitor is NVP-AST487.

16. The method of claim 1, wherein the kinase inhibitor inhibits the expression of the nucleic acid molecule encoding the KIF5B-RET fusion polypeptide.

17. The method of claim 1, wherein the kinase inhibitor or RET-specific inhibitor is administered in combination with a second therapeutic agent or a different therapeutic modality.

18. The method of claim 17, wherein the KIF5B-RET fusion polypeptide or the nucleic acid molecule encoding the KIF5B-RET fusion polypeptide is detected prior to initiating, during, or after, administering the second therapeutic agent or the different therapeutic modality to the subject.

19. The method of claim 1, wherein the KIF5B-RET fusion polypeptide or the nucleic acid molecule encoding the KIF5B-RET fusion polypeptide is detected at the time of diagnosis with the cancer.

20. The method of claim 1, wherein said KIF5B-RET fusion polypeptide or nucleic acid molecule encoding said KIF5B-RET fusion polypeptide is an in-frame fusion comprising at least exon 15 of KIF5B and at least exon 12 of RET.

21. The method of claim 1, wherein said nucleic acid molecule encoding the KIF5B-RET fusion polypeptide comprises nucleotides 1720-1731, 1717-1734, or 1714-1737 of SEQ ID NO:1.

22. The method of claim 1, wherein the cancer is a lung adenocarcinoma and the kinase inhibitor is cabozantinib.

23. The method of claim 11, wherein the RET-specific inhibitor is an inhibitor of expression of the nucleic acid molecule encoding the KIF5B-RET fusion polypeptide, or a transcriptional regulatory region that blocks or reduces mRNA expression of the nucleic acid molecule encoding the KIF5B-RET fusion polypeptide.

24. The method of claim 23, wherein the RET-specific inhibitor is selected from an antisense molecule, a ribozyme, an RNAi molecule, or a triple helix molecule that hybridizes to an encoding region or a transcription regulatory region of said nucleic acid molecule encoding the KIF5B-RET fusion polypeptide thereby blocking or reducing mRNA expression of the nucleic acid molecule encoding the KIF5B-RET fusion polypeptide.

25. The method of claim 11, wherein the RET-specific inhibitor is a small molecule.

26. A method of treating a subject having lung cancer, comprising:
responsive to the determination of the presence of a Kinesin Family Member 5B (KIF5B)-RET fusion polypeptide or a nucleic acid molecule encoding the KIF5B-RET fusion polypeptide, administering to the subject an effective amount of a kinase inhibitor chosen from sorafenib, sunitinib, vandetanib, or cabozantinib,
wherein the KIF5B-RET fusion polypeptide comprises a RET tyrosine kinase domain and a KIF5B kinesin motor domain and coiled-coil domain, of SEQ ID NO:2,
thereby treating the lung cancer in the subject.

27. A method of treating a subject having lung cancer, comprising:
determining the presence of a Kinesin Family Member 5B (KIF5B)-RET fusion polypeptide or a nucleic acid molecule encoding the KIF5B-RET fusion polypeptide in the subject; and
responsive to the determination of the presence of the KIF5B-RET fusion polypeptide or a nucleic acid molecule encoding the KIF5B-RET fusion polypeptide, administering to the subject an effective amount of a kinase inhibitor chosen from sorafenib, sunitinib, vandetanib, or cabozantinib,
wherein the KIF5B-RET fusion polypeptide comprises a RET tyrosine kinase domain and a KIF5B kinesin motor domain and coiled-coil domain, of SEQ ID NO:2, thereby treating the lung cancer in the subject.

* * * * *

SEQUENCE LISTING

<160> NUMBER OF SEQ ID NOS: 9

<210> SEQ ID NO 1
<211> LENGTH: 2934
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(2931)

<400> SEQUENCE: 1

```
atg gcg gac ctg gcc gag tgc aac atc aaa gtg atg tgt cgc ttc aga      48
Met Ala Asp Leu Ala Glu Cys Asn Ile Lys Val Met Cys Arg Phe Arg
1               5                   10                  15 cct ctc aac gag tct gaa gtg aac cgc ggc gac aag tac atc gcc aag      96
Pro Leu Asn Glu Ser Glu Val Asn Arg Gly Asp Lys Tyr Ile Ala Lys
            20                  25                  30 ttt cag gga gaa gac acg gtc gtg atc gcg tcc aag cct tat gca ttt     144
Phe Gln Gly Glu Asp Thr Val Val Ile Ala Ser Lys Pro Tyr Ala Phe
        35                  40                  45 gat cgg gtg ttc cag tca agc aca tct caa gag caa gtg tat aat gac     192
Asp Arg Val Phe Gln Ser Ser Thr Ser Gln Glu Gln Val Tyr Asn Asp
    50                  55                  60 tgt gca aag aag att gtt aaa gat gta ctt gaa gga tat aat gga aca     240
Cys Ala Lys Lys Ile Val Lys Asp Val Leu Glu Gly Tyr Asn Gly Thr
65                  70                  75                  80 ata ttt gca tat gga caa aca tcc tct ggg aag aca cac aca atg gag     288
Ile Phe Ala Tyr Gly Gln Thr Ser Ser Gly Lys Thr His Thr Met Glu
                85                  90                  95 ggt aaa ctt cat gat cca gaa ggc atg gga att att cca aga ata gtg     336
Gly Lys Leu His Asp Pro Glu Gly Met Gly Ile Ile Pro Arg Ile Val
            100                 105                 110 caa gat att ttt aat tat att tac tcc atg gat gaa aat ttg gaa ttt     384
Gln Asp Ile Phe Asn Tyr Ile Tyr Ser Met Asp Glu Asn Leu Glu Phe
        115                 120                 125 cat att aag gtt tca tat ttt gaa ata tat ttg gat aag ata agg gac     432
His Ile Lys Val Ser Tyr Phe Glu Ile Tyr Leu Asp Lys Ile Arg Asp
    130                 135                 140 ctg tta gat gtt tca aag acc aac ctt tca gtt cat gaa gac aaa aac     480
Leu Leu Asp Val Ser Lys Thr Asn Leu Ser Val His Glu Asp Lys Asn
145                 150                 155                 160 cga gtt ccc tat gta aag ggg tgc aca gag cgt ttt gta tgt agt cca     528
Arg Val Pro Tyr Val Lys Gly Cys Thr Glu Arg Phe Val Cys Ser Pro
                165                 170                 175 gat gaa gtt atg gat acc ata gat gaa gga aaa tcc aac aga cat gta     576
Asp Glu Val Met Asp Thr Ile Asp Glu Gly Lys Ser Asn Arg His Val
            180                 185                 190 gca gtt aca aat atg aat gaa cat agc tct agg agt cac agt ata ttt     624
Ala Val Thr Asn Met Asn Glu His Ser Ser Arg Ser His Ser Ile Phe
        195                 200                 205 ctt att aat gtc aaa caa gag aac aca caa acg gaa caa aag ctg agt     672
Leu Ile Asn Val Lys Gln Glu Asn Thr Gln Thr Glu Gln Lys Leu Ser
    210                 215                 220 gga aaa ctt tat ctg gtt gat tta gct ggt agt gaa aag gtt agt aaa     720
Gly Lys Leu Tyr Leu Val Asp Leu Ala Gly Ser Glu Lys Val Ser Lys
225                 230                 235                 240 act gga gct gaa ggt gct gtg ctg gat gaa gct aaa aac atc aac aag     768
Thr Gly Ala Glu Gly Ala Val Leu Asp Glu Ala Lys Asn Ile Asn Lys
                245                 250                 255
```

-continued

| | | |
|---|---|---|
| tca ctt tct gct ctt gga aat gtt att tct gct ttg gct gag ggt agt<br>Ser Leu Ser Ala Leu Gly Asn Val Ile Ser Ala Leu Ala Glu Gly Ser<br>260 265 270 | 816 | |
| aca tat gtt cca tat cga gat agt aaa atg aca aga atc ctt caa gat<br>Thr Tyr Val Pro Tyr Arg Asp Ser Lys Met Thr Arg Ile Leu Gln Asp<br>275 280 285 | 864 | |
| tca tta ggt ggc aac tgt aga acc act att gta att tgc tgc tct cca<br>Ser Leu Gly Gly Asn Cys Arg Thr Thr Ile Val Ile Cys Cys Ser Pro<br>290 295 300 | 912 | |
| tca tca tac aat gag tct gaa aca aaa tct aca ctc tta ttt ggc caa<br>Ser Ser Tyr Asn Glu Ser Glu Thr Lys Ser Thr Leu Leu Phe Gly Gln<br>305 310 315 320 | 960 | |
| agg gcc aaa aca att aag aac aca gtt tgt gtc aat gtg gag tta act<br>Arg Ala Lys Thr Ile Lys Asn Thr Val Cys Val Asn Val Glu Leu Thr<br>325 330 335 | 1008 | |
| gca gaa cag tgg aaa aag aag tat gaa aaa gaa aaa gaa aaa aat aag<br>Ala Glu Gln Trp Lys Lys Lys Tyr Glu Lys Glu Lys Glu Lys Asn Lys<br>340 345 350 | 1056 | |
| atc ctg cgg aac act att cag tgg ctt gaa aat gag ctc aac aga tgg<br>Ile Leu Arg Asn Thr Ile Gln Trp Leu Glu Asn Glu Leu Asn Arg Trp<br>355 360 365 | 1104 | |
| cgt aat ggg gag acg gtg cct att gat gaa cag ttt gac aaa gag aaa<br>Arg Asn Gly Glu Thr Val Pro Ile Asp Glu Gln Phe Asp Lys Glu Lys<br>370 375 380 | 1152 | |
| gcc aac ttg gaa gct ttc aca gtg gat aaa gat att act ctt acc aat<br>Ala Asn Leu Glu Ala Phe Thr Val Asp Lys Asp Ile Thr Leu Thr Asn<br>385 390 395 400 | 1200 | |
| gat aaa cca gca acc gca att gga gtt ata gga aat ttt act gat gct<br>Asp Lys Pro Ala Thr Ala Ile Gly Val Ile Gly Asn Phe Thr Asp Ala<br>405 410 415 | 1248 | |
| gaa aga aga aag tgt gaa gaa gaa att gct aaa tta tac aaa cag ctt<br>Glu Arg Arg Lys Cys Glu Glu Glu Ile Ala Lys Leu Tyr Lys Gln Leu<br>420 425 430 | 1296 | |
| gat gac aag gat gaa gaa att aac cag caa agt caa ctg gta gag aaa<br>Asp Asp Lys Asp Glu Glu Ile Asn Gln Gln Ser Gln Leu Val Glu Lys<br>435 440 445 | 1344 | |
| ctg aag acg caa atg ttg gat cag gag gag ctt ttg gca tct acc aga<br>Leu Lys Thr Gln Met Leu Asp Gln Glu Glu Leu Leu Ala Ser Thr Arg<br>450 455 460 | 1392 | |
| agg gat caa gac aat atg caa gct gag ctg aat cgc ctt caa gca gaa<br>Arg Asp Gln Asp Asn Met Gln Ala Glu Leu Asn Arg Leu Gln Ala Glu<br>465 470 475 480 | 1440 | |
| aat gat gcc tct aaa gaa gaa gtg aaa gaa gtt tta cag gcc cta gaa<br>Asn Asp Ala Ser Lys Glu Glu Val Lys Glu Val Leu Gln Ala Leu Glu<br>485 490 495 | 1488 | |
| gaa ctt gct gtc aat tat gat cag aag tct cag gaa gtt gaa gac aaa<br>Glu Leu Ala Val Asn Tyr Asp Gln Lys Ser Gln Glu Val Glu Asp Lys<br>500 505 510 | 1536 | |
| act aag gaa tat gaa ttg ctt agt gat gaa ttg aat cag aaa tcg gca<br>Thr Lys Glu Tyr Glu Leu Leu Ser Asp Glu Leu Asn Gln Lys Ser Ala<br>515 520 525 | 1584 | |
| act tta gcg agt ata gat gct gag ctt cag aaa ctt aag gaa atg acc<br>Thr Leu Ala Ser Ile Asp Ala Glu Leu Gln Lys Leu Lys Glu Met Thr<br>530 535 540 | 1632 | |
| aac cac cag aaa aaa cga gca gct gag atg atg gca tct tta cta aaa<br>Asn His Gln Lys Lys Arg Ala Ala Glu Met Met Ala Ser Leu Leu Lys<br>545 550 555 560 | 1680 | |
| gac ctt gca gaa ata gga att gct gtg gga aat aat gat gta aag gag<br>Asp Leu Ala Glu Ile Gly Ile Ala Val Gly Asn Asn Asp Val Lys Glu | 1728 | |

-continued

```
                565                 570                 575
gat cca aag tgg gaa ttc cct cgg aag aac ttg gtt ctt gga aaa act    1776
Asp Pro Lys Trp Glu Phe Pro Arg Lys Asn Leu Val Leu Gly Lys Thr
            580                 585                 590 cta gga gaa ggc gaa ttt gga aaa gtg gtc aag gca acg gcc ttc cat    1824
Leu Gly Glu Gly Glu Phe Gly Lys Val Val Lys Ala Thr Ala Phe His
        595                 600                 605 ctg aaa ggc aga gca ggg tac acc acg gtg gcc gtg aag atg ctg aaa    1872
Leu Lys Gly Arg Ala Gly Tyr Thr Thr Val Ala Val Lys Met Leu Lys
    610                 615                 620 gag aac gcc tcc ccg agt gag ctg cga gac ctg ctg tca gag ttc aac    1920
Glu Asn Ala Ser Pro Ser Glu Leu Arg Asp Leu Leu Ser Glu Phe Asn
625                 630                 635                 640 gtc ctg aag cag gtc aac cac cca cat gtc atc aaa ttg tat ggg gcc    1968
Val Leu Lys Gln Val Asn His Pro His Val Ile Lys Leu Tyr Gly Ala
            645                 650                 655 tgc agc cag gat ggc ccg ctc ctc ctc atc gtg gag tac gcc aaa tac    2016
Cys Ser Gln Asp Gly Pro Leu Leu Leu Ile Val Glu Tyr Ala Lys Tyr
        660                 665                 670 ggc tcc ctg cgg ggc ttc ctc cgc gag agc cgc aaa gtg ggg cct ggc    2064
Gly Ser Leu Arg Gly Phe Leu Arg Glu Ser Arg Lys Val Gly Pro Gly
    675                 680                 685 tac ctg ggc agt gga ggc agc cgc aac tcc agc tcc ctg gac cac ccg    2112
Tyr Leu Gly Ser Gly Gly Ser Arg Asn Ser Ser Ser Leu Asp His Pro
690                 695                 700 gat gag cgg gcc ctc acc atg ggc gac ctc atc tca ttt gcc tgg cag    2160
Asp Glu Arg Ala Leu Thr Met Gly Asp Leu Ile Ser Phe Ala Trp Gln
705                 710                 715                 720 atc tca cag ggg atg cag tat ctg gcc gag atg aag ctc gtt cat cgg    2208
Ile Ser Gln Gly Met Gln Tyr Leu Ala Glu Met Lys Leu Val His Arg
            725                 730                 735 gac ttg gca gcc aga aac atc ctg gta gct gag ggg cgg aag atg aag    2256
Asp Leu Ala Ala Arg Asn Ile Leu Val Ala Glu Gly Arg Lys Met Lys
        740                 745                 750 att tcg gat ttc ggc ttg tcc cga gat gtt tat gaa gag gat tcc tac    2304
Ile Ser Asp Phe Gly Leu Ser Arg Asp Val Tyr Glu Glu Asp Ser Tyr
    755                 760                 765 gtg aag agg agc cag ggt cgg att cca gtt aaa tgg atg gca att gaa    2352
Val Lys Arg Ser Gln Gly Arg Ile Pro Val Lys Trp Met Ala Ile Glu
770                 775                 780 tcc ctt ttt gat cat atc tac acc acg caa agt gat gta tgg tct ttt    2400
Ser Leu Phe Asp His Ile Tyr Thr Thr Gln Ser Asp Val Trp Ser Phe
785                 790                 795                 800 ggt gtc ctg ctg tgg gag atc gtg acc cta ggg gga aac ccc tat cct    2448
Gly Val Leu Leu Trp Glu Ile Val Thr Leu Gly Gly Asn Pro Tyr Pro
            805                 810                 815 ggg att cct cct gag cgg ctc ttc aac ctt ctg aag acc ggc cac cgg    2496
Gly Ile Pro Pro Glu Arg Leu Phe Asn Leu Leu Lys Thr Gly His Arg
        820                 825                 830 atg gag agg cca gac aac tgc agc gag gag atg tac cgc ctg atg ctg    2544
Met Glu Arg Pro Asp Asn Cys Ser Glu Glu Met Tyr Arg Leu Met Leu
    835                 840                 845 caa tgc tgg aag cag gag ccg gac aaa agg ccg gtg ttt gcg gac atc    2592
Gln Cys Trp Lys Gln Glu Pro Asp Lys Arg Pro Val Phe Ala Asp Ile
850                 855                 860 agc aaa gac ctg gag aag atg atg gtt aag agg aga gac tac ttg gac    2640
Ser Lys Asp Leu Glu Lys Met Met Val Lys Arg Arg Asp Tyr Leu Asp
865                 870                 875                 880 ctt gcg gcg tcc act cca tct gac tcc ctg att tat gac gac ggc ctc    2688
```

```
Leu Ala Ala Ser Thr Pro Ser Asp Ser Leu Ile Tyr Asp Asp Gly Leu
                885                 890                 895 tca gag gag gag aca ccg ctg gtg gac tgt aat aat gcc ccc ctc cct      2736
Ser Glu Glu Glu Thr Pro Leu Val Asp Cys Asn Asn Ala Pro Leu Pro
            900                 905                 910 cga gcc ctc cct tcc aca tgg att gaa aac aaa ctc tat ggc atg tca      2784
Arg Ala Leu Pro Ser Thr Trp Ile Glu Asn Lys Leu Tyr Gly Met Ser
        915                 920                 925 gac ccg aac tgg cct gga gag agt cct gta cca ctc acg aga gct gat      2832
Asp Pro Asn Trp Pro Gly Glu Ser Pro Val Pro Leu Thr Arg Ala Asp
    930                 935                 940 ggc act aac act ggg ttt cca aga tat cca aat gat agt gta tat gct      2880
Gly Thr Asn Thr Gly Phe Pro Arg Tyr Pro Asn Asp Ser Val Tyr Ala
945                 950                 955                 960 aac tgg atg ctt tca ccc tca gcg gca aaa tta atg gac acg ttt gat      2928
Asn Trp Met Leu Ser Pro Ser Ala Ala Lys Leu Met Asp Thr Phe Asp
                965                 970                 975 agt taa                                                               2934
Ser

<210> SEQ ID NO 2
<211> LENGTH: 977
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Ala Asp Leu Ala Glu Cys Asn Ile Lys Val Met Cys Arg Phe Arg
1               5                   10                  15

Pro Leu Asn Glu Ser Glu Val Asn Arg Gly Asp Lys Tyr Ile Ala Lys
            20                  25                  30

Phe Gln Gly Glu Asp Thr Val Val Ile Ala Ser Lys Pro Tyr Ala Phe
        35                  40                  45

Asp Arg Val Phe Gln Ser Ser Thr Ser Gln Glu Gln Val Tyr Asn Asp
    50                  55                  60

Cys Ala Lys Lys Ile Val Lys Asp Val Leu Glu Gly Tyr Asn Gly Thr
65                  70                  75                  80

Ile Phe Ala Tyr Gly Gln Thr Ser Ser Gly Lys Thr His Thr Met Glu
                85                  90                  95

Gly Lys Leu His Asp Pro Glu Gly Met Gly Ile Ile Pro Arg Ile Val
            100                 105                 110

Gln Asp Ile Phe Asn Tyr Ile Tyr Ser Met Asp Glu Asn Leu Glu Phe
        115                 120                 125

His Ile Lys Val Ser Tyr Phe Glu Ile Tyr Leu Asp Lys Ile Arg Asp
    130                 135                 140

Leu Leu Asp Val Ser Lys Thr Asn Leu Ser Val His Glu Asp Lys Asn
145                 150                 155                 160

Arg Val Pro Tyr Val Lys Gly Cys Thr Glu Arg Phe Val Cys Ser Pro
                165                 170                 175

Asp Glu Val Met Asp Thr Ile Asp Glu Gly Lys Ser Asn Arg His Val
            180                 185                 190

Ala Val Thr Asn Met Asn Glu His Ser Ser Arg Ser His Ser Ile Phe
        195                 200                 205

Leu Ile Asn Val Lys Gln Glu Asn Thr Gln Thr Glu Gln Lys Leu Ser
    210                 215                 220
```

-continued

Gly Lys Leu Tyr Leu Val Asp Leu Ala Gly Ser Glu Lys Val Ser Lys
225                 230                 235                 240

Thr Gly Ala Glu Gly Ala Val Leu Asp Glu Ala Lys Asn Ile Asn Lys
            245                 250                 255

Ser Leu Ser Ala Leu Gly Asn Val Ile Ser Ala Leu Ala Glu Gly Ser
        260                 265                 270

Thr Tyr Val Pro Tyr Arg Asp Ser Lys Met Thr Arg Ile Leu Gln Asp
    275                 280                 285

Ser Leu Gly Gly Asn Cys Arg Thr Thr Ile Val Ile Cys Cys Ser Pro
290                 295                 300

Ser Ser Tyr Asn Glu Ser Glu Thr Lys Ser Thr Leu Leu Phe Gly Gln
305                 310                 315                 320

Arg Ala Lys Thr Ile Lys Asn Thr Val Cys Val Asn Val Glu Leu Thr
                325                 330                 335

Ala Glu Gln Trp Lys Lys Lys Tyr Glu Lys Glu Lys Glu Lys Asn Lys
            340                 345                 350

Ile Leu Arg Asn Thr Ile Gln Trp Leu Glu Asn Glu Leu Asn Arg Trp
        355                 360                 365

Arg Asn Gly Glu Thr Val Pro Ile Asp Glu Gln Phe Asp Lys Glu Lys
370                 375                 380

Ala Asn Leu Glu Ala Phe Thr Val Asp Lys Asp Ile Thr Leu Thr Asn
385                 390                 395                 400

Asp Lys Pro Ala Thr Ala Ile Gly Val Ile Gly Asn Phe Thr Asp Ala
                405                 410                 415

Glu Arg Arg Lys Cys Glu Glu Ile Ala Lys Leu Tyr Lys Gln Leu
            420                 425                 430

Asp Asp Lys Asp Glu Glu Ile Asn Gln Gln Ser Gln Leu Val Glu Lys
        435                 440                 445

Leu Lys Thr Gln Met Leu Asp Gln Glu Glu Leu Leu Ala Ser Thr Arg
    450                 455                 460

Arg Asp Gln Asp Asn Met Gln Ala Glu Leu Asn Arg Leu Gln Ala Glu
465                 470                 475                 480

Asn Asp Ala Ser Lys Glu Glu Val Lys Glu Val Leu Gln Ala Leu Glu
                485                 490                 495

Glu Leu Ala Val Asn Tyr Asp Gln Lys Ser Gln Glu Val Glu Asp Lys
            500                 505                 510

Thr Lys Glu Tyr Glu Leu Leu Ser Asp Glu Leu Asn Gln Lys Ser Ala
        515                 520                 525

Thr Leu Ala Ser Ile Asp Ala Glu Leu Gln Lys Leu Lys Glu Met Thr
    530                 535                 540

Asn His Gln Lys Lys Arg Ala Ala Glu Met Met Ala Ser Leu Leu Lys
545                 550                 555                 560

Asp Leu Ala Glu Ile Gly Ile Ala Val Gly Asn Asn Asp Val Lys Glu
                565                 570                 575

Asp Pro Lys Trp Glu Phe Pro Arg Lys Asn Leu Val Leu Gly Lys Thr
            580                 585                 590

Leu Gly Glu Gly Glu Phe Gly Lys Val Val Lys Ala Thr Ala Phe His
        595                 600                 605

Leu Lys Gly Arg Ala Gly Tyr Thr Thr Val Ala Val Lys Met Leu Lys
    610                 615                 620

Glu Asn Ala Ser Pro Ser Glu Leu Arg Asp Leu Leu Ser Glu Phe Asn
625                 630                 635                 640

Val Leu Lys Gln Val Asn His Pro His Val Ile Lys Leu Tyr Gly Ala

Cys Ser Gln Asp Gly Pro Leu Leu Ile Val Glu Tyr Ala Lys Tyr
            660                 665                 670

Gly Ser Leu Arg Gly Phe Leu Arg Glu Ser Arg Lys Val Gly Pro Gly
        675                 680                 685

Tyr Leu Gly Ser Gly Gly Ser Arg Asn Ser Ser Leu Asp His Pro
    690                 695                 700

Asp Glu Arg Ala Leu Thr Met Gly Asp Leu Ile Ser Phe Ala Trp Gln
705                 710                 715                 720

Ile Ser Gln Gly Met Gln Tyr Leu Ala Glu Met Lys Leu Val His Arg
                725                 730                 735

Asp Leu Ala Ala Arg Asn Ile Leu Val Ala Glu Gly Arg Lys Met Lys
            740                 745                 750

Ile Ser Asp Phe Gly Leu Ser Arg Asp Val Tyr Glu Glu Asp Ser Tyr
        755                 760                 765

Val Lys Arg Ser Gln Gly Arg Ile Pro Val Lys Trp Met Ala Ile Glu
770                 775                 780

Ser Leu Phe Asp His Ile Tyr Thr Thr Gln Ser Asp Val Trp Ser Phe
785                 790                 795                 800

Gly Val Leu Leu Trp Glu Ile Val Thr Leu Gly Gly Asn Pro Tyr Pro
                805                 810                 815

Gly Ile Pro Pro Glu Arg Leu Phe Asn Leu Leu Lys Thr Gly His Arg
            820                 825                 830

Met Glu Arg Pro Asp Asn Cys Ser Glu Glu Met Tyr Arg Leu Met Leu
        835                 840                 845

Gln Cys Trp Lys Gln Glu Pro Asp Lys Arg Pro Val Phe Ala Asp Ile
850                 855                 860

Ser Lys Asp Leu Glu Lys Met Met Val Lys Arg Arg Asp Tyr Leu Asp
865                 870                 875                 880

Leu Ala Ala Ser Thr Pro Ser Asp Ser Leu Ile Tyr Asp Asp Gly Leu
                885                 890                 895

Ser Glu Glu Glu Thr Pro Leu Val Asp Cys Asn Asn Ala Pro Leu Pro
            900                 905                 910

Arg Ala Leu Pro Ser Thr Trp Ile Glu Asn Lys Leu Tyr Gly Met Ser
        915                 920                 925

Asp Pro Asn Trp Pro Gly Glu Ser Pro Val Pro Leu Thr Arg Ala Asp
930                 935                 940

Gly Thr Asn Thr Gly Phe Pro Arg Tyr Pro Asn Asp Ser Val Tyr Ala
945                 950                 955                 960

Asn Trp Met Leu Ser Pro Ser Ala Ala Lys Leu Met Asp Thr Phe Asp
                965                 970                 975

Ser

<210> SEQ ID NO 3
<211> LENGTH: 3303
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(3300)

<400> SEQUENCE: 3 atg gcg aag gcg acg tcc ggt gcc gcg ggg ctg cgt ctg ctg ttg ctg      48

```
Met Ala Lys Ala Thr Ser Gly Ala Ala Gly Leu Arg Leu Leu Leu Leu
1               5                   10                  15 ctg ctg ctg ccg ctg cta ggc aaa gtg gca ttg ggc ctc tac ttc tcg     96
Leu Leu Leu Pro Leu Leu Gly Lys Val Ala Leu Gly Leu Tyr Phe Ser
                20                  25                  30 agg gat gct tac tgg gag aag ctg tat gtg gac cag gca gcc ggc acg    144
Arg Asp Ala Tyr Trp Glu Lys Leu Tyr Val Asp Gln Ala Ala Gly Thr
            35                  40                  45 ccc ttg ctg tac gtc cat gcc ctg cgg gac gcc cct gag gag gtg ccc    192
Pro Leu Leu Tyr Val His Ala Leu Arg Asp Ala Pro Glu Glu Val Pro
        50                  55                  60 agc ttc cgc ctg ggc cag cat ctc tac ggc acg tac cgc aca cgg ctg    240
Ser Phe Arg Leu Gly Gln His Leu Tyr Gly Thr Tyr Arg Thr Arg Leu
65                  70                  75                  80 cat gag aac aac tgg atc tgc atc cag gag gac acc ggc ctc ctc tac    288
His Glu Asn Asn Trp Ile Cys Ile Gln Glu Asp Thr Gly Leu Leu Tyr
                85                  90                  95 ctt aac cgg agc ctg gac cat agc tcc tgg gag aag ctc agt gtc cgc    336
Leu Asn Arg Ser Leu Asp His Ser Ser Trp Glu Lys Leu Ser Val Arg
            100                 105                 110 aac cgc ggc ttt ccc ctg ctc acc gtc tac ctc aag gtc ttc ctg tca    384
Asn Arg Gly Phe Pro Leu Leu Thr Val Tyr Leu Lys Val Phe Leu Ser
        115                 120                 125 ccc aca tcc ctt cgt gag ggc gag tgc cag tgg cca ggc tgt gcc cgc    432
Pro Thr Ser Leu Arg Glu Gly Glu Cys Gln Trp Pro Gly Cys Ala Arg
    130                 135                 140 gta tac ttc tcc ttc ttc aac acc tcc ttt cca gcc tgc agc tcc ctc    480
Val Tyr Phe Ser Phe Phe Asn Thr Ser Phe Pro Ala Cys Ser Ser Leu
145                 150                 155                 160 aag ccc cgg gag ctc tgc ttc cca gag aca agg ccc tcc ttc cgc att    528
Lys Pro Arg Glu Leu Cys Phe Pro Glu Thr Arg Pro Ser Phe Arg Ile
                165                 170                 175 cgg gag aac cga ccc cca ggc acc ttc cac cag ttc cgc ctg ctg cct    576
Arg Glu Asn Arg Pro Pro Gly Thr Phe His Gln Phe Arg Leu Leu Pro
            180                 185                 190 gtg cag ttc ttg tgc ccc aac atc agc gtg gcc tac agg ctc ctg gag    624
Val Gln Phe Leu Cys Pro Asn Ile Ser Val Ala Tyr Arg Leu Leu Glu
        195                 200                 205 ggt gag ggt ctg ccc ttc cgc tgc gcc ccg gac agc ctg gag gtg agc    672
Gly Glu Gly Leu Pro Phe Arg Cys Ala Pro Asp Ser Leu Glu Val Ser
    210                 215                 220 acg cgc tgg gcc ctg gac cgc gag cag cgg gag aag tac gag ctg gtg    720
Thr Arg Trp Ala Leu Asp Arg Glu Gln Arg Glu Lys Tyr Glu Leu Val
225                 230                 235                 240 gcc gtg tgc acc gtg cac gcc ggc gcg cgc gag gag gtg gtg atg gtg    768
Ala Val Cys Thr Val His Ala Gly Ala Arg Glu Glu Val Val Met Val
                245                 250                 255 ccc ttc ccg gtg acc gtg tac gac gag gac gac tcg gcg ccc acc ttc    816
Pro Phe Pro Val Thr Val Tyr Asp Glu Asp Asp Ser Ala Pro Thr Phe
            260                 265                 270 ccc gcg ggc gtc gac acc gcc agc gcc gtg gtg gag ttc aag cgg aag    864
Pro Ala Gly Val Asp Thr Ala Ser Ala Val Val Glu Phe Lys Arg Lys
        275                 280                 285 gag gac acc gtg gtg gcc acg ctg cgt gtc ttc gat gca gac gtg gta    912
Glu Asp Thr Val Val Ala Thr Leu Arg Val Phe Asp Ala Asp Val Val
    290                 295                 300 cct gca tca ggg gag ctg gtg agg cgg tac aca agc acg ctg ctc ccc    960
Pro Ala Ser Gly Glu Leu Val Arg Arg Tyr Thr Ser Thr Leu Leu Pro
305                 310                 315                 320
```

-continued

| | |
|---|---|
| ggg gac acc tgg gcc cag cag acc ttc cgg gtg gaa cac tgg ccc aac<br>Gly Asp Thr Trp Ala Gln Gln Thr Phe Arg Val Glu His Trp Pro Asn<br>                  325                                330                            335 | 1008 |
| gag acc tcg gtc cag gcc aac ggc agc ttc gtg cgg gcg acc gta cat<br>Glu Thr Ser Val Gln Ala Asn Gly Ser Phe Val Arg Ala Thr Val His<br>340                                345                                350 | 1056 |
| gac tat agg ctg gtt ctc aac cgg aac ctc tcc atc tcg gag aac cgc<br>Asp Tyr Arg Leu Val Leu Asn Arg Asn Leu Ser Ile Ser Glu Asn Arg<br>                  355                                360                            365 | 1104 |
| acc atg cag ctg gcg gtg ctg gtc aat gac tca gac ttc cag ggc cca<br>Thr Met Gln Leu Ala Val Leu Val Asn Asp Ser Asp Phe Gln Gly Pro<br>370                                375                                380 | 1152 |
| gga gcg ggc gtc ctc ttg ctc cac ttc aac gtg tcg gtg ctg ccg gtc<br>Gly Ala Gly Val Leu Leu Leu His Phe Asn Val Ser Val Leu Pro Val<br>385                                390                                395                            400 | 1200 |
| agc ctg cac ctg ccc agt acc tac tcc ctc tcc gtg agc agg agg gct<br>Ser Leu His Leu Pro Ser Thr Tyr Ser Leu Ser Val Ser Arg Arg Ala<br>                                405                                410                            415 | 1248 |
| cgc cga ttt gcc cag atc ggg aaa gtc tgt gtg gaa aac tgc cag gca<br>Arg Arg Phe Ala Gln Ile Gly Lys Val Cys Val Glu Asn Cys Gln Ala<br>                  420                                425                            430 | 1296 |
| ttc agt ggc atc aac gtc cag tac aag ctg cat tcc tct ggt gcc aac<br>Phe Ser Gly Ile Asn Val Gln Tyr Lys Leu His Ser Ser Gly Ala Asn<br>                    435                                440                            445 | 1344 |
| tgc agc acg cta ggg gtg gtc acc tca gcc gag gac acc tcg ggg atc<br>Cys Ser Thr Leu Gly Val Val Thr Ser Ala Glu Asp Thr Ser Gly Ile<br>450                                455                                460 | 1392 |
| ctg ttt gtg aat gac acc aag gcc ctg cgg cgg ccc aag tgt gcc gaa<br>Leu Phe Val Asn Asp Thr Lys Ala Leu Arg Arg Pro Lys Cys Ala Glu<br>465                                470                                475                            480 | 1440 |
| ctt cac tac atg gtg gtg gcc acc gac cag cag acc tct agg cag gcc<br>Leu His Tyr Met Val Val Ala Thr Asp Gln Gln Thr Ser Arg Gln Ala<br>                              485                                490                            495 | 1488 |
| cag gcc cag ctg ctt gta aca gtg gag ggg tca tat gtg gcc gag gag<br>Gln Ala Gln Leu Leu Val Thr Val Glu Gly Ser Tyr Val Ala Glu Glu<br>                  500                                505                            510 | 1536 |
| gcg ggc tgc ccc ctg tcc tgt gca gtc agc aag aga cgg ctg gag tgt<br>Ala Gly Cys Pro Leu Ser Cys Ala Val Ser Lys Arg Arg Leu Glu Cys<br>                  515                                520                            525 | 1584 |
| gag gag tgt ggc ggc ctg ggc tcc cca aca ggc agg tgt gag tgg agg<br>Glu Glu Cys Gly Gly Leu Gly Ser Pro Thr Gly Arg Cys Glu Trp Arg<br>530                                535                                540 | 1632 |
| caa gga gat ggc aaa ggg atc acc agg aac ttc tcc acc tgc tct ccc<br>Gln Gly Asp Gly Lys Gly Ile Thr Arg Asn Phe Ser Thr Cys Ser Pro<br>545                                550                                555                            560 | 1680 |
| agc acc aag acc tgc ccc gac ggc cac tgc gat gtt gtg gag acc caa<br>Ser Thr Lys Thr Cys Pro Asp Gly His Cys Asp Val Val Glu Thr Gln<br>                                565                                570                            575 | 1728 |
| gac atc aac att tgc cct cag gac tgc ctc cgg ggc agc att gtt ggg<br>Asp Ile Asn Ile Cys Pro Gln Asp Cys Leu Arg Gly Ser Ile Val Gly<br>                  580                                585                            590 | 1776 |
| gga cac gag cct ggg gag ccc cgg ggg att aaa gct ggc tat ggc acc<br>Gly His Glu Pro Gly Glu Pro Arg Gly Ile Lys Ala Gly Tyr Gly Thr<br>                                595                                600                            605 | 1824 |
| tgc aac tgc ttc cct gag gag gag aag tgc ttc tgc gag ccc gaa gac<br>Cys Asn Cys Phe Pro Glu Glu Glu Lys Cys Phe Cys Glu Pro Glu Asp<br>610                                615                                620 | 1872 |
| atc cag gat cca ctg tgc gac gag ctg tgc cgc acg gtg atc gca gcc<br>Ile Gln Asp Pro Leu Cys Asp Glu Leu Cys Arg Thr Val Ile Ala Ala<br>625                                630                                635                            640 | 1920 |

```
gct gtc ctc ttc tcc ttc atc gtc tcg gtg ctg ctg tct gcc ttc tgc    1968
Ala Val Leu Phe Ser Phe Ile Val Ser Val Leu Leu Ser Ala Phe Cys
            645                 650                 655 atc cac tgc tac cac aag ttt gcc cac aag cca ccc atc tcc tca gct    2016
Ile His Cys Tyr His Lys Phe Ala His Lys Pro Pro Ile Ser Ser Ala
660                 665                 670 gag atg acc ttc cgg agg ccc gcc cag gcc ttc ccg gtc agc tac tcc    2064
Glu Met Thr Phe Arg Arg Pro Ala Gln Ala Phe Pro Val Ser Tyr Ser
        675                 680                 685 tct tcc ggt gcc cgc cgg ccc tcg ctg gac tcc atg gag aac cag gtc    2112
Ser Ser Gly Ala Arg Arg Pro Ser Leu Asp Ser Met Glu Asn Gln Val
            690                 695                 700 tcc gtg gat gcc ttc aag atc ctg cag cct gag gga act ggc atg ata    2160
Ser Val Asp Ala Phe Lys Ile Leu Gln Pro Glu Gly Thr Gly Met Ile
705                 710                 715                 720 gat gaa gag ttc act gtt gca aga ctc tac att agc aaa atg aag tca    2208
Asp Glu Glu Phe Thr Val Ala Arg Leu Tyr Ile Ser Lys Met Lys Ser
                725                 730                 735 gaa gta aaa acc atg gtg aaa cgt tgc aag cag tta gaa agc aca caa    2256
Glu Val Lys Thr Met Val Lys Arg Cys Lys Gln Leu Glu Ser Thr Gln
            740                 745                 750 act gag agc aac aaa aaa atg gaa gaa aat gaa aag gag tta gca gca    2304
Thr Glu Ser Asn Lys Lys Met Glu Glu Asn Glu Lys Glu Leu Ala Ala
        755                 760                 765 tgt cag ctt cgt atc tct caa cat gaa gcc aaa atc aag tca ttg act    2352
Cys Gln Leu Arg Ile Ser Gln His Glu Ala Lys Ile Lys Ser Leu Thr
            770                 775                 780 gaa tac ctt caa aat gtg gaa caa aag aaa aga cag ttg gag gaa tct    2400
Glu Tyr Leu Gln Asn Val Glu Gln Lys Lys Arg Gln Leu Glu Glu Ser
785                 790                 795                 800 gtc gat gcc ctc agt gaa gaa cta gtc cag ctt cga gca caa gag aaa    2448
Val Asp Ala Leu Ser Glu Glu Leu Val Gln Leu Arg Ala Gln Glu Lys
                805                 810                 815 gtc cat gaa atg gaa aag gag cac tta aat aag gtt cag act gca aat    2496
Val His Glu Met Glu Lys Glu His Leu Asn Lys Val Gln Thr Ala Asn
            820                 825                 830 gaa gtt aag caa gct gtt gaa cag cag atc cag agc cat aga gaa act    2544
Glu Val Lys Gln Ala Val Glu Gln Gln Ile Gln Ser His Arg Glu Thr
        835                 840                 845 cat caa aaa cag atc agt agt ttg aga gat gaa gta gaa gca aaa gca    2592
His Gln Lys Gln Ile Ser Ser Leu Arg Asp Glu Val Glu Ala Lys Ala
850                 855                 860 aaa ctt att act gat ctt caa gac caa aac cag aaa atg atg tta gag    2640
Lys Leu Ile Thr Asp Leu Gln Asp Gln Asn Gln Lys Met Met Leu Glu
865                 870                 875                 880 cag gaa cgt cta aga gta gaa cat gag aag ttg aaa gcc aca gat cag    2688
Gln Glu Arg Leu Arg Val Glu His Glu Lys Leu Lys Ala Thr Asp Gln
                885                 890                 895 gaa aag agc aga aaa cta cat gaa ctt acg gtt atg caa gat aga cga    2736
Glu Lys Ser Arg Lys Leu His Glu Leu Thr Val Met Gln Asp Arg Arg
            900                 905                 910 gaa caa gca aga caa gac ttg aag ggt ttg gaa gag aca gtg gca aaa    2784
Glu Gln Ala Arg Gln Asp Leu Lys Gly Leu Glu Glu Thr Val Ala Lys
        915                 920                 925 gaa ctt cag act tta cac aac ctg cgc aaa ctc ttt gtt cag gac ctg    2832
Glu Leu Gln Thr Leu His Asn Leu Arg Lys Leu Phe Val Gln Asp Leu
930                 935                 940 gct aca aga gtt aaa aag agt gct gag att gat tct gat gac acc gga    2880
Ala Thr Arg Val Lys Lys Ser Ala Glu Ile Asp Ser Asp Asp Thr Gly
```

```
                   945                 950                 955                 960
ggc agc gct gct cag aag caa aaa atc tcc ttt ctt gaa aat aat ctt       2928
Gly Ser Ala Ala Gln Lys Gln Lys Ile Ser Phe Leu Glu Asn Asn Leu
                965                 970                 975 gaa cag ctc act aaa gtg cac aaa cag ttg gta cgt gat aat gca gat       2976
Glu Gln Leu Thr Lys Val His Lys Gln Leu Val Arg Asp Asn Ala Asp
            980                 985                 990 ctc cgc tgt gaa ctt cct aag ttg gaa aag cga ctt cga gct aca gct       3024
Leu Arg Cys Glu Leu Pro Lys Leu Glu Lys Arg Leu Arg Ala Thr Ala
            995                 1000                1005 gag aga gtg aaa gct ttg gaa tca gca ctg aaa gaa gct aaa gaa           3069
Glu Arg Val Lys Ala Leu Glu Ser Ala Leu Lys Glu Ala Lys Glu
        1010                1015                1020 aat gca tct cgt gat cgc aaa cgc tat cag caa gaa gta gat cgc           3114
Asn Ala Ser Arg Asp Arg Lys Arg Tyr Gln Gln Glu Val Asp Arg
        1025                1030                1035 ata aag gaa gca gtc agg tca aag aat atg gcc aga aga ggg cat           3159
Ile Lys Glu Ala Val Arg Ser Lys Asn Met Ala Arg Arg Gly His
        1040                1045                1050 tct gca cag att gct aaa cct att cgt ccc ggg caa cat cca gca           3204
Ser Ala Gln Ile Ala Lys Pro Ile Arg Pro Gly Gln His Pro Ala
        1055                1060                1065 gct tct cca act cac cca agt gca att cgt gga gga ggt gca ttc           3249
Ala Ser Pro Thr His Pro Ser Ala Ile Arg Gly Gly Gly Ala Phe
        1070                1075                1080 gtt cag aac agc cag cca gtg gca gtg cga ggt gga gga ggc aaa           3294
Val Gln Asn Ser Gln Pro Val Ala Val Arg Gly Gly Gly Gly Lys
        1085                1090                1095 caa gtg taa                                                           3303
Gln Val
    1100

<210> SEQ ID NO 4
<211> LENGTH: 1100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Ala Lys Ala Thr Ser Gly Ala Ala Gly Leu Arg Leu Leu Leu Leu
1               5                   10                  15

Leu Leu Leu Pro Leu Leu Gly Lys Val Ala Leu Gly Leu Tyr Phe Ser
                20                  25                  30

Arg Asp Ala Tyr Trp Glu Lys Leu Tyr Val Asp Gln Ala Ala Gly Thr
            35                  40                  45

Pro Leu Leu Tyr Val His Ala Leu Arg Asp Ala Pro Glu Glu Val Pro
        50                  55                  60

Ser Phe Arg Leu Gly Gln His Leu Tyr Gly Thr Tyr Arg Thr Arg Leu
65                  70                  75                  80

His Glu Asn Asn Trp Ile Cys Ile Gln Glu Asp Thr Gly Leu Leu Tyr
                85                  90                  95

Leu Asn Arg Ser Leu Asp His Ser Ser Trp Glu Lys Leu Ser Val Arg
            100                 105                 110

Asn Arg Gly Phe Pro Leu Leu Thr Val Tyr Leu Lys Val Phe Leu Ser
        115                 120                 125

Pro Thr Ser Leu Arg Glu Gly Glu Cys Gln Trp Pro Gly Cys Ala Arg
        130                 135                 140
```

```
Val Tyr Phe Ser Phe Phe Asn Thr Ser Phe Pro Ala Cys Ser Ser Leu
145                 150                 155                 160

Lys Pro Arg Glu Leu Cys Phe Pro Glu Thr Arg Pro Ser Phe Arg Ile
                165                 170                 175

Arg Glu Asn Arg Pro Pro Gly Thr Phe His Gln Phe Arg Leu Leu Pro
            180                 185                 190

Val Gln Phe Leu Cys Pro Asn Ile Ser Val Ala Tyr Arg Leu Leu Glu
        195                 200                 205

Gly Glu Gly Leu Pro Phe Arg Cys Ala Pro Asp Ser Leu Glu Val Ser
    210                 215                 220

Thr Arg Trp Ala Leu Asp Arg Glu Gln Arg Lys Tyr Glu Leu Val
225                 230                 235                 240

Ala Val Cys Thr Val His Ala Gly Ala Arg Glu Glu Val Met Val
                245                 250                 255

Pro Phe Pro Val Thr Val Tyr Asp Glu Asp Asp Ser Ala Pro Thr Phe
            260                 265                 270

Pro Ala Gly Val Asp Thr Ala Ser Ala Val Val Glu Phe Lys Arg Lys
            275                 280                 285

Glu Asp Thr Val Val Ala Thr Leu Arg Val Phe Asp Ala Asp Val Val
290                 295                 300

Pro Ala Ser Gly Glu Leu Val Arg Arg Tyr Thr Ser Thr Leu Leu Pro
305                 310                 315                 320

Gly Asp Thr Trp Ala Gln Gln Thr Phe Arg Val Glu His Trp Pro Asn
                325                 330                 335

Glu Thr Ser Val Gln Ala Asn Gly Ser Phe Val Arg Ala Thr Val His
                340                 345                 350

Asp Tyr Arg Leu Val Leu Asn Arg Asn Leu Ser Ile Ser Glu Asn Arg
            355                 360                 365

Thr Met Gln Leu Ala Val Leu Val Asn Asp Ser Asp Phe Gln Gly Pro
            370                 375                 380

Gly Ala Gly Val Leu Leu Leu His Phe Asn Val Ser Val Leu Pro Val
385                 390                 395                 400

Ser Leu His Leu Pro Ser Thr Tyr Ser Leu Ser Val Ser Arg Arg Ala
                405                 410                 415

Arg Arg Phe Ala Gln Ile Gly Lys Val Cys Val Glu Asn Cys Gln Ala
            420                 425                 430

Phe Ser Gly Ile Asn Val Gln Tyr Lys Leu His Ser Ser Gly Ala Asn
            435                 440                 445

Cys Ser Thr Leu Gly Val Val Thr Ser Ala Glu Asp Thr Ser Gly Ile
            450                 455                 460

Leu Phe Val Asn Asp Thr Lys Ala Leu Arg Arg Pro Lys Cys Ala Glu
465                 470                 475                 480

Leu His Tyr Met Val Val Ala Thr Asp Gln Gln Thr Ser Arg Gln Ala
                485                 490                 495

Gln Ala Gln Leu Leu Val Thr Val Glu Gly Ser Tyr Val Ala Glu Glu
                500                 505                 510

Ala Gly Cys Pro Leu Ser Cys Ala Val Ser Lys Arg Arg Leu Glu Cys
            515                 520                 525

Glu Glu Cys Gly Gly Leu Gly Ser Pro Thr Gly Arg Cys Glu Trp Arg
            530                 535                 540

Gln Gly Asp Gly Lys Gly Ile Thr Arg Asn Phe Ser Thr Cys Ser Pro
545                 550                 555                 560
```

-continued

```
Ser Thr Lys Thr Cys Pro Asp Gly His Cys Asp Val Glu Thr Gln
            565                 570                 575

Asp Ile Asn Ile Cys Pro Gln Asp Cys Leu Arg Gly Ser Ile Val Gly
        580                 585                 590

Gly His Glu Pro Gly Glu Pro Arg Gly Ile Lys Ala Gly Tyr Gly Thr
            595                 600                 605

Cys Asn Cys Phe Pro Glu Glu Lys Cys Phe Cys Glu Pro Glu Asp
            610                 615                 620

Ile Gln Asp Pro Leu Cys Asp Glu Leu Cys Arg Thr Val Ile Ala Ala
625                 630                 635                 640

Ala Val Leu Phe Ser Phe Ile Val Ser Val Leu Leu Ser Ala Phe Cys
            645                 650                 655

Ile His Cys Tyr His Lys Phe Ala His Lys Pro Pro Ile Ser Ser Ala
            660                 665                 670

Glu Met Thr Phe Arg Arg Pro Ala Gln Ala Phe Pro Val Ser Tyr Ser
            675                 680                 685

Ser Ser Gly Ala Arg Arg Pro Ser Leu Asp Ser Met Glu Asn Gln Val
            690                 695                 700

Ser Val Asp Ala Phe Lys Ile Leu Gln Pro Glu Gly Thr Gly Met Ile
705                 710                 715                 720

Asp Glu Glu Phe Thr Val Ala Arg Leu Tyr Ile Ser Lys Met Lys Ser
            725                 730                 735

Glu Val Lys Thr Met Val Lys Arg Cys Lys Gln Leu Glu Ser Thr Gln
            740                 745                 750

Thr Glu Ser Asn Lys Lys Met Glu Glu Asn Lys Glu Leu Ala Ala
            755                 760                 765

Cys Gln Leu Arg Ile Ser Gln His Glu Ala Lys Ile Lys Ser Leu Thr
            770                 775                 780

Glu Tyr Leu Gln Asn Val Glu Gln Lys Lys Arg Gln Leu Glu Glu Ser
785                 790                 795                 800

Val Asp Ala Leu Ser Glu Glu Leu Val Gln Leu Arg Ala Gln Glu Lys
            805                 810                 815

Val His Glu Met Glu Lys Glu His Leu Asn Lys Val Gln Thr Ala Asn
            820                 825                 830

Glu Val Lys Gln Ala Val Glu Gln Gln Ile Gln Ser His Arg Glu Thr
            835                 840                 845

His Gln Lys Gln Ile Ser Ser Leu Arg Asp Glu Val Glu Ala Lys Ala
            850                 855                 860

Lys Leu Ile Thr Asp Leu Gln Asp Gln Asn Gln Lys Met Met Leu Glu
865                 870                 875                 880

Gln Glu Arg Leu Arg Val Glu His Glu Lys Leu Lys Ala Thr Asp Gln
            885                 890                 895

Glu Lys Ser Arg Lys Leu His Glu Leu Thr Val Met Gln Asp Arg Arg
            900                 905                 910

Glu Gln Ala Arg Gln Asp Leu Lys Gly Leu Glu Glu Thr Val Ala Lys
            915                 920                 925

Glu Leu Gln Thr Leu His Asn Leu Arg Lys Leu Phe Val Gln Asp Leu
            930                 935                 940

Ala Thr Arg Val Lys Lys Ser Ala Glu Ile Asp Ser Asp Thr Gly
945                 950                 955                 960

Gly Ser Ala Ala Gln Lys Gln Lys Ile Ser Phe Leu Glu Asn Asn Leu
            965                 970                 975

Glu Gln Leu Thr Lys Val His Lys Gln Leu Val Arg Asp Asn Ala Asp
```

```
                980             985              990
Leu Arg Cys Glu Leu Pro Lys Leu  Glu Lys Arg Leu Arg  Ala Thr Ala
            995              1000             1005

Glu Arg  Val Lys Ala Leu Glu  Ser Ala Leu Lys Glu  Ala Lys Glu
    1010             1015              1020

Asn Ala  Ser Arg Asp Arg Lys  Arg Tyr Gln Gln Glu  Val Asp Arg
    1025             1030              1035

Ile Lys  Glu Ala Val Arg Ser  Lys Asn Met Ala Arg  Arg Gly His
    1040             1045              1050

Ser Ala  Gln Ile Ala Lys Pro  Ile Arg Pro Gly Gln  His Pro Ala
    1055             1060              1065

Ala Ser  Pro Thr His Pro Ser  Ala Ile Arg Gly Gly  Gly Ala Phe
    1070             1075              1080

Val Gln  Asn Ser Gln Pro Val  Ala Val Arg Gly Gly  Gly Gly Lys
    1085             1090              1095

Gln Val
    1100

<210> SEQ ID NO 5
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (16)..(185)
<223> OTHER INFORMATION: a, c, t, g, unknown or other

<400> SEQUENCE: 5
atcgcaccag cgtgtnnnnn nnnnnnnnnn nnnnnnnnnn nnnnnnnnnn nnnnnnnnnn        60
nnnnnnnnnn nnnnnnnnnn nnnnnnnnnn nnnnnnnnnn nnnnnnnnnn nnnnnnnnnn       120
nnnnnnnnnn nnnnnnnnnn nnnnnnnnnn nnnnnnnnnn nnnnnnnnnn nnnnnnnnnn       180
nnnnncactg cggctcctca                                                   200

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Val Asp Asn Asn Gly Val Ala Ile Gly Ile Glu Ala Leu Asp Lys
1               5                   10                  15

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Glu Asp Pro Lys Trp Glu Phe Pro Arg Lys Asn Leu Val Leu Gly Lys
1               5                   10                  15

Thr
```

<210> SEQ ID NO 8
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8
tgtaaaggag gatc                                                            14

<210> SEQ ID NO 9
<211> LENGTH: 976
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

```
Met Ala Asp Leu Ala Glu Cys Asn Ile Lys Val Met Cys Arg Phe Arg
1               5                   10                  15

Pro Leu Asn Glu Ser Glu Val Asn Arg Gly Asp Lys Tyr Ile Ala Lys
            20                  25                  30

Phe Gln Gly Glu Asp Thr Val Ile Ala Ser Lys Pro Tyr Ala Phe
        35                  40                  45

Asp Arg Val Phe Gln Ser Ser Thr Ser Gln Glu Gln Val Tyr Asn Asp
 50                  55                  60

Cys Ala Lys Lys Ile Val Lys Asp Val Leu Glu Gly Tyr Asn Gly Thr
65                  70                  75                  80

Ile Phe Ala Tyr Gly Gln Thr Ser Ser Gly Lys Thr His Thr Met Glu
                85                  90                  95

Gly Lys Leu His Asp Pro Glu Gly Met Gly Ile Ile Pro Arg Ile Val
            100                 105                 110

Gln Asp Ile Phe Asn Tyr Ile Tyr Ser Met Asp Glu Asn Leu Glu Phe
        115                 120                 125

His Ile Lys Val Ser Tyr Phe Glu Ile Tyr Leu Asp Lys Ile Arg Asp
    130                 135                 140

Leu Leu Asp Val Ser Lys Thr Asn Leu Ser Val His Glu Asp Lys Asn
145                 150                 155                 160

Arg Val Pro Tyr Val Lys Gly Cys Thr Glu Arg Phe Val Cys Ser Pro
                165                 170                 175

Asp Glu Val Met Asp Thr Ile Asp Glu Gly Lys Ser Asn Arg His Val
            180                 185                 190

Ala Val Thr Asn Met Asn Glu His Ser Ser Arg Ser His Ser Ile Phe
        195                 200                 205

Leu Ile Asn Val Lys Gln Glu Asn Thr Gln Thr Glu Gln Lys Leu Ser
    210                 215                 220

Gly Lys Leu Tyr Leu Val Asp Leu Ala Gly Ser Glu Lys Val Ser Lys
225                 230                 235                 240

Thr Gly Ala Glu Gly Ala Val Leu Asp Glu Ala Lys Asn Ile Asn Lys
                245                 250                 255

Ser Leu Ser Ala Leu Gly Asn Val Ile Ser Ala Leu Ala Glu Gly Ser
            260                 265                 270

Thr Tyr Val Pro Tyr Arg Asp Ser Lys Met Thr Arg Ile Leu Gln Asp
        275                 280                 285

Ser Leu Gly Gly Asn Cys Arg Thr Thr Ile Ile Cys Cys Ser Pro Ser
```

```
                290                 295                 300
Ser Tyr Asn Glu Ser Glu Thr Lys Ser Thr Leu Leu Phe Gly Gln Arg
305                 310                 315                 320

Ala Lys Thr Ile Lys Asn Thr Val Cys Val Asn Val Glu Leu Thr Ala
                325                 330                 335

Glu Gln Trp Lys Lys Tyr Glu Lys Glu Lys Asn Lys Ile
                340                 345                 350

Leu Arg Asn Thr Ile Gln Trp Leu Glu Asn Glu Leu Asn Arg Trp Arg
                355                 360                 365

Asn Gly Glu Thr Val Pro Ile Asp Glu Gln Phe Asp Lys Glu Lys Ala
            370                 375                 380

Asn Leu Glu Ala Phe Thr Val Asp Lys Asp Ile Thr Leu Thr Asn Asp
385                 390                 395                 400

Lys Pro Ala Thr Ala Ile Gly Val Ile Gly Asn Phe Thr Asp Ala Glu
                405                 410                 415

Arg Arg Lys Cys Glu Glu Glu Ile Ala Lys Leu Tyr Lys Gln Leu Asp
                420                 425                 430

Asp Lys Asp Glu Glu Ile Asn Gln Gln Ser Gln Leu Val Glu Lys Leu
            435                 440                 445

Lys Thr Gln Met Leu Asp Gln Glu Leu Leu Ala Ser Thr Arg Arg
                450                 455                 460

Asp Gln Asp Asn Met Gln Ala Glu Leu Asn Arg Leu Gln Ala Glu Asn
465                 470                 475                 480

Asp Ala Ser Lys Glu Glu Val Lys Glu Val Leu Gln Ala Leu Glu Glu
                485                 490                 495

Leu Ala Val Asn Tyr Asp Gln Lys Ser Gln Glu Val Glu Asp Lys Thr
                500                 505                 510

Lys Glu Tyr Glu Leu Leu Ser Asp Glu Leu Asn Gln Lys Ser Ala Thr
                515                 520                 525

Leu Ala Ser Ile Asp Ala Glu Leu Gln Lys Leu Lys Glu Met Thr Asn
            530                 535                 540

His Gln Lys Lys Arg Ala Ala Glu Met Met Ala Ser Leu Leu Lys Asp
545                 550                 555                 560

Leu Ala Glu Ile Gly Ile Ala Val Gly Asn Asn Asp Val Lys Glu Asp
                565                 570                 575

Pro Lys Trp Glu Phe Pro Arg Lys Asn Leu Val Leu Gly Lys Thr Leu
                580                 585                 590

Gly Glu Gly Glu Phe Gly Lys Val Val Lys Ala Thr Ala Phe His Leu
            595                 600                 605

Lys Gly Arg Ala Gly Tyr Thr Thr Val Ala Val Lys Met Leu Lys Glu
            610                 615                 620

Asn Ala Ser Pro Ser Glu Leu Arg Asp Leu Leu Ser Glu Phe Asn Val
625                 630                 635                 640

Leu Lys Gln Val Asn His Pro His Val Ile Lys Leu Tyr Gly Ala Cys
                645                 650                 655

Ser Gln Asp Gly Pro Leu Leu Leu Ile Val Glu Tyr Ala Lys Tyr Gly
                660                 665                 670

Ser Leu Arg Gly Phe Leu Arg Glu Ser Arg Lys Val Gly Pro Gly Tyr
                675                 680                 685

Leu Gly Ser Gly Gly Ser Arg Asn Ser Ser Leu Asp His Pro Asp
            690                 695                 700

Glu Arg Ala Leu Thr Met Gly Asp Leu Ile Ser Phe Ala Trp Gln Ile
705                 710                 715                 720
```

```
Ser Gln Gly Met Gln Tyr Leu Ala Glu Met Lys Leu Val His Arg Asp
            725                 730                 735
Leu Ala Ala Arg Asn Ile Leu Val Ala Glu Gly Arg Lys Met Lys Ile
            740                 745                 750
Ser Asp Phe Gly Leu Ser Arg Asp Val Tyr Glu Glu Asp Ser Tyr Val
            755                 760                 765
Lys Arg Ser Gln Gly Arg Ile Pro Val Lys Trp Met Ala Ile Glu Ser
    770                 775                 780
Leu Phe Asp His Ile Tyr Thr Thr Gln Ser Asp Val Trp Ser Phe Gly
785                 790                 795                 800
Val Leu Leu Trp Glu Ile Val Thr Leu Gly Gly Asn Pro Tyr Pro Gly
                805                 810                 815
Ile Pro Pro Glu Arg Leu Phe Asn Leu Leu Lys Thr Gly His Arg Met
                820                 825                 830
Glu Arg Pro Asp Asn Cys Ser Glu Glu Met Tyr Arg Leu Met Leu Gln
            835                 840                 845
Cys Trp Lys Gln Glu Pro Asp Lys Arg Pro Val Phe Ala Asp Ile Ser
    850                 855                 860
Lys Asp Leu Glu Lys Met Met Val Lys Arg Arg Asp Tyr Leu Asp Leu
865                 870                 875                 880
Ala Ala Ser Thr Pro Ser Asp Ser Leu Ile Tyr Asp Asp Gly Leu Ser
                885                 890                 895
Glu Glu Glu Thr Pro Leu Val Asp Cys Asn Asn Ala Pro Leu Pro Arg
            900                 905                 910
Ala Leu Pro Ser Thr Trp Ile Glu Asn Lys Leu Tyr Gly Met Ser Asp
    915                 920                 925
Pro Asn Trp Pro Gly Glu Ser Pro Val Pro Leu Thr Arg Ala Asp Gly
    930                 935                 940
Thr Asn Thr Gly Phe Pro Arg Tyr Pro Asn Asp Ser Val Tyr Ala Asn
945                 950                 955                 960
Trp Met Leu Ser Pro Ser Ala Ala Lys Leu Met Asp Thr Phe Asp Ser
                965                 970                 975
```